(12) United States Patent
Kiani et al.

(10) Patent No.: US 12,235,941 B2
(45) Date of Patent: Feb. 25, 2025

(54) DISPLAY LAYOUT AND INTERACTIVE OBJECTS FOR PATIENT MONITORING

(71) Applicant: Masimo Corporation, Irvine, CA (US)

(72) Inventors: Massi Joe E. Kiani, Laguna Niguel, CA (US); Bilal Muhsin, San Clemente, CA (US); Ammar Al-Ali, San Juan Capistrano, CA (US); Nicholas Evan Barker, Laguna Beach, CA (US); Chad A. DeJong, Los Angeles, CA (US); Omar Ahmed, Lake Forest, CA (US); Keith Ward Indorf, Riverside, CA (US); Steve Coon, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 475 days.

(21) Appl. No.: 17/073,133

(22) Filed: Oct. 16, 2020

(65) Prior Publication Data

US 2021/0117525 A1    Apr. 22, 2021

Related U.S. Application Data

(60) Provisional application No. 63/017,151, filed on Apr. 29, 2020, provisional application No. 62/923,248, filed on Oct. 18, 2019.

(51) Int. Cl.
*G06F 21/32* (2013.01)
*G16H 10/60* (2018.01)
(Continued)

(52) U.S. Cl.
CPC ............ *G06F 21/32* (2013.01); *G16H 10/60* (2018.01); *G16H 40/20* (2018.01); *G16H 40/67* (2018.01);
(Continued)

(58) Field of Classification Search
CPC ........ G06F 21/32; G16H 40/67; G16H 40/20; G16H 50/50; G16H 10/60; G16H 80/00
See application file for complete search history.

(56) References Cited

U.S. PATENT DOCUMENTS 3,942,751 A    3/1976   Fay
4,960,128 A    10/1990  Gordon et al.
(Continued)

FOREIGN PATENT DOCUMENTS

AU    2016336420      6/2021
JP    2007260072    * 10/2007  ............. H04M 1/11
(Continued)

OTHER PUBLICATIONS

US 2024/0016391 A1, 01/2024, Lapotko et al. (withdrawn)
(Continued)

*Primary Examiner* — Towfiq Elahi
(74) *Attorney, Agent, or Firm* — Knobbe, Martens, Olson & Bear, LLP

(57) ABSTRACT

A physiological patient monitoring system with a healthcare professional-facing interface is disclosed. The healthcare professional interface may only display by default the most critical non-confidential patient information. To access the full range of features in the system, clinicians can unlock the device. Once unlocked, clinicians can access all of a patient's treatment history, and all the data may be consolidated and presented intuitively.

20 Claims, 59 Drawing Sheets

(51) Int. Cl.
*G16H 40/20* (2018.01)
*G16H 40/67* (2018.01)
*G16H 50/50* (2018.01)
*G16H 80/00* (2018.01)
*A61B 5/00* (2006.01)

(52) U.S. Cl.
CPC ............. *G16H 50/50* (2018.01); *G16H 80/00* (2018.01); *A61B 5/0024* (2013.01)

(56) References Cited

U.S. PATENT DOCUMENTS

| | | |
|---|---|---|
| 4,964,408 A | 10/1990 | Hink et al. |
| 5,319,355 A | 6/1994 | Russek |
| 5,319,747 A | 6/1994 | Gerrissen et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,594,469 A | 1/1997 | Freeman et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| D385,547 S | 10/1997 | Snell |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| D395,878 S | 7/1998 | Copeland et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| D436,580 S | 1/2001 | Navano et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |

(56) References Cited

U.S. PATENT DOCUMENTS

| | | |
|---|---|---|
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| D656,946 S | 4/2012 | Judy |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| D693,835 S | 11/2013 | Daniel |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| D709,077 S | 7/2014 | Jonsson et al. |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,972,272 B1 * | 3/2015 | Dvorak .............. G16H 40/63 705/3 |
| 8,989,831 B2 | 3/2015 | Al-Ali et al. |
| D726,205 S | 4/2015 | Angelides |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| D759,063 S | 6/2016 | Chen |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |

(56) References Cited

U.S. PATENT DOCUMENTS

| | | |
|---|---|---|
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| D815,147 S | 4/2018 | Linzie et al. |
| D815,661 S | 4/2018 | Anzures et al. |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| D826,258 S | 8/2018 | Silva |
| D830,412 S | 10/2018 | Linzie et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,579,245 B1 | 3/2020 | White |
| 10,608,817 B2 | 3/2020 | Haider et al. |
| D880,477 S | 4/2020 | Forrest et al. |
| D881,225 S | 4/2020 | Elgena et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D895,678 S | 9/2020 | Levy |
| D895,679 S | 9/2020 | Levy |
| D896,271 S | 9/2020 | Levy |
| D896,839 S | 9/2020 | Levy |
| D896,840 S | 9/2020 | Levy |
| D897,098 S | 9/2020 | Al-Ali |
| D897,372 S | 9/2020 | Levy |
| 10,779,098 B2 | 9/2020 | Iswanto et al. |
| D899,449 S | 10/2020 | Essex |
| D900,872 S | 11/2020 | Fixler et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D924,264 S | 7/2021 | Chou et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| D937,875 S | 12/2021 | Harvey |
| D938,961 S | 12/2021 | Hui |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |

(56) References Cited

U.S. PATENT DOCUMENTS

| | | |
|---|---|---|
| D950,580 S | 5/2022 | Ahmed |
| D950,583 S | 5/2022 | Zimmer et al. |
| D950,599 S | 5/2022 | Ahmed |
| D950,738 S | 5/2022 | Al-Ali et al. |
| 11,354,018 B2 | 6/2022 | Canneto et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D974,411 S | 1/2023 | Fogu |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| D986,260 S | 5/2023 | Hui |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| D999,776 S | 9/2023 | Dahl et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,010,680 S | 1/2024 | Dahl et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 12,004,869 B2 | 6/2024 | Kiani et al. |
| 12,014,328 B2 | 6/2024 | Wachman et al. |
| D1,036,293 S | 7/2024 | Al-Ali |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| D1,041,511 S | 9/2024 | Indorf et al. |
| 12,076,159 B2 | 9/2024 | Belur Nagaraj et al. |
| D1,044,828 S | 10/2024 | Chandran et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0172789 A1 | 7/2008 | Elliot et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0037170 A1 | 2/2010 | Poole |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0089419 A1 | 4/2012 | Huster |
| 2012/0092162 A1* | 4/2012 | Rosenberg ............ G08B 21/245 340/541 |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0253951 A1 | 9/2013 | Richter et al. |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0188516 A1* | 7/2014 | Kamen .................. G16H 40/67 705/3 |
| 2014/0257852 A1 | 9/2014 | Walker et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0294549 A1 | 10/2015 | Ribble |
| 2016/0180694 A1* | 6/2016 | Rosenberg ............ G08B 21/245 704/274 |
| 2016/0196388 A1 | 7/2016 | Lamego |
| 2016/0283665 A1 | 9/2016 | Sampath et al. |
| 2016/0367173 A1 | 12/2016 | Dalvi et al. |

(56) References Cited

U.S. PATENT DOCUMENTS

| | | |
|---|---|---|
| 2017/0024748 A1 | 1/2017 | Haider |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0258669 A1* | 9/2018 | Moock .............. G06F 1/1632 |
| 2018/0310823 A1 | 11/2018 | Al-Ali et al. |
| 2019/0117070 A1 | 4/2019 | Muhsin et al. |
| 2019/0178010 A1 | 6/2019 | Moock et al. |
| 2019/0189258 A1 | 6/2019 | Barrett |
| 2019/0239787 A1 | 8/2019 | Pauley et al. |
| 2019/0320906 A1 | 10/2019 | Olsen |
| 2019/0374713 A1 | 12/2019 | Kiani et al. |
| 2019/0385753 A1 | 12/2019 | Aganyan et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0204631 A1* | 6/2020 | Subramaniam ....... H04L 67/141 |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2021/0407658 A1 | 12/2021 | Taheri et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0359088 A1 | 11/2022 | Vasalos |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Ai-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |

FOREIGN PATENT DOCUMENTS

| | | |
|---|---|---|
| WO | WO 2011/001248 | 1/2011 |
| WO | WO 2014/059521 | 4/2014 |
| WO | WO 2021/077019 | 4/2021 |
| WO | WO 2023/229980 | 11/2023 |

OTHER PUBLICATIONS

International Search Report and Written Opinion received in PCT Application No. PCT/US2020/056158. dated Jan. 28, 2021 in 15 pages.

How to Write Lab Value Skeleton Diagrams, Apr. 7, 2017, YouTube.com, retrieved Jul. 16, 2024, https://www.youtube.com/watch?v=12f2UdiMXao, pp. 1.

Hunt, Justin, Lab Fishbone Creator, Sep. 27, 2019, YouTube.com, retrieved Jul. 16, 2024, https://www.youtube.com/watch?v=8AX_JDCpZeM, pp. 1.

Lab Fishbone Creator APK, Aug. 15, 2020, ChipApk.com, retrieved Jul. 16, 2024, https://chipapk.com/app/7814806/, pp. 4.

Resley, Justin, Live Vue by Spectrum Medical, May 30, 2023, Linked In.com, retrieved Jul. 16, 2024, https://www.linkedin.com/posts/justin-resley-ccp-emeritus-85a16869_patientsafety-medical-leader-activity-7069351136243191808-NkXj/, pp. 1.

* cited by examiner

↓ NSmith
NAME          DOB              MRN              DIAGNOSIS
Smith, Nora   1957-09-30       132457689        Influenza Restricted Airway alert: TEF Allergy alert: Latex Fall risk Allergy alert: Sulfanomides

VITALS

97 - 88    108 140/50    15 17/7    143/102 220 75/ 130 40
SpO₂ %     PR bpm        PRa rpm    (108)
                                    ABP SYS/DIA mmHg                    — 307

SPOT CHECK PARAMETERS
100.1 101/94    108 140/50    143/102 220 75/ 130 40
21 min ago      PR bpm        (108)
°F                            NIBP SYS/DIA mmHg Patient        Timeline    Live Data    Labs &        Medication &    Patient's
Dashboard                               Imagery       Schedule        Questions

FIG. 3C

↓ NSmith
NAME         DOB            MRN           DIAGNOSIS
Smith, Nora  1957-09-30     132457689     Influenza Restricted Airway alert: TEF | Allergy alert: Latex Fall risk | Allergy alert: Sulfanomides

VITALS | SPOT CHECK PARAMETERS — 307

15  17         97  140       108  140      143/102  220  75
    7       88     50             50       (108)    130  40
RRa rpm   SpO₂ %  PR bpm                    NIBP SYS/DIA mmHg
                                            19 min ago
          143/102  220  75
          (108)    130  40                  100.1  101
          ABP SYS/DIA mmHg                          94
                                            °F
                                            21 min ago

303

Patient      Timeline    Live Data    Labs &      Medication &    Patient's
Dashboard                              Imagery     Schedule        Questions

↓ NSmith

| NAME | DOB | | MRN | DIAGNOSIS |
| Smith, Nora | 1957-09-30 | no connection —308 | 132457689 | Influenza |

Restricted Airway alert: TEF | Allergy alert: Latex

Fall risk | Allergy alert: Sulfanomides

VITALS

```
                    live data not available —309
    - -    88              - -    140              - -    17           - - / - -    220 / 75
                                                                          ( - )    130 / 40
    SpO2%            PRbpm    50         RRa rpm    7      ABP SYS/DIA mmHg
                    live data not available                             - -
ION
```

| 🏃 | ⋮⋮⋮ | 🧬 | 🩺 | 💊 | ❓ |
| Patient Dashboard | Timeline | Live Data | Labs & Imagery | Medication & Schedule | Patient's Questions |

NSmith

| LABEL | MRN | ROOM | | DIAGNOSIS | |
|---|---|---|---|---|---|
| Nsmith | 9870067 | 201a | | Influenza | |

Labs 2019-12-11
Labs 2019-12-10
Labs 2019-12-09
X-Rays 2019-12-09
Labs 2019-12-08

| TEST | RESULT | FLAG | NORMAL RANGE LOW | NORMAL RANGE HIGH | MEASURE |
|---|---|---|---|---|---|
| Album | 3.7 | | 2.7 | 4.4 | g/dL |
| Globolin | 2.1 | | 1.6 | 3.6 | g/dL |
| A/G Ratio | 1.8 | | 0.8 | 2.0 | Ratio |
| ALT (SGPT) | 23 | | 12 | 118 | U/L |
| ALK Phosphatase | 121 | | 5 | 131 | U/L |
| Urea Nitrogen | 21 | | 6 | 31 | mg/dL |
| Creatine | 0.6 | | 0.5 | 1.6 | mg/dL |
| Glucose | 111 | | 70 | 27 | mg/dL |
| Potassium | 4.6 | | 3.6 | 138 | 10^3/mL |
| WBC | 11.2 | | 4.0 | 15.5 | 10^3/mL |
| RB | 7.8 | | 4.8 | 9.3 | 10^3/mL |
| Hemoglobin | 17.7 | | 12.1 | 20.3 | g/dL |
| Hematocrit | 55 | | 36 | 60 | % |
| MCV | 71 | L | 58 | 79 | fL |
| MCH | 22.7 | | 19 | 28 | pg |
| MCHC | 32.2 | H | 30 | 38 | g/dL |
| Platelet Count | 266 | | 170 | 400 | 10^3/mL |
| PLatelet EST | Adequate | | | e | |
| Neutropolis | 42 | H | 60 | 77 | % |
| Bands | 0 | | 0 | 3 | % |
| Lymphocytes | 40 | | 12 | 30 | % |
| Monocytes | 4 | | 3 | 10 | % |
| Eosinophilis | 14 | | 2 | 10 | % |

Patient Dashboard | Timeline | Live Data | Labs & Imagery | Medication & Schedule | Patient's Questions

FIG. 6A

NSmith

LABEL Nsmith

| Labs 2019-12-11 |
| Labs 2019-12-10 |
| Labs 2019-12-09 |
| X-Rays 2019-12-09 |
| Labs 2019-12-08 |

MRN 9870067  ROOM 201a  DIAGNOSIS Influenza

| Na 141 | Cl 99 | BUN 12 | Glu 82 | WBC 7.8 | Hgb 12.8 | Plt 374 |
| K 3.9 | CO2 23 | Creat 0.6 | | | Hct 47 | |

| TEST | RESULT | FLAG | NORMAL RANGE LOW | HIGH | MEASURE |
|---|---|---|---|---|---|
| Album | 3.7 | | 2.7 | 4.4 | g/dL |
| Globolin | 2.1 | | 1.6 | 3.6 | g/dL |
| A/G Ratio | 1.8 | | 0.8 | 2.0 | Ratio |
| ALT (SGPT) | 23 | | 12 | 118 | U/L |
| ALK Phosphatase | 121 | | 5 | 131 | U/L |
| Urea Nitrogen | 21 | | 6 | 31 | mg/dL |
| Creatine | 0.6 | | 0.5 | 1.6 | mg/dL |
| Glucose | 111 | | 70 | 27 | mg/dL |
| Potassium | 4.6 | | 3.6 | 138 | mEq/L |
| WBC | 11.2 | | 4.0 | 15.5 | 10^3/mL |
| RB | 7.8 | | 4.8 | 9.3 | 10^3/mL |
| Hemoglobin | 17.7 | | 12.1 | 20.3 | g/dL |
| Hematocrit | 55 | | 36 | 60 | % |
| MCV | 71 | | 58 | 70 | fl |

Patient Dashboard | Timeline | Live Data | Labs & Imagery | Medication & Schedule | Patient's Questions

NSmith

| | | |
|---|---|---|
| LABEL | MRN | ROOM | DIAGNOSIS |
| NSmith | 9870067 | 201a | Influenza |

[Medication] [Schedule] ← 701

| FORM | MEDICATION | DAYTIME | | | | FREQUENCY |
|---|---|---|---|---|---|---|
| ⊙ | Glipizide 8 MG | ☀ 1 | ☼ 1 | ☾ 1 | | 3 times daily 30 min after meal |
| ⊙ | Aspirin 81 MG | ☀ 1 | ☼ | ☾ 1 | | as needed 30 min after meal |
| ⊖ | Lisinopril 20 MG | ☀ 1 | ☼ 2 | ☾ | | as needed 30 min after meal |
| ⊙ | Metformin 100 MG | ☀ 1 | ☼ | ☾ | | 1 daily 30 min after meal |

702

| Patient Dashboard | Timeline | Live Data | Labs & Imagery | Medication & Schedule | Patient's Questions |
|---|---|---|---|---|---|

FIG. 7A

| NSmith | | |
|---|---|---|
| NAME | DOB | MIN | DISGNOSIS |
| Smith, Nora | 1957-09-30 | 132457689 | Influenza |

| FROM | MEDICATION | DAYTIME | FREQUENCY |
|---|---|---|---|

Medication

Schedule no information available —703

| Patient Dashboard | Timeline | Live Data | Labs & Imagery | Medication & Schedule | Patient's Questions |

Settings

- Patient/ Room/ Warnings
- Home Screen
- Patient Dashboard
- Timeline
- Medication & Schedule
- Live Data
- Labs & Imagery
- Patient's Questions

PATIENT INFORMATION:

NAME: Nsmith ⊗

LABEL: Rsmith ⊗

MRN: 9870067 ⊗

ROOM NUMBER: 201 ⊗

DIAGNOSIS: Influenza ⊗

REQUIRED PROTECTIVE GEAR:
☐ Gloves  ☑ Face mask  ☑ Glasses  ☐ Full body

WARNINGS:

Restricted Airway alert: TEF ⊗ 🗑

Allergy alert: Latex ⊗ 🗑

Fall Risk ⊗ 🗑

Allergy alert: Sulfanomides ⊗ 🗑

Settings

| | MEDICATION | DOSIS | FREQUENCY | TIME | |
|---|---|---|---|---|---|
| ▷ | Glipizide | ▷ 8mg | ▷ 4x daily | ▷ 6am/ 10am 2pm/ 6pm | 🗑 |
| ▷ | Apirin | ▷ 81mg | ▷ as needed max. 2/day | ▷ 30 min after meal | 🗑 |
| ▷ | Lisnopril | ▷ 20mg | ▷ as needed max. 2/day | ▷ 30 min after meal | 🗑 |
| ▷ | Metforin | ▷ 100mg | ▷ 1x daily | ▷ 6:30pm/ 30 min after meal | |
| + | | | | | |

| SCHEDULE | TIME | |
|---|---|---|
| ▷ Cup of water | ▷ 09:00 am | 🗑 |
| ▷ Ten minute walk | ▷ 11:00 am | 🗑 |
| ▷ Physical Therapy | ▷ 04:30 pm | 🗑 |
| ▷ Bed time | ▷ 10:00 pm | 🗑 |
| + | | |

Sidebar: Patient/ Room/ Warnings, Home Screen, Patient Dashboard, Timeline, Medication & Schedule, Live Data, Labs & Imagery, Patient's Questions

FIG. 9L

DISPLAY LAYOUT AND INTERACTIVE OBJECTS FOR PATIENT MONITORING

CROSS REFERENCE TO PRIORITY APPLICATIONS

Any and all applications for which a foreign or domestic priority claim is identified in the Application Data Sheet as filed with the present application are hereby incorporated by reference under 37 CFR 1.57. This application claims the benefit of priority to U.S. Provisional Patent Application No. 62/923,248, filed Oct. 18, 2019 and entitled "DISPLAY LAYOUT AND INTERACTIVE OBJECTS FOR PATIENT MONITORING," and to U.S. Provisional Patent Application No. 63/017,151, filed Apr. 29, 2020 and entitled "DISPLAY LAYOUT AND INTERACTIVE OBJECTS FOR PATIENT MONITORING." All the foregoing are hereby incorporated by reference in their entireties herein.

BACKGROUND

The present disclosure relates to display layouts and interactive objects for a physiological patient monitoring system.

In a hospital setting, often minor oversights can turn into fatal mistakes. Many of these oversights are due to the fact that healthcare professionals are constantly inundated with large amounts of information. It is difficult, if not impossible, to stay completely abreast of each patient's progress and procedures, and hospital charts often indiscriminately list information without indication of which pieces of information are the most critical for patient care. Thus, there is a need for more intuitive and streamlined modes of conveying patient information to healthcare professionals.

SUMMARY

For purposes of summarizing the disclosure, certain aspects, advantages and novel features are discussed herein. It is to be understood that not necessarily all such aspects, advantages, or features will be embodied in any particular embodiment of the invention and an artisan would recognize from the disclosure herein a myriad of combinations of such aspects, advantages or features.

The disclosure describes a physiological patient monitoring system with a healthcare professional-facing interface. The healthcare professional interface may communicate critical patient information to hospital staff in quick and concise, yet clear, ways. Due to the sensitive nature of patient information, the healthcare professional interface may only display by default the most critical non-confidential patient information. To access the full range of features in the system, in some configurations, the hospital staff may be required to unlock the device via entering a personal identification number ("PIN"), entering a password, scanning a Radio Frequency Identification ("RFID") chip, or any other method of automated secure access. Once unlocked, hospital staff can access all of a patient's treatment history, and much or all data may be consolidated and presented intuitively such that the care team member can quickly catch up on the patient's progress before entering the room to speak with the patient.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure.

FIGS. 3A-3F are illustrative interfaces showing patient physiologic measurements, according to some embodiments.

FIGS. 5A and 5B are illustrative interfaces showing real-time updates to the patient's vitals, according to some embodiments.

FIG. 6A-6F are illustrative interfaces displaying a patient's lab results, according to some embodiments.

FIGS. 7A-7D are illustrative interfaces showing a patient's medication details and daily schedule, according to some embodiments.

DETAILED DESCRIPTION OF THE PREFERRED EMBODIMENT

The current hospital system is riddled with opportunities for minor oversights to turn into fatal mistakes. Such opportunities arise because information is not presented in easily accessible methods that busy healthcare professionals can quickly and easily digest. Critical patient data is often buried under hundreds of pages of paperwork, and physicians often rush to skim patient charts while chatting with the patient. The presently disclosed healthcare professional interface of a physiological patient monitoring system addresses the issue of inaccessible information by consolidating the most key pieces of patient information and presenting the information in an intuitive manner. By clearly presenting critical patient information to healthcare professionals, the present system can reduce errors that can cost patients their lives.

Figure 1:
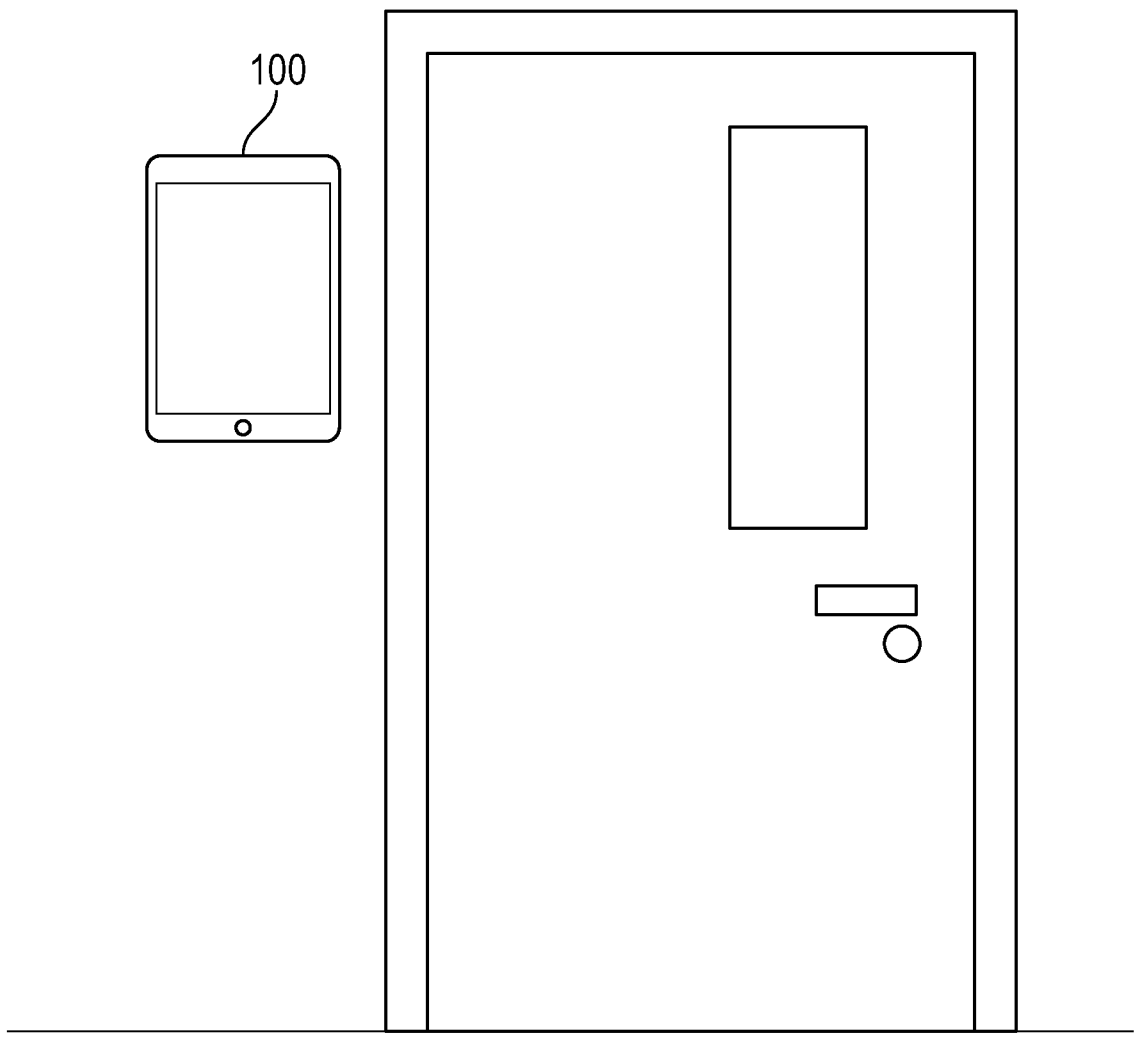
FIG. 1 depicts a portable device with a healthcare professional interface for a physiological patient monitoring system mounted outside a hospital room.

FIG. 1 depicts a portable device 100 with the healthcare professional interface of a physiological patient monitoring system mounted or otherwise placed on the wall outside a hospital room. The interface may display medical information for one or more patients occupying the hospital room. In some configurations, the portable device 100 may be in close proximity to the hospital room, though not mounted on the wall. For example, the portable device may be placed on a device-holding stand next to the door of the hospital room. The portable device may be secured in a way that allows easy removal from the surface to which it is secured. For example, the portable device 100 may be placed in a bin mounted on the wall, held in place by a hook and loop fasteners, clasped, or any other method of securing the portable device in a set position while also allowing relatively easy removal. In other configurations, the portable device 100 may be secured such that the device 100 may only be removed by authorized healthcare administrators. For example, the device 100 may be stored in a locked bin or locked onto a device stand, where the locking mechanism may be mechanically or electronically controlled. In configurations with mechanical locks, only approved healthcare providers may be allowed to have possession of the key. In configurations with electronic locks, the lock may automatically unlock when an approved provider approaches the device 100 (for example, through use of an RFID tag, Wi-Fi triangulation, or other known location techniques) or may be manually unlocked via a password, PIN, biometric identification measures, etc. In yet other configurations, the portable device may be located at a nurse station or carried by a healthcare provider. The placement of the portable device may allow physicians and other hospital staff to review critical information about a patient before entering the patient's room. The current predominant system relies on physical printouts of such information, and key information can be lost in the middle of hundreds of pages of paperwork. Having the most critical information posted outside of a patient's room can reduce the chances of medical staff overlooking critical information.

To protect patient privacy, the device 100 may be configured to dim or completely darken the screen in certain situations. In some configurations, the portable device may have its screen completely darkened when the device is not in use. The screen display may be activated by touching the screen or a button on the device 100. In other configurations, the portable device's screen display may automatically turn on when a healthcare provider approaches the patient's room. This can be done by an RFID tag, Wi-Fi triangulation, or other known location techniques. In some configurations, the device screen may dim after a pre-determined period of time without detected use or motion, such that passersby may not see private patient data if a physician leaves the device unattended. In other configurations, the device may automatically lock after a pre-determined period of time without detected use or motion. In yet other configurations, the device 100 may automatically lock upon being returned to its assigned mounting location. In yet other configurations, the device 100 may be manually locked by the healthcare provider after using it. In some configurations, the device 100 may include an alarm system to alert hospital staff that the device 100 was not replaced to its assigned area. The alarm system may be triggered after a pre-determined period of time away from its assigned area and without detected used. The alarm system may generate an audible noise from the device 100, or it may ping other electronic devices associated with hospital staff members.

Figure 2A:
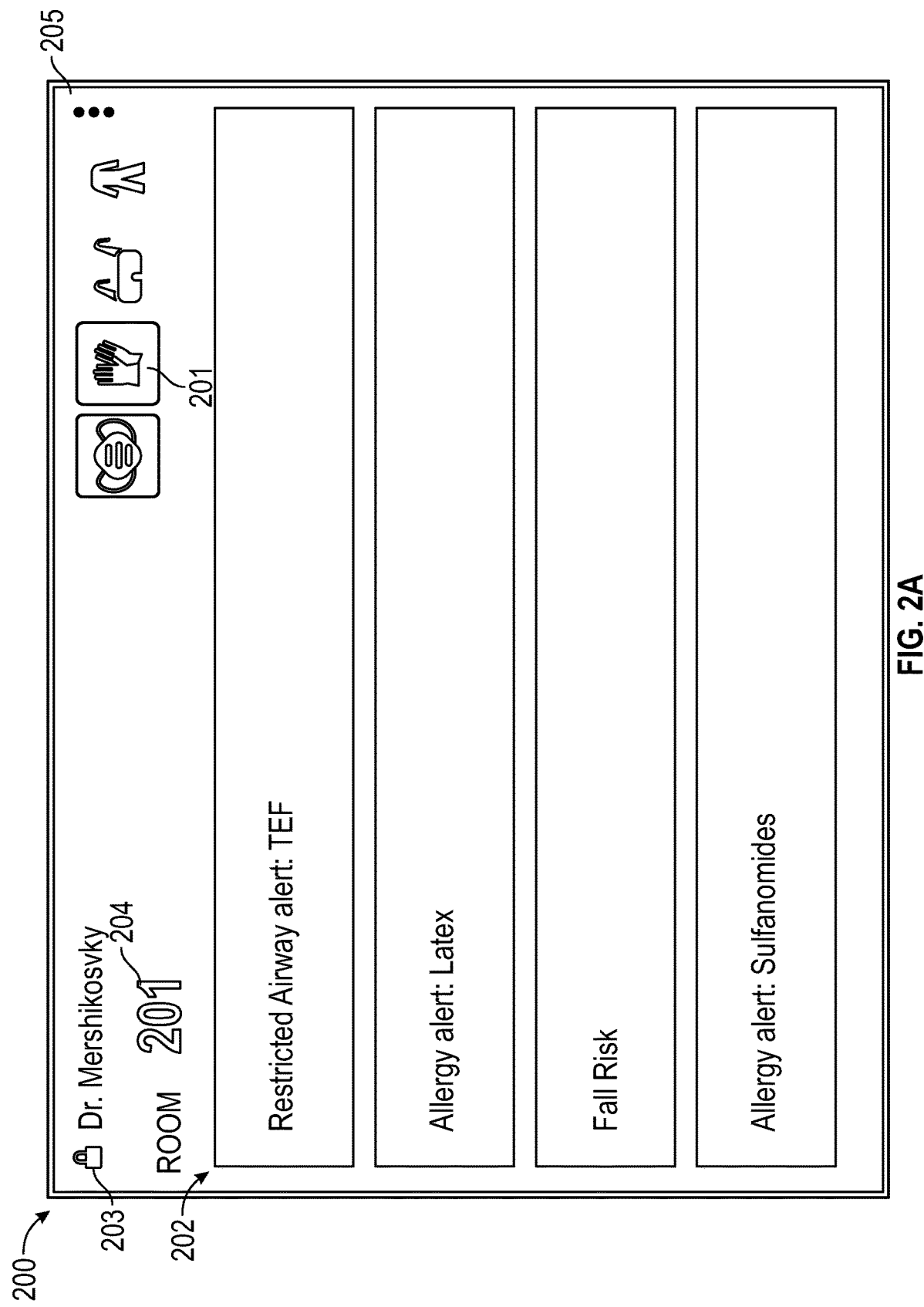
FIGS. 2A-2M are illustrative interfaces for a default screen showing critical, non-confidential patient information, according to some embodiments.
Figure 2B:
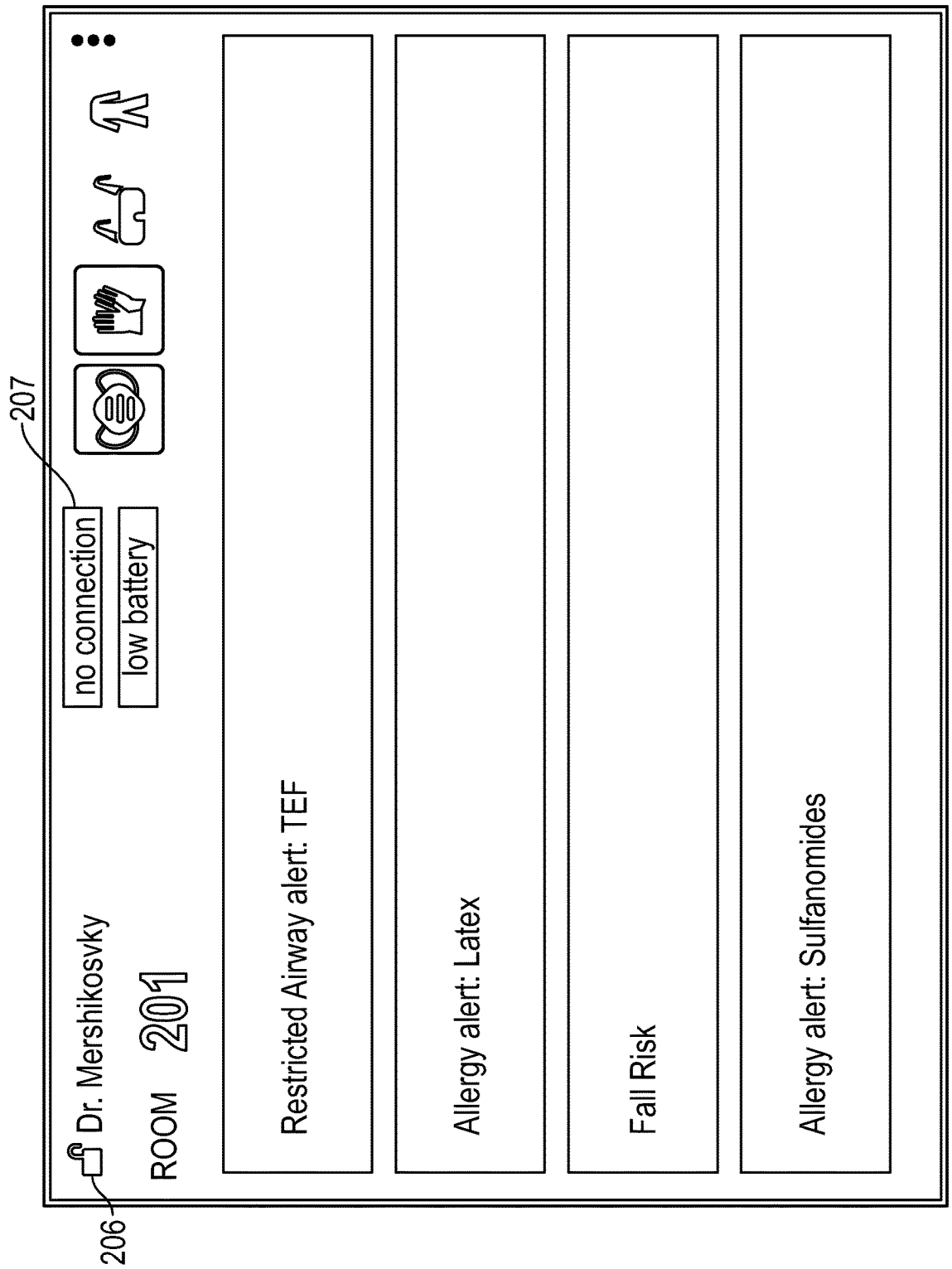
Figure 2C:
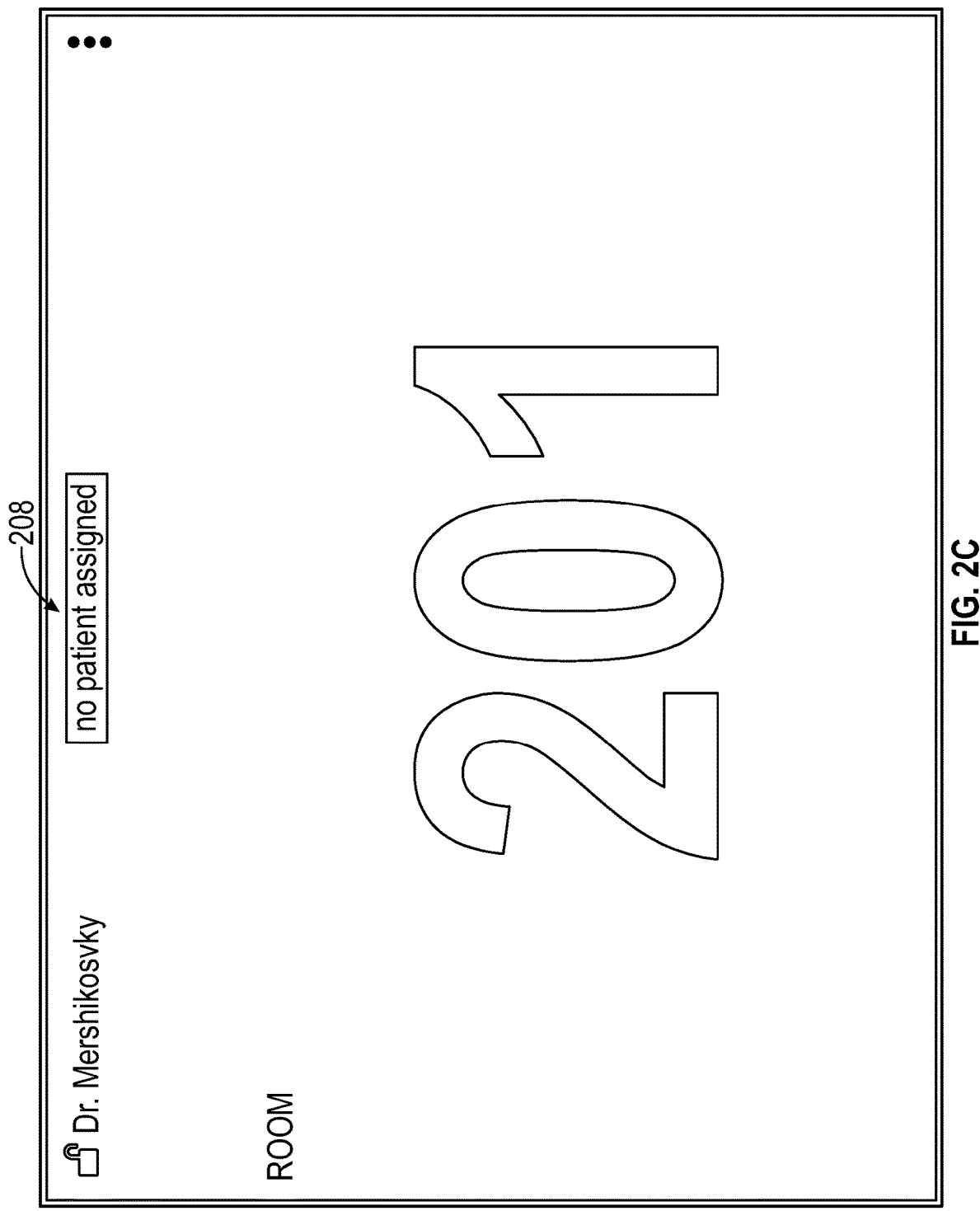

The physiological patient monitoring system may be connected to patient monitoring equipment and a hospital data network. The healthcare professional interface may thus be updated with live measurements, safety precautions, and lab results. The healthcare professional interface may also connect to other systems integrated in the hospital. For example, hospital rooms may be equipped with a ceiling-mounted display configured to display different types of health parameters, emergency notifications, and safety precaution measures. The healthcare professional interface may be in communication with the ceiling-mounted display such that the display shows certain data from the interface. In some configurations, the display may show the default screen 200 of the healthcare professional interface (FIGS. 2A-2C). In other configurations, the display may show any screen from the healthcare professional interface. In yet other configurations, the display may only receive data from the healthcare professional interface, then generate a different illustration by applying different color schemes for different types of health parameters or health parameter values. For example, the color red may be used to indicate health parameter values that are out of a predetermined range, while the color green may be used to indicate health parameter values that are within the predetermined range. In another example, different physiological parameters can be assigned different colors. For example, blood pressure readings may be in green while temperatures readings may be in red. The display can also use different color schemes for notifications indicating different patient conditions. For example, the display may generate and display notifications and/or parameter readings in red during emergency situations. On the other hand, the display may generate and display notifications and/or parameter readings in green or no color in normal situations. The display may always be on, or the display may only turn on when the associated portable device 100 turns on. Updates to both the healthcare professional interface and ceiling-mounted display may occur continuously, automatically, only when new data is manually entered, or any combination of these methods.

FIGS. 2A-C illustrate one example of a default screen 200 for a hospital staff interface for portable devices located outside of a hospital room. As shown in FIG. 2A, the default screen 200 may list safety precautions 201 and critical patient information 202. The safety precautions 201 may warn clinicians to use certain personal protective equipment, including, but not limited to, gloves, eyewear, and masks. Critical patient information 202 may include, but is not limited to, severe allergies, other medical conditions, and other potential risks of harm. To protect sensitive patient information, only non-HIPAA (Health Insurance Portability and Accountability Act) protected information may be displayed on the default screen 200, and the interface may remain locked when the device is not in use. The interface can be unlocked via entering a personal identification number ("PIN"), entering a password, scanning a Radio Frequency Identification ("RFID") chip, or any other method of automated secure access. Once unlocked, the device can display further details in the patient's medical file. The default screen 200 may include a lock status icon 203 so users can easily recognize if an interface is locked or unlocked. The default screen 200 may identify the hospital room 204 for which patient data is being displayed. The default screen 200 may also include a settings menu 205, described in greater detail below in relation to FIGS. 23A-P, where the clinician can select which information to display and customize the interface. FIG. 2B shows the default screen 200 after a clinician has logged in. The screen may show an updated lock status icon 206, which may indicate that the interface is unlocked and which clinician is logged in. The default screen 200 may further display device warnings 207, such as, but not limited to, low battery warnings or unstable connection warnings. FIG. 2C shows an illustrative default screen 200 when there is no patient assigned to the room and no patient data to display. In such a scenario, the default screen 200 may only display the hospital room 204 with which the device 100 is associated. The default screen 200 may further display a no-assignment notification 208. In some configurations, the device warnings 207 may be displayed on the default screen 200 at all times: before and after clinician login and regardless of patient assignment. In such configurations, the device warnings 207 would appear concurrently with the no-assignment notification 208.

Figure 2D:
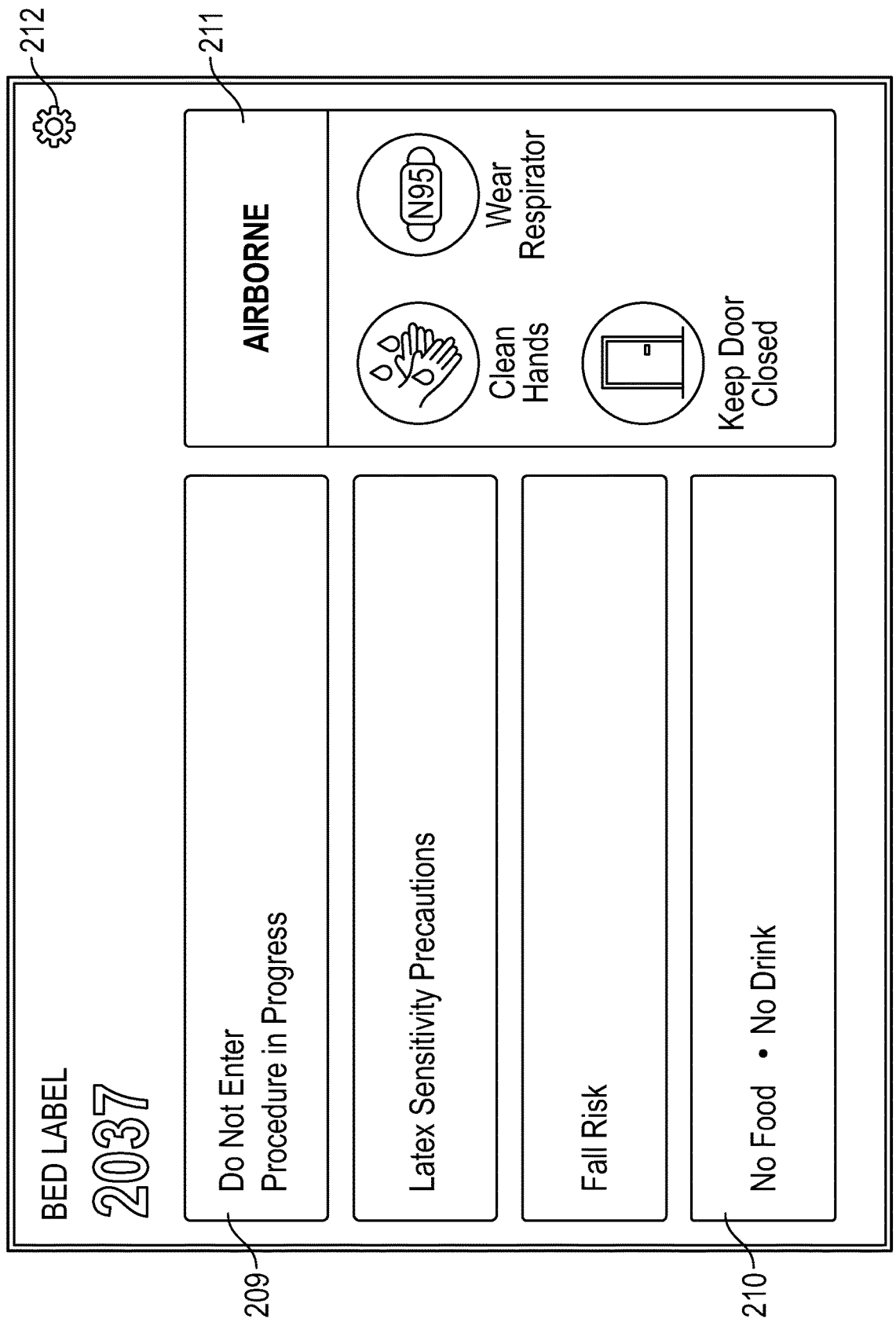

FIG. 2D illustrates another configuration of a default screen 200 for a hospital staff interface. As depicted, critical patient information 202 may further include procedure alerts 209 to prevent disturbance of the procedure. Critical patient information 202 may also include food and drink warnings 210. Food and drink warnings 210 may span beyond food allergies and may be necessary for patients preparing for procedures that require fasting beforehand. In this configuration, the default screen 200 may display the type of pathogen risk 211 present in the hospital room. Safety precautions 201 associated with prevention of the displayed type of pathogen risk 211 may then be listed. Critical patient information 202 may also include warnings for patients that need to be isolated (for example, highly contagious patients or patients who may be a safety risk to others). FIG. 2D also shows an alternative settings menu icon 212. The critical patient information 202 may be color-coded to reflect various parameters. For example, procedure alerts may be presented in red print or in a red color block as they act to prevent immediate patient harm and should be noticeable.

Figure 2E:
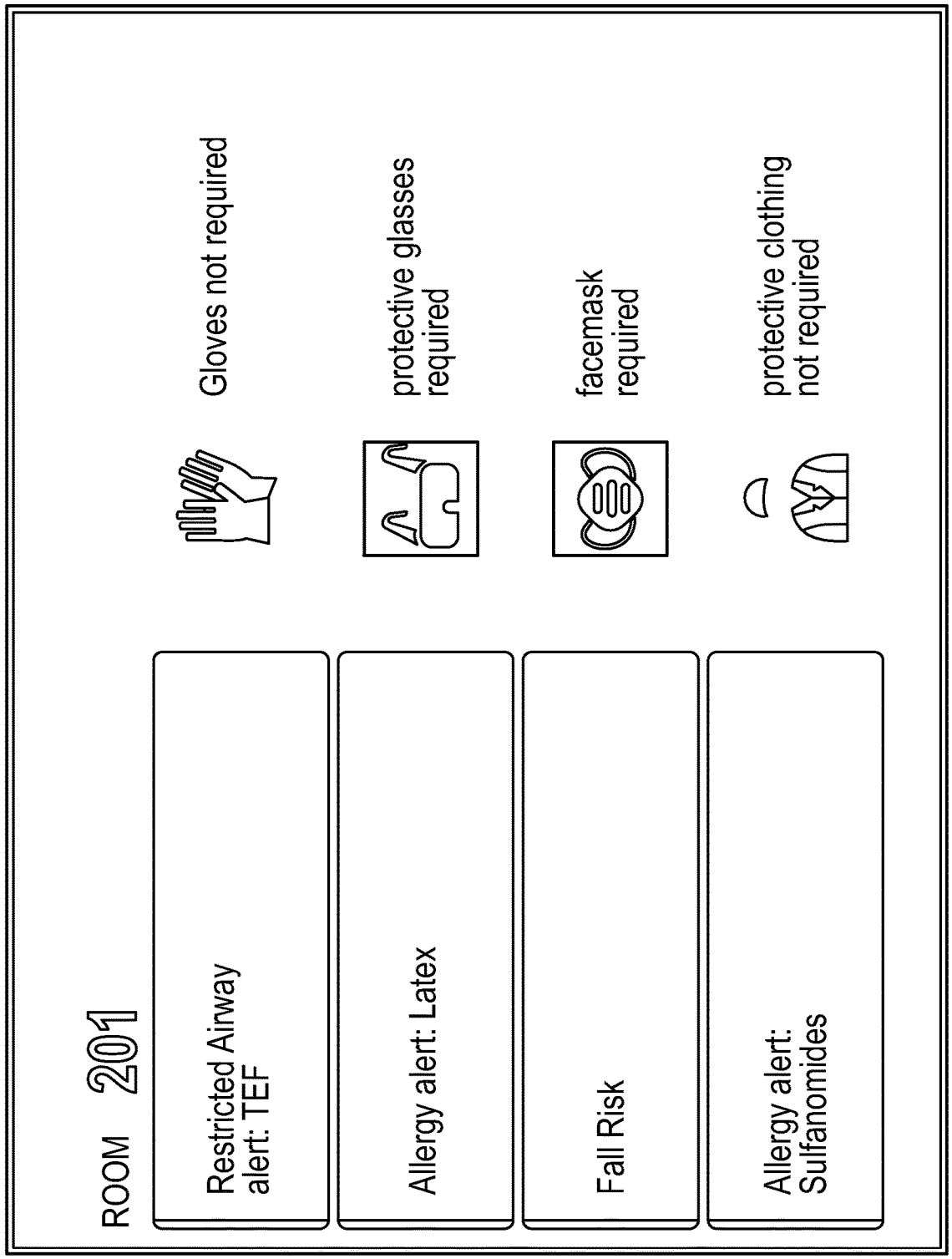
Figure 2F:
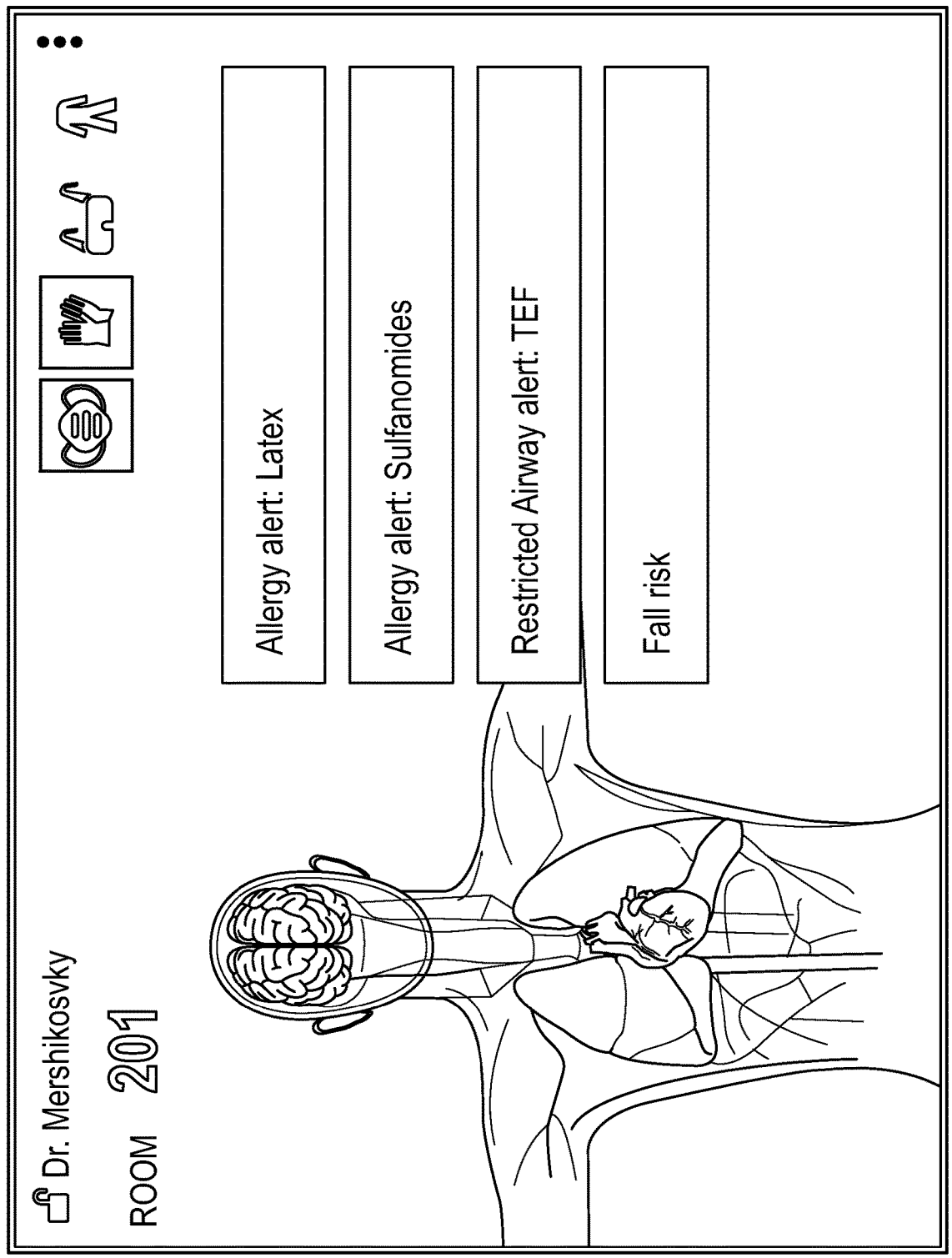
Figure 2G:
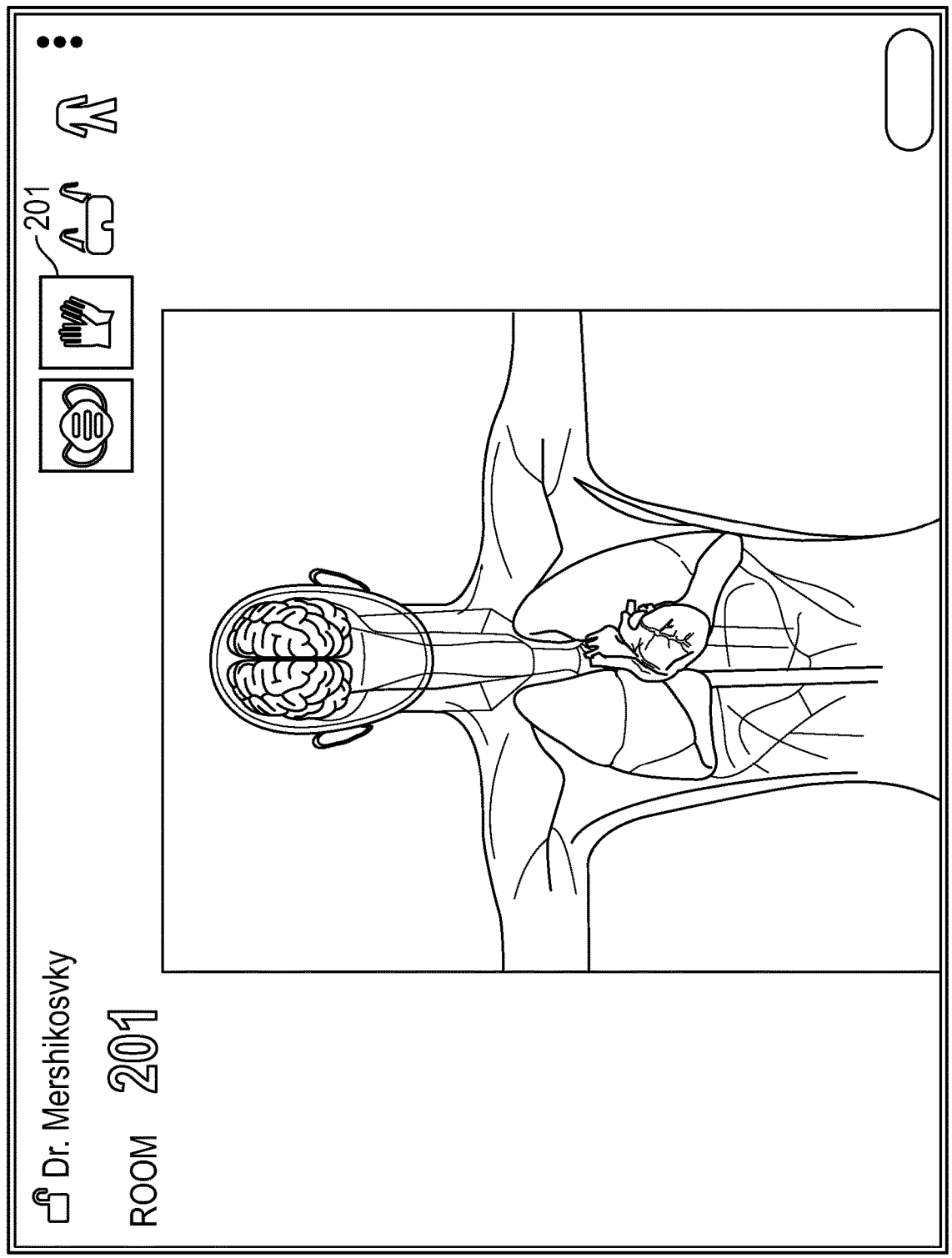

FIGS. 2E-G are other examples of default screens 200. FIGS. 2E and 2F show examples of default screens 200 when the device is associated with a patient. FIG. 2G shows an example of a default screen 200 when there is no patient in the assigned hospital room 204. Safety precautions 201 may be listed as necessary when there are no patients in the room. For example, the room may be left vacant for disinfecting purposes prior to admitting the next patient. In such situations, anyone entering the room may still require safety equipment and other precautionary preparation. In other configurations, the default screen 200 may not show safety precautions 201 when there are no patients in the hospital room 204.

Figure 2H:
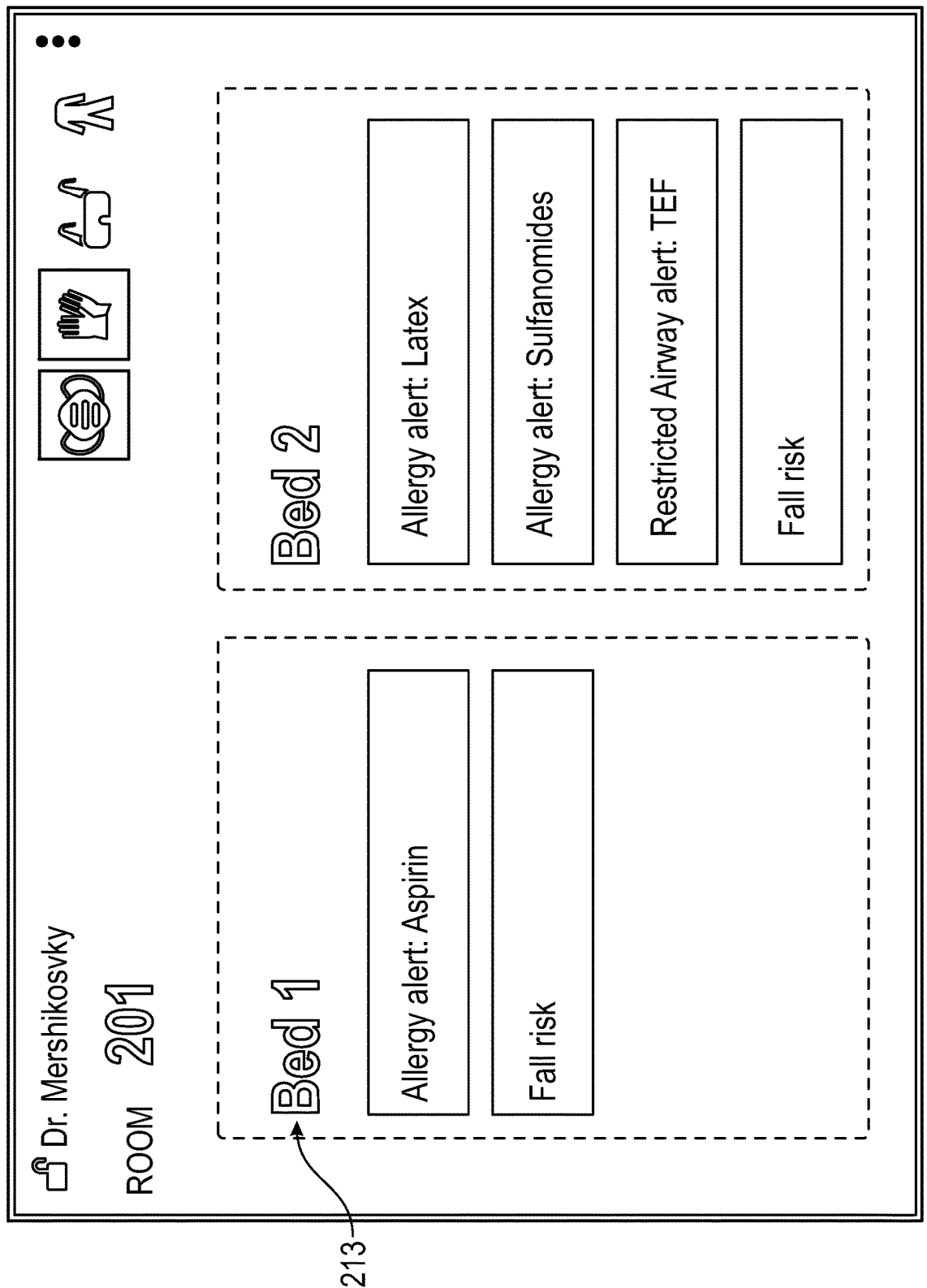
Figure 2I:
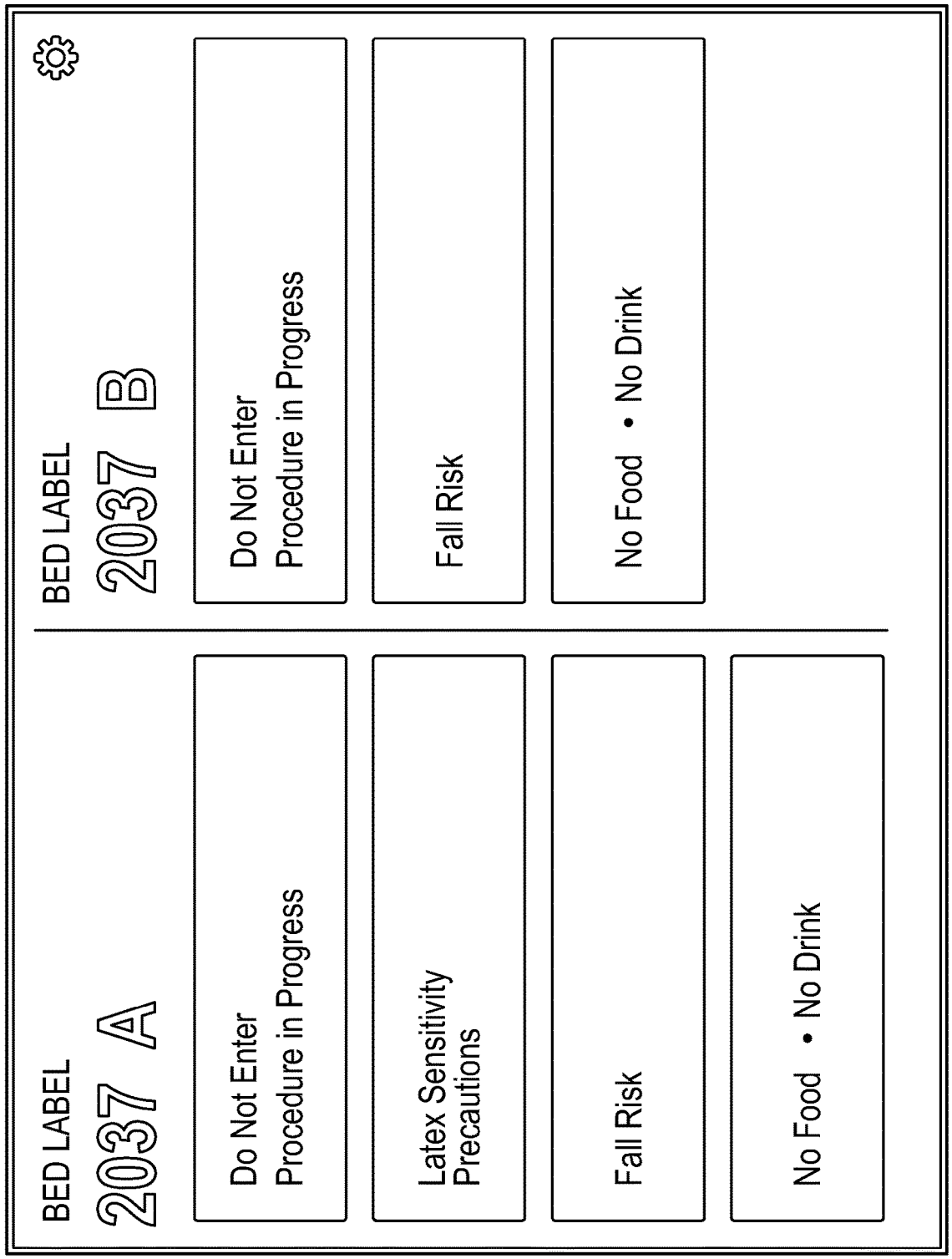
Figure 2J:
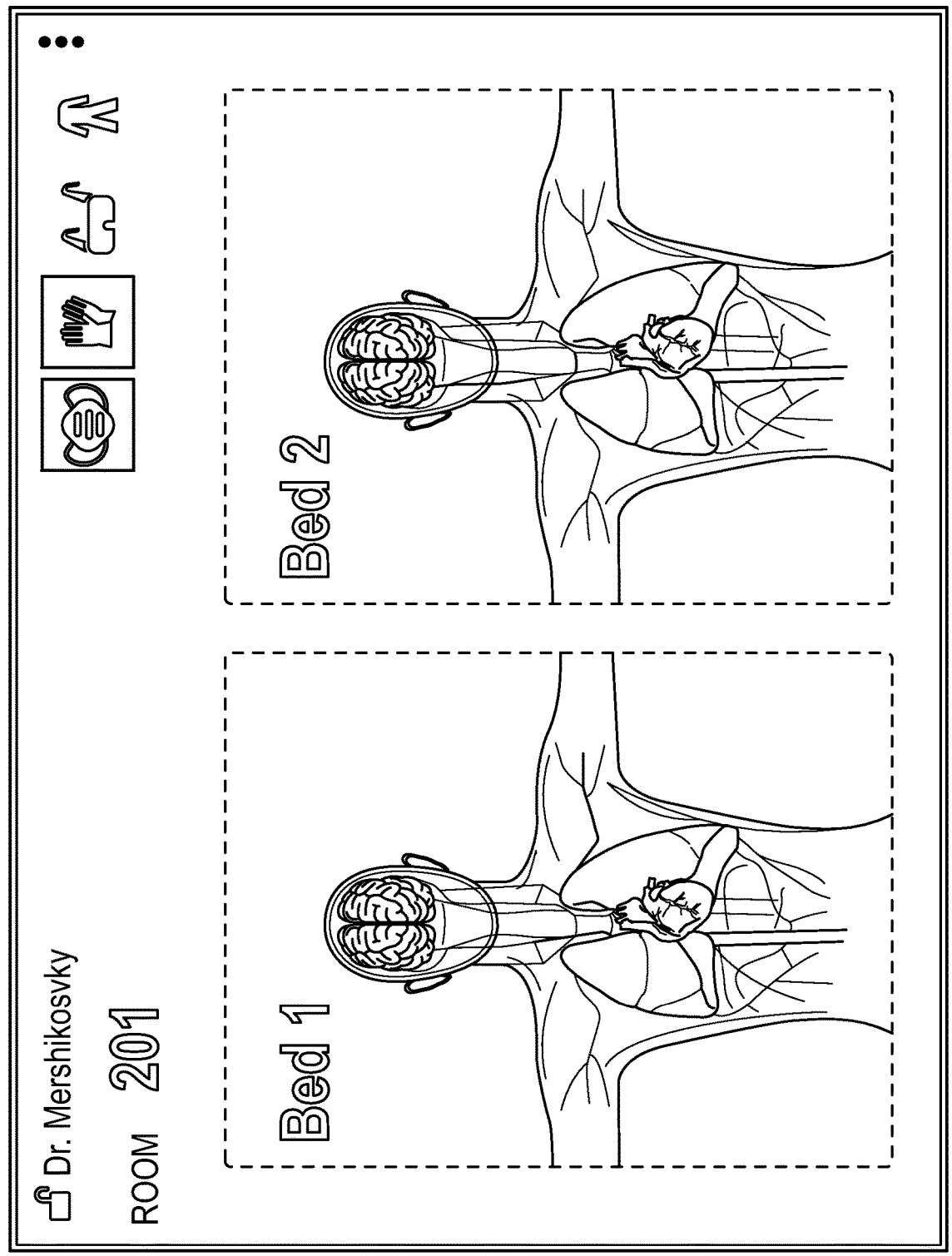
Figure 2K:
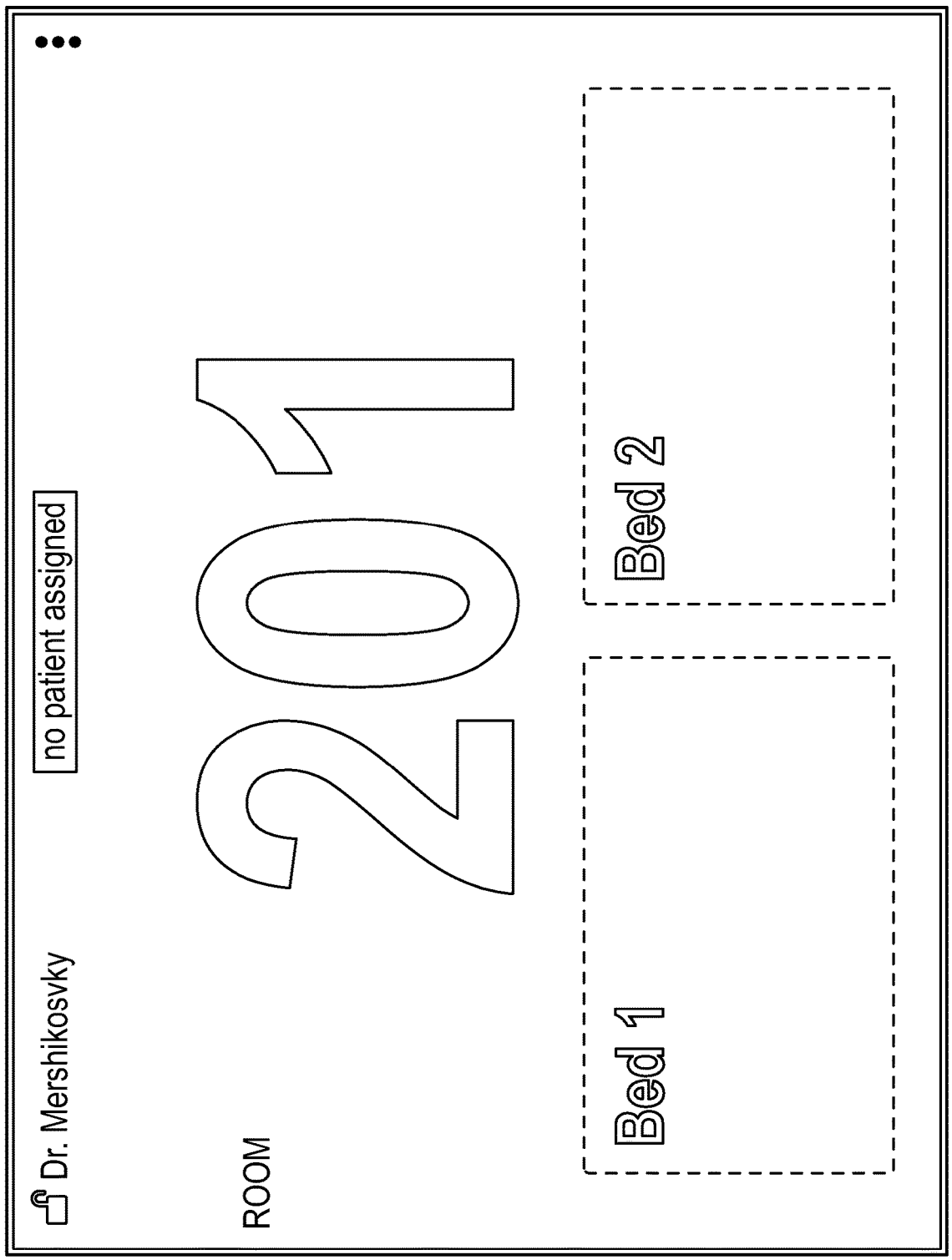

FIGS. 2H-K illustrate another example default screen 200 in which there are two beds in the hospital room associated with the interface. FIGS. 2H and 2I show that the double-bed configurations may display all the same features as a single-bed default screen. The double-bed configurations may further display a bed number 213 for each bed in the room. Each patient's critical patient information 202 may be listed in association with the patient's bed number 213. FIGS. 2J and 2K show double-bed screens when no patients are assigned to the hospital room 204. The double-bed configurations without patient assignments may display all the same features as a single-bed default screen that has no patient assignment.

Figure 2L:
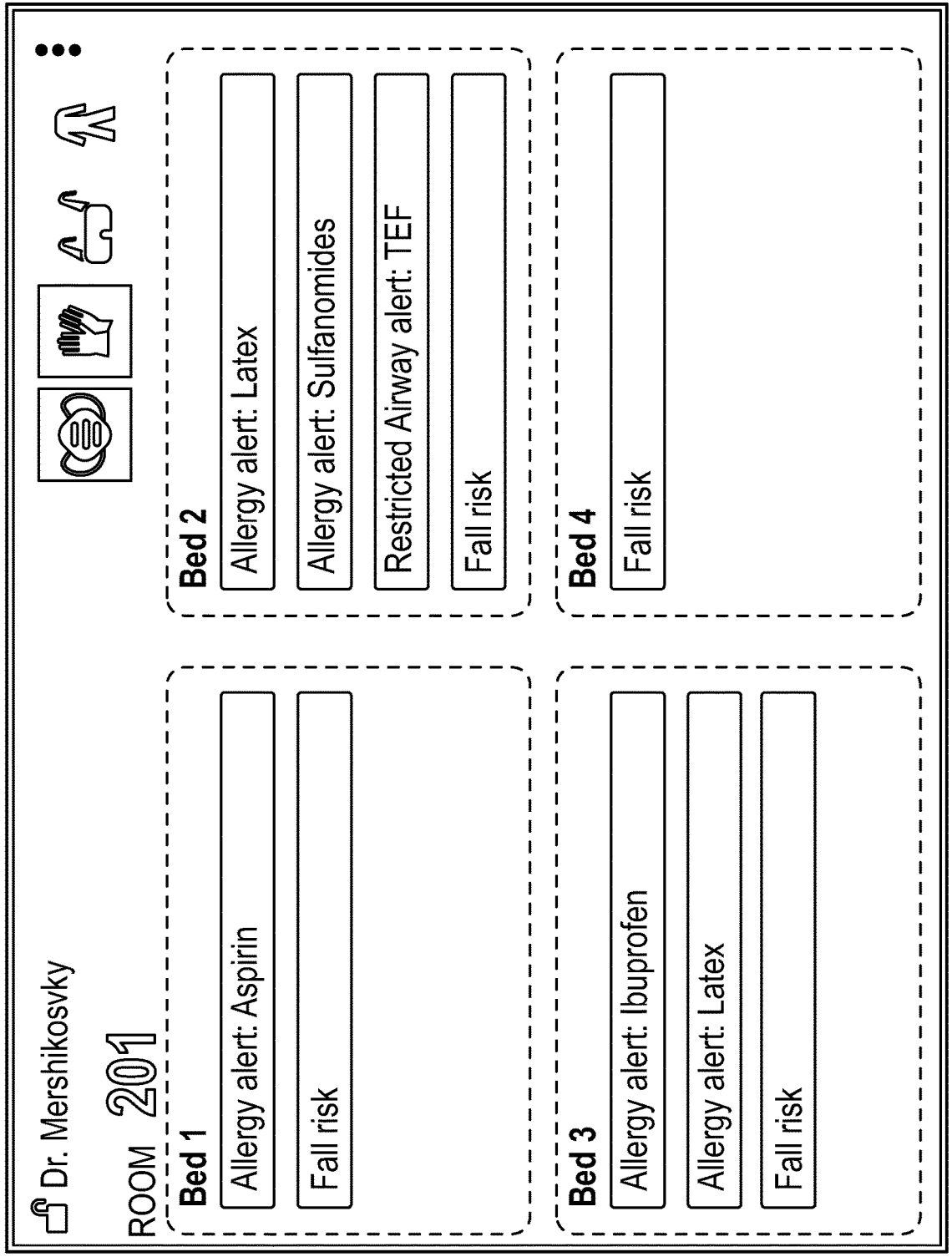
Figure 2M:
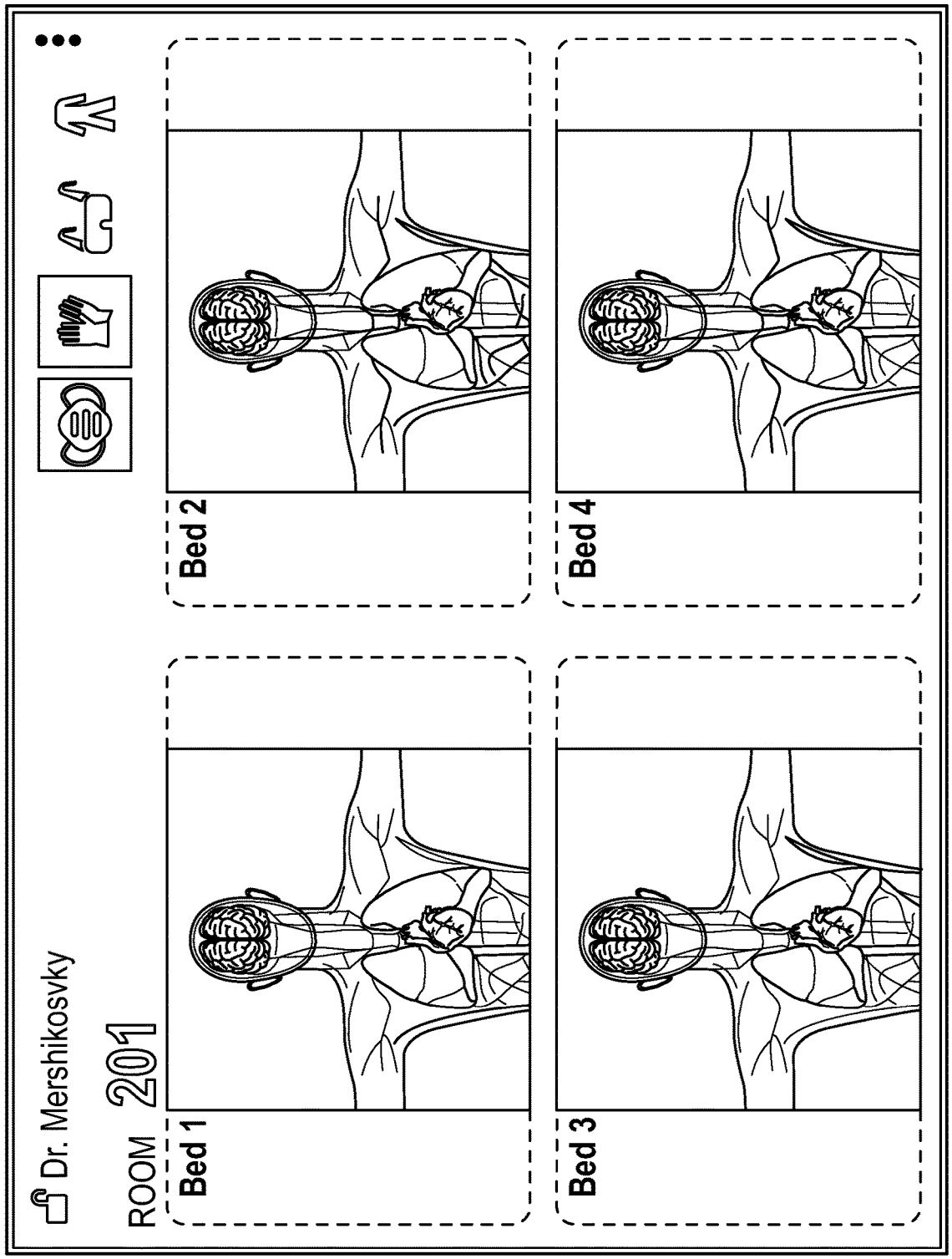

FIGS. 2L and 2M illustrate another configuration of a default screen 200 in which there are four beds in the hospital room associated with the interface. FIG. 2L shows that the quadruple-bed configurations may display all the same features as a one-bed default screen. Each patient's critical patient information 202 may be listed in association with the patient's bed number 213. FIG. 2M shows quadruple-bed screens when no patients are assigned to the room. The quadruple-bed configurations without patient assignments may display all the same features as a single-bed default screen that has no patient assignment. Accordingly, the same features are displayed for each individual patient, regardless of the number of beds in the hospital room to which the device is paired.

With reference to FIGS. 2A-M, it should be noted that the safety precautions 201 may be selected manually and/or automatically generated. In some configurations, healthcare professionals may select the default screen safety precautions 201 via one or more settings pages, such as those illustrated in FIGS. 9A-P. In some configurations, the safety precautions 201 may be automatically generated by the physiological patient monitoring system, based at least partly on the patient's data. In some configurations the safety precautions 201 may by a combination of manually selected items and automatically generated items. For example, the physiological patient monitoring system may parse the patient's records for listed allergies to automatically display an allergy alert for the items, while the recommended safety equipment list may be selected by a healthcare professional. In some configurations, automatically generated safety precaution items may be manually overridden by healthcare professionals, via one or more settings pages, such as those illustrated in FIGS. 9A-P.

Figure 2N:
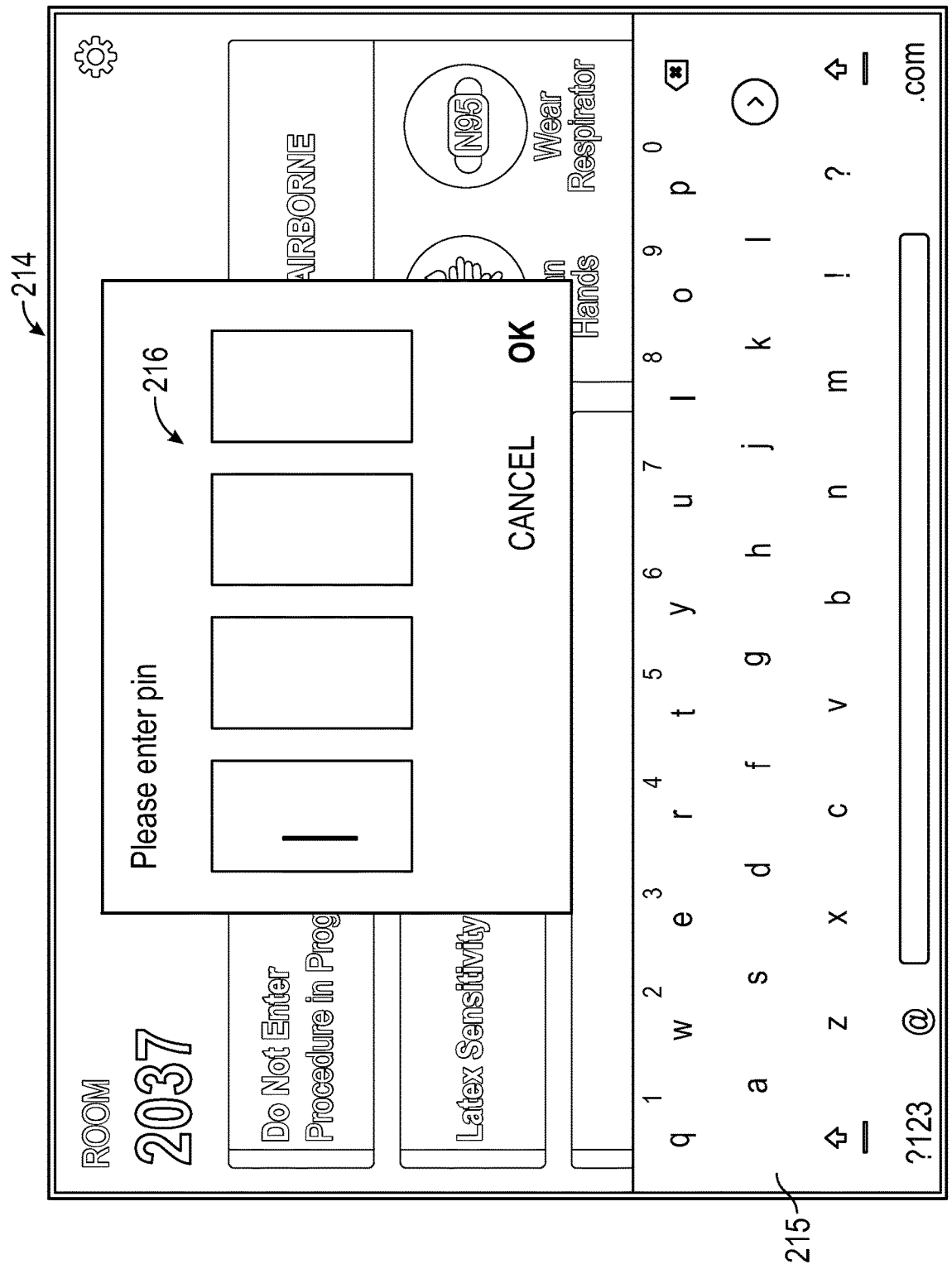
FIG. 2N is an illustrative interface for a passcode input screen from which healthcare providers may access the digital patient file, according to some embodiments.

FIG. 2N is an illustrative unlock screen 214. The unlock screen 214 may accept a PIN input to unlock the patient file. A virtual keyboard 215 may appear on the lock screen such that the user can enter a passcode. The unlock screen 214 may include a passcode display area 216 such that the user can see the inputted values. In some configurations, the passcode display area 216 may censor the values so that the passcode cannot be accidentally seen by un-intended audiences. In such configurations, the unlock screen 214 may provide an option to reveal the inputted values. It should be understood that the depicted passcode display area 216 is merely illustrative and that the passcode may be comprised of any symbols, characters, or digits and may be any length. In other configurations, the unlock screen 214 may require entering a password, scanning an RFID chip, or any other method of automated secure access. In some configurations that use card-scanning methods of secure access, the unlock screen 214 may only contain instructions to scan the card and may not contain a virtual keyboard 215 or a passcode display area 216. In other configurations that accept card scans, the unlock screen 214 may still have a passcode display area 216, but the passcode values may automatically fill once the card scans. In yet other emodiments, the unlock screen 214 may accept either manually entered passcodes or automatically-filled card scan passcodes, and may have a virtual keyboard 215 and a passcode display area 216 to support both features. Once unlocked, the staff member can navigate the application through a control panel 305, described in further detail in relation to FIG. 3A.

FIGS. 3A-E show illustrative examples of a Patient Dashboard 300, which may only be accessed after the application is unlocked. The Patient Dashboard 300 may act as a default screen when the application is unlocked. In some configurations, the Patient Dashboard 300 may not be the default screen after the application is unlocked. In such cases, the Patient Dashboard 300 may be accessed via the control panel 305.

Figure 3A:
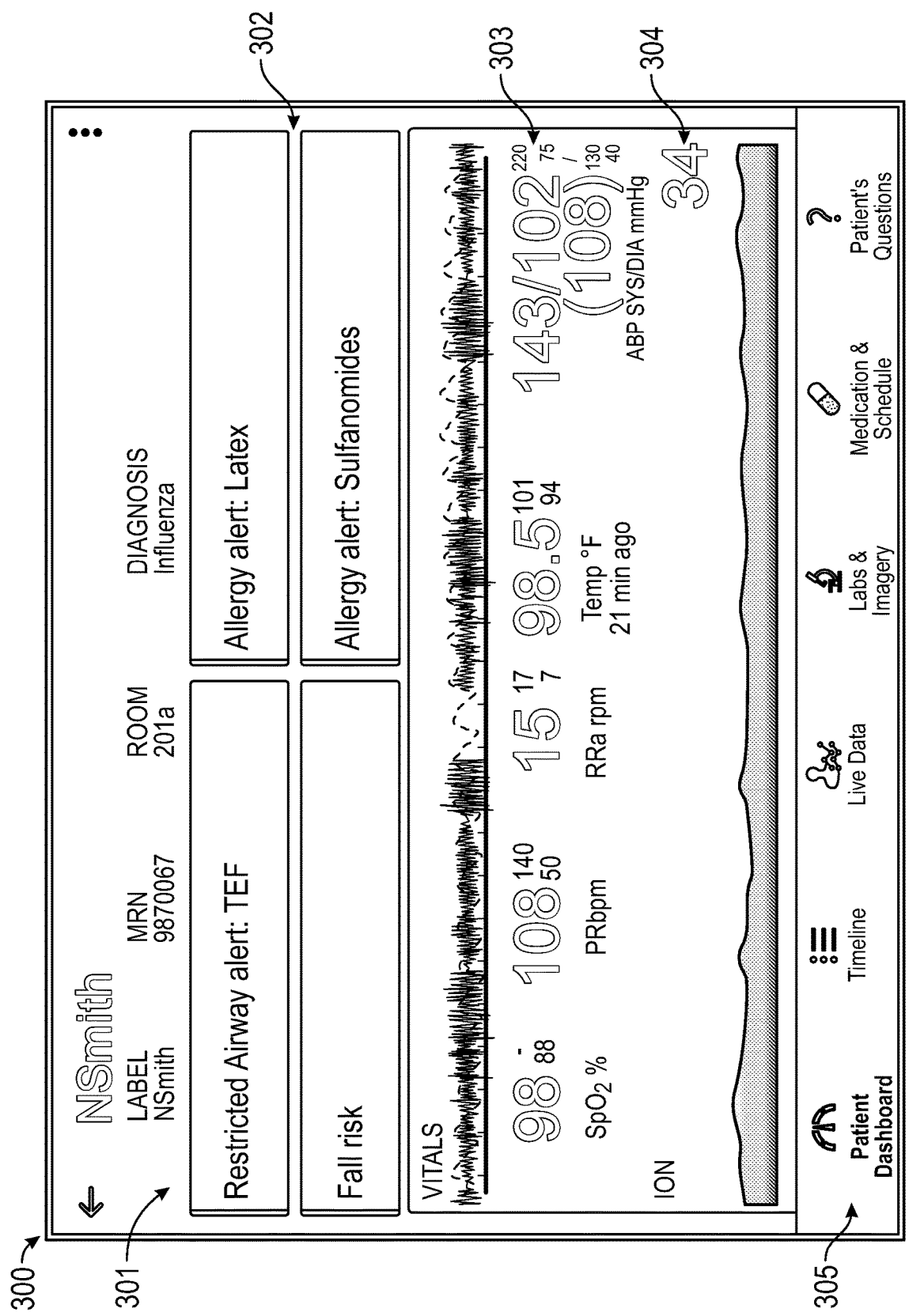
Figure 3B:
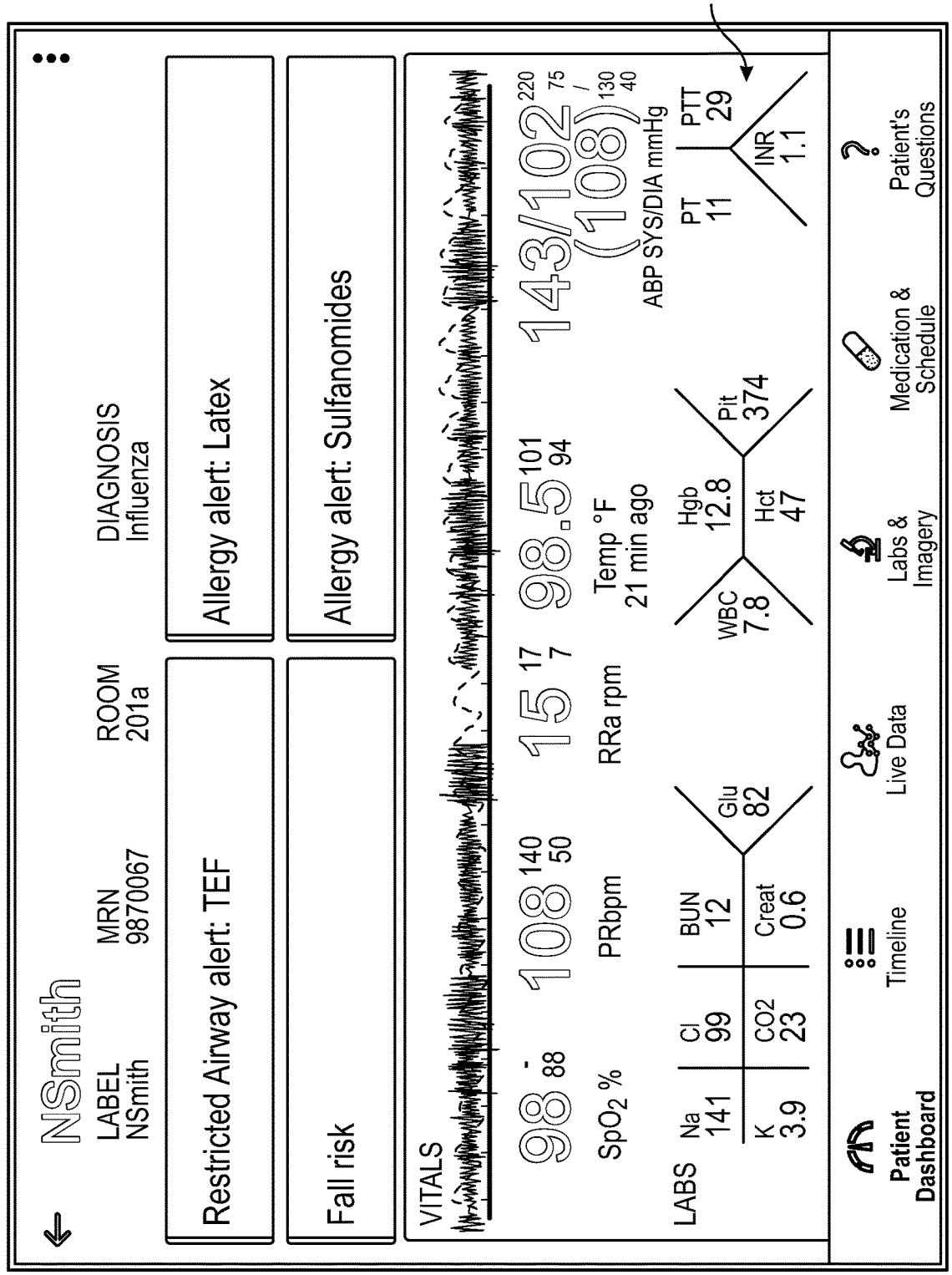
Figure 3E:
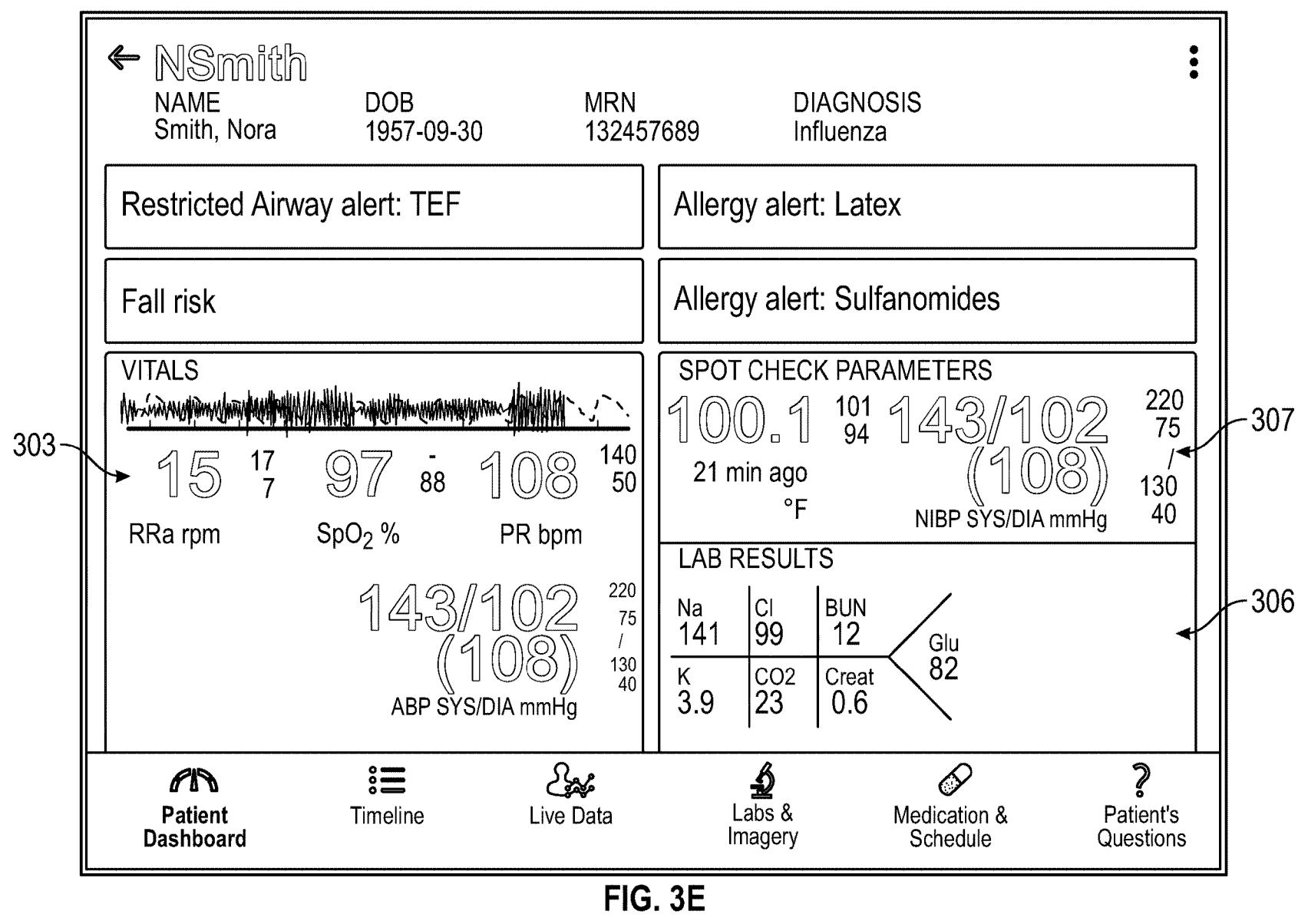

According to FIG. 3A, the Patient Dashboard 300 may list basic patient information 301, the critical information 302 from the lock screen, the patient's vitals 303, the patient's health score 304, and a control panel 305. The health score 304 may be a holistic measurement of the patient's health status. The health score 304 calculation may be based on any number of factors, including, but not limited to pulse rate, oxygenation saturation, perfusion index, or any other factors as selected by the healthcare staff. Basic patient information 301 may include, but is not limited to, patient name, age, medical record number, room and bed number, diagnosis, and other such information which a healthcare provider may need to initial interaction with the patient. FIG. 3B illustrates an alternative configuration of the Patient Dashboard 300 in which the patient's lab results 306 may be shown instead of the health score 304. In some configurations, the lab results 306 may be presented in a fishbone diagram or other visual representation that is easy for healthcare professionals to review. FIG. 3C illustrates another alternative configuration of the Patient Dashboard 300 in which the patient's spot check parameters 307 may be displayed rather than the health score 304 or lab results 306. Spot check parameters 307 may be any combination of patient vitals which a healthcare professional measured during the patient's most recent spot check. FIG. 3D is yet another configuration of the Patient Dashboard 300 which may display patient vitals 303 and spot check parameters 307 in a different layout. FIG. 3E is an illustration of the Patient Dashboard 300 in which patient vitals 303, lab results 306, and spot check parameters 307 may all be displayed. Indeed, the Patient Dashboard 300 display may be comprised of any combination of the aforementioned features and patient information. The information displayed on the Patient Dashboard may typically be the background information that medical professionals need before starting a deeper diagnosis. Presently, physicians obtain this information by skimming through a patient's charts while conversing with the patient in the room. Such multi-tasking increases the risk that the physician will overlook critical pieces of information. With the present disclosure, the physician can quickly obtain all the relevant background information before entering the room and may not need to multi-task.

FIG. 3F is an example Patient Dashboard 300 when no patient file is associated with the device, the device is not connected to the hospital network, or any other reason the device cannot receive data updates. In such a case, the Patient Dashboard 300 may display a no connection warning 308 and a missing data warning 309.

Figure 4A:
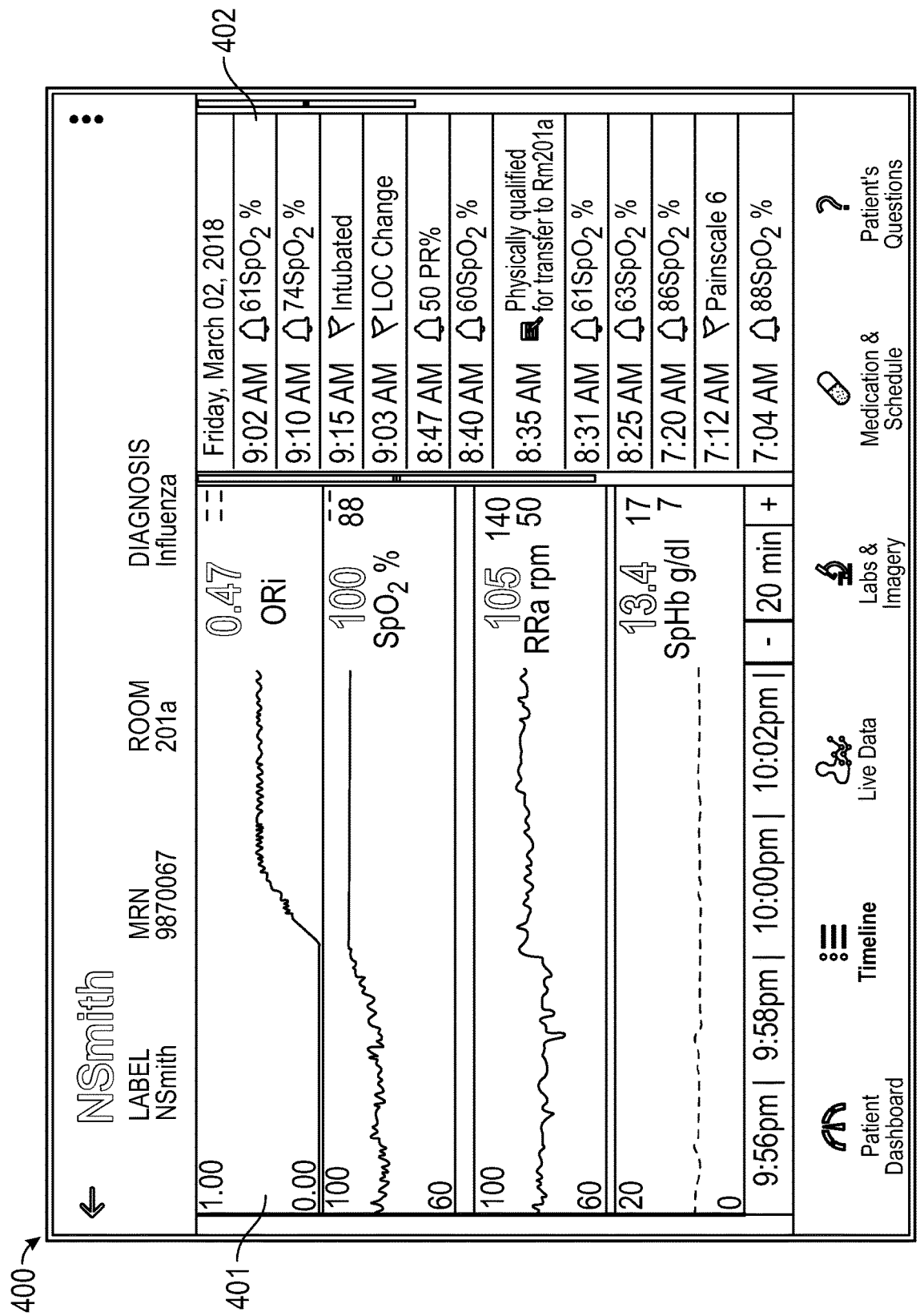
FIGS. 4A-4C are illustrative interfaces for tracking patient progress and medical procedures over time, according to some embodiments.
Figure 4B:
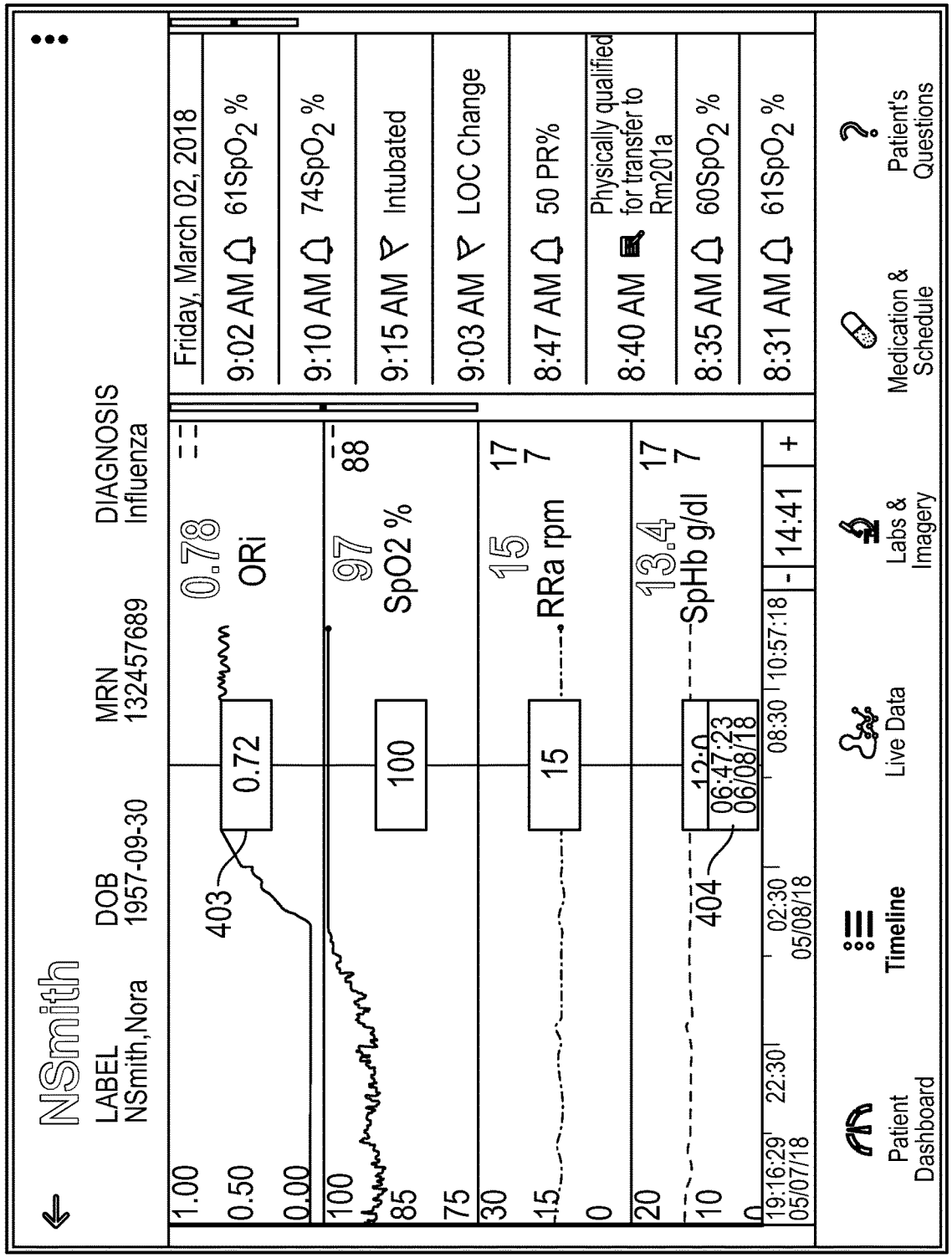
Figure 4C:
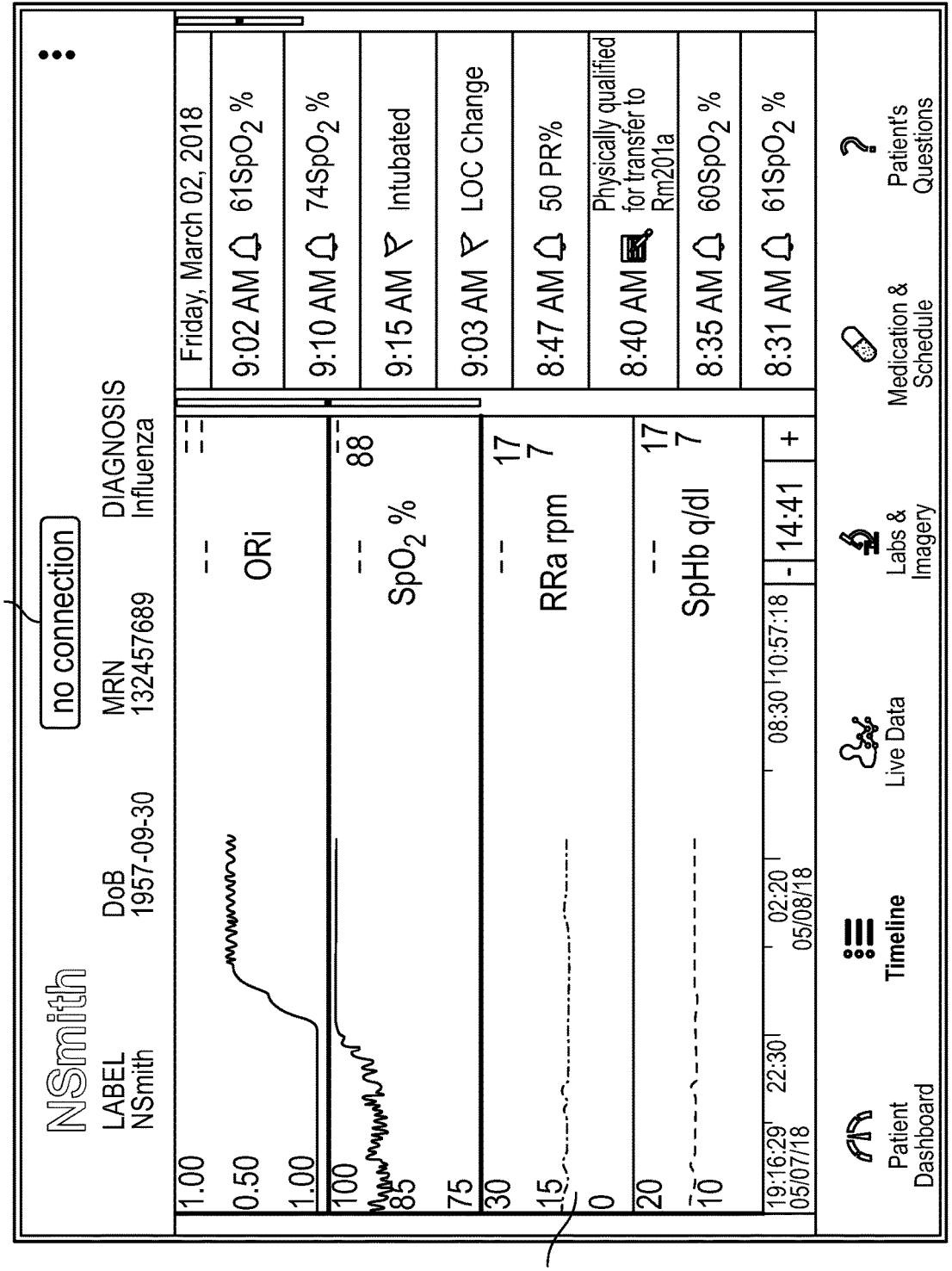

FIGS. 4A-C illustrate an example Timeline screen 400. The Timeline screen 400 may be accessed via the control panel 305. As shown in FIG. 4A, the feature may track the patient's vitals over time and display the data in a graphical representation 401. The feature may also log changes in the patient's vitals and medical procedures performed on the patient, and may display them in a timestamped event timeline 402. A detailed log of events such as the event timeline 402 can help keep every hospital staff member up to date on patient progress and inform their medical decisions. FIG. 4B demonstrates a pinpointing feature. The Timeline feature may allow clinicians to select a particular point on the graphical representation 401 and view the data at that point. Upon selection of a point on the graphical representation 401, the feature may display the vital measurements 403 as well as the time and date 404 at which the measurements were taken. In some configurations, selecting a point on the graphical representation for one vital may automatically also bring up the measurements of all other vitals at that same point in time. FIG. 4C is an example Timeline screen 400 when the patient is disconnected from vitals-monitoring machines, the device loses connection to the hospital network, or any other reason the device may stop receiving data updates. In such cases, the Timeline screen 400 may display a no connection warning 406 and truncated graphical representations 405 which may show patient vitals up until the moment the device stops receiving data updates.

Figure 5A:
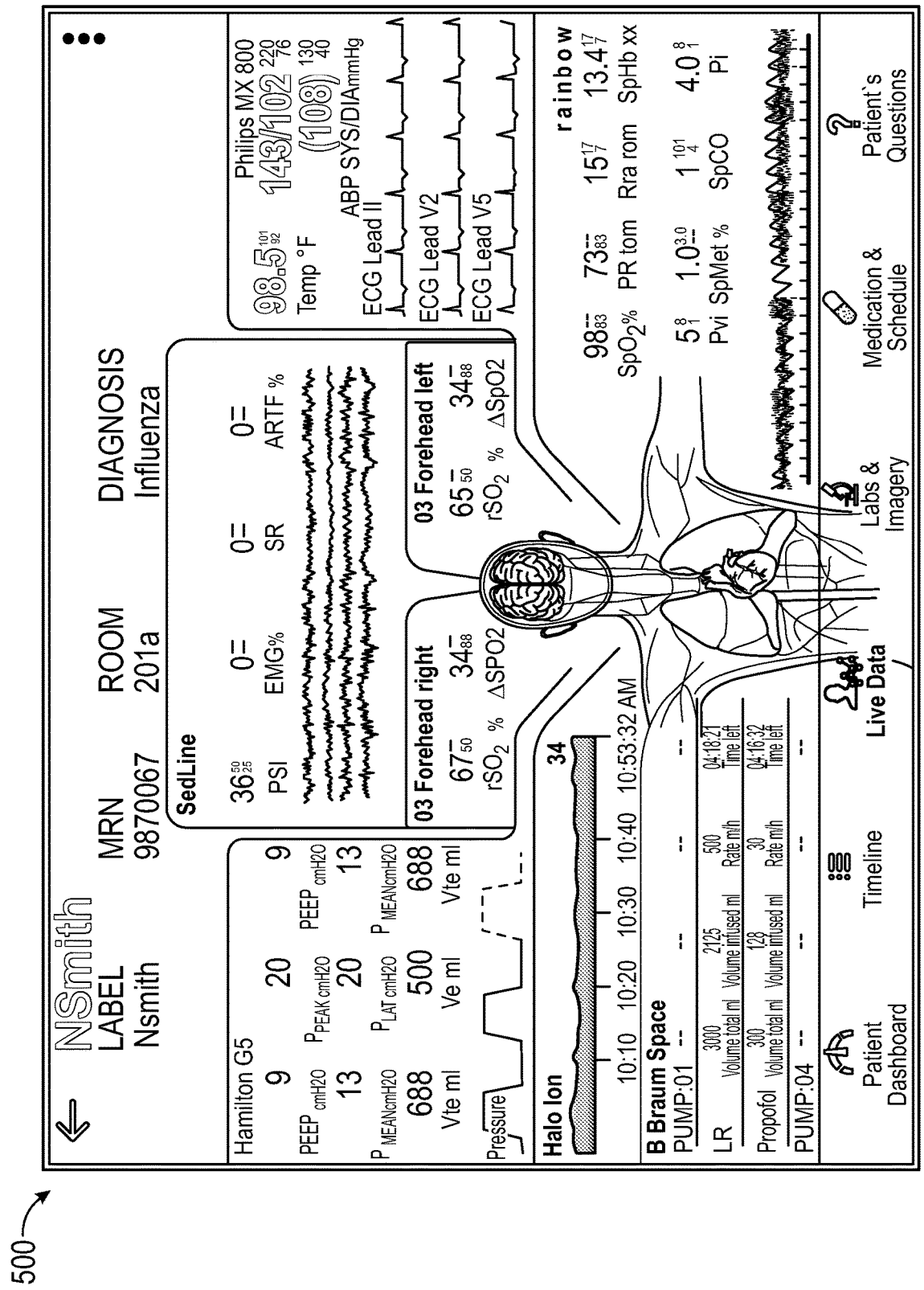
Figure 5B:
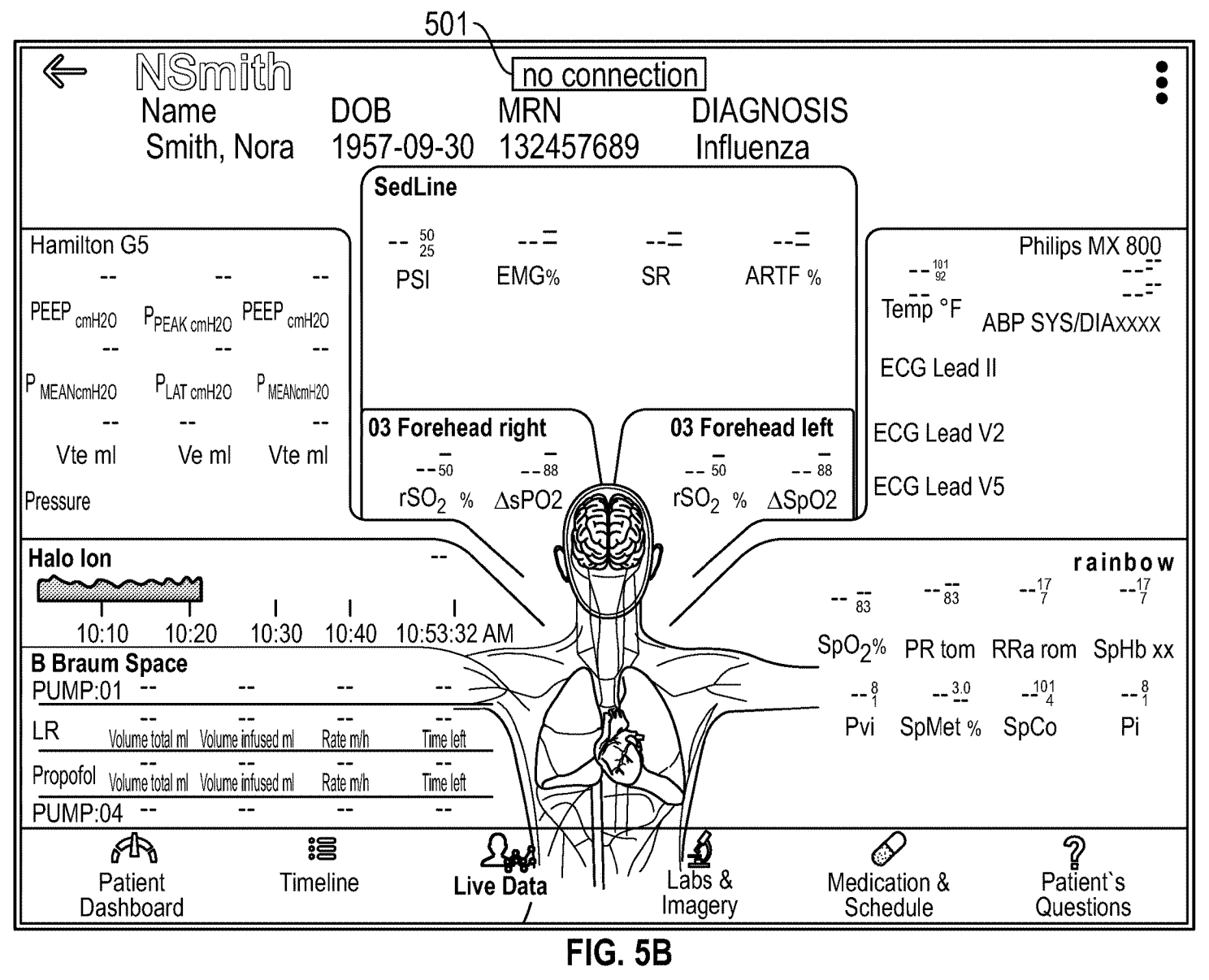

FIG. 5A illustrates an example Live Data screen 500, which may show real-time updates to the patient's vitals. The Live Data screen 500 may be accessed via the control panel 305. The Live Data screen 500 may be configurable to show any number of physiologic measurements, such as, but not limited to, basic patient information 301, patient vitals 303, patient health score 304, etc. FIG. 5B illustrates an example Live Data screen 500 when the patient is disconnected from vitals-monitoring machines, the device loses connection to the hospital network, or any other reason the device may stop receiving data updates. In such cases, the Live Data screen 500 may display a no connection warning 501. The screen 500 may indicate a lack of patient data by substituting dashes where physiologic measurements are usually listed, leaving the display space blank, or any other method of showing that the device is not receiving patient data.

Figure 6B:
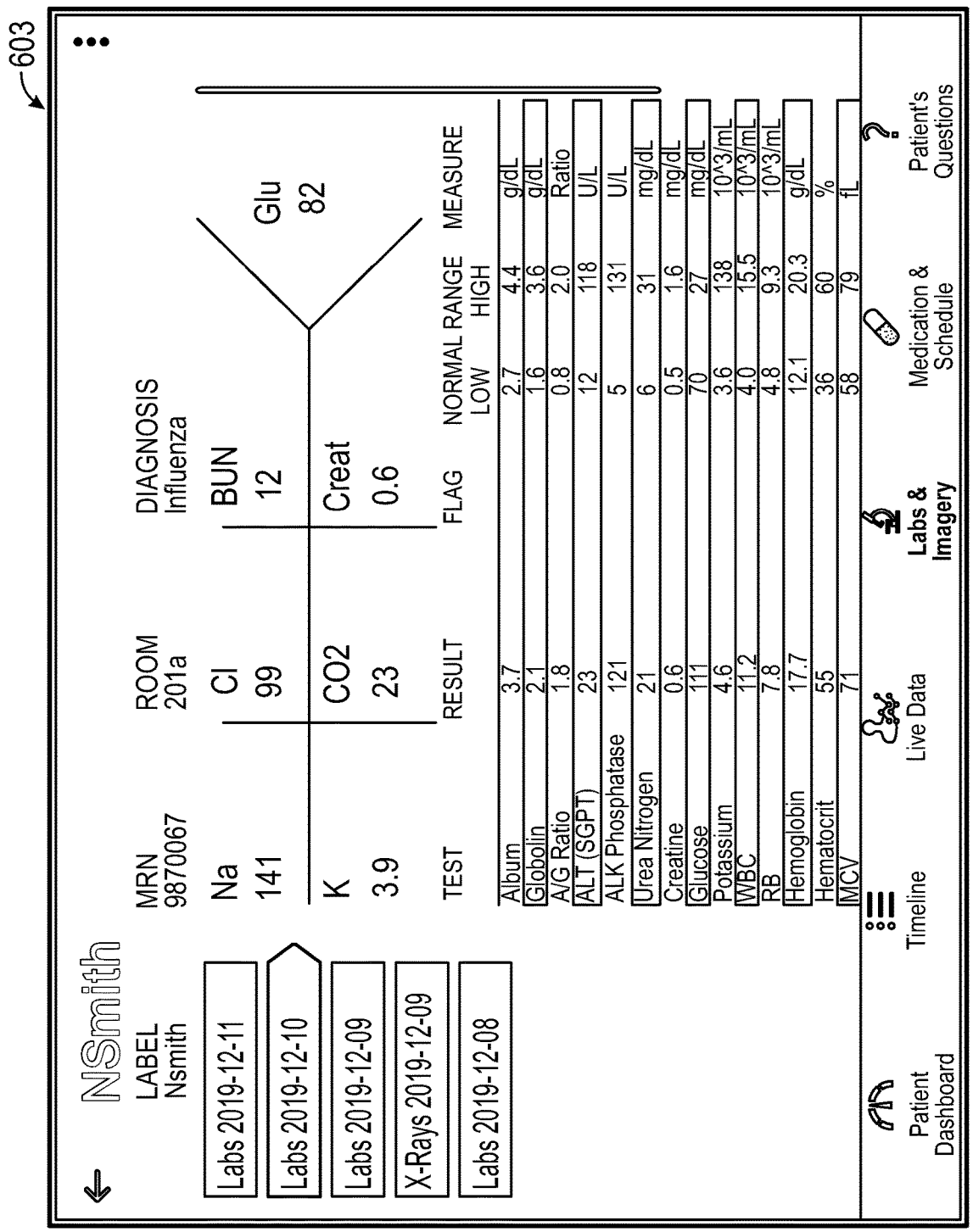
Figure 6D:
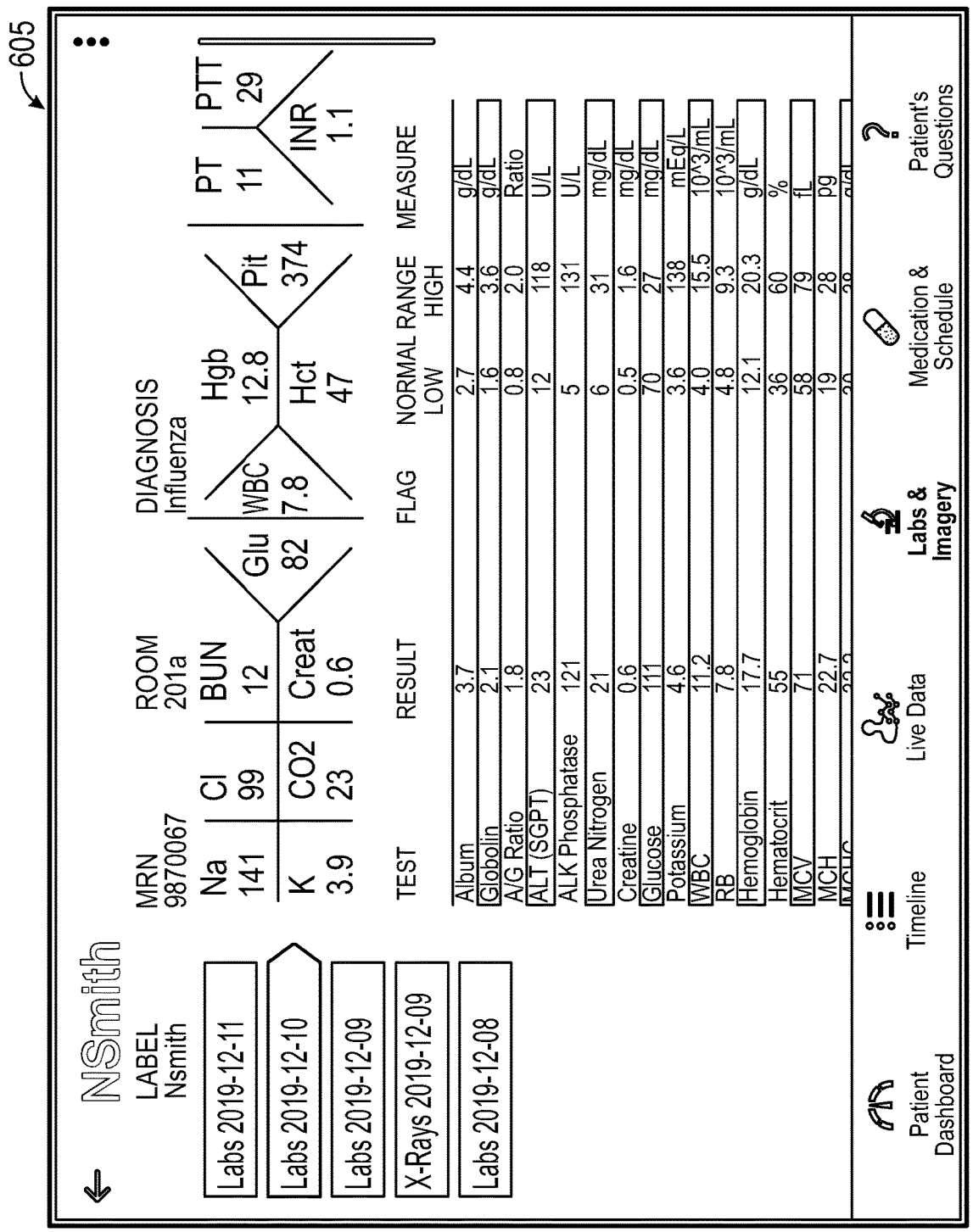
Figure 6E:
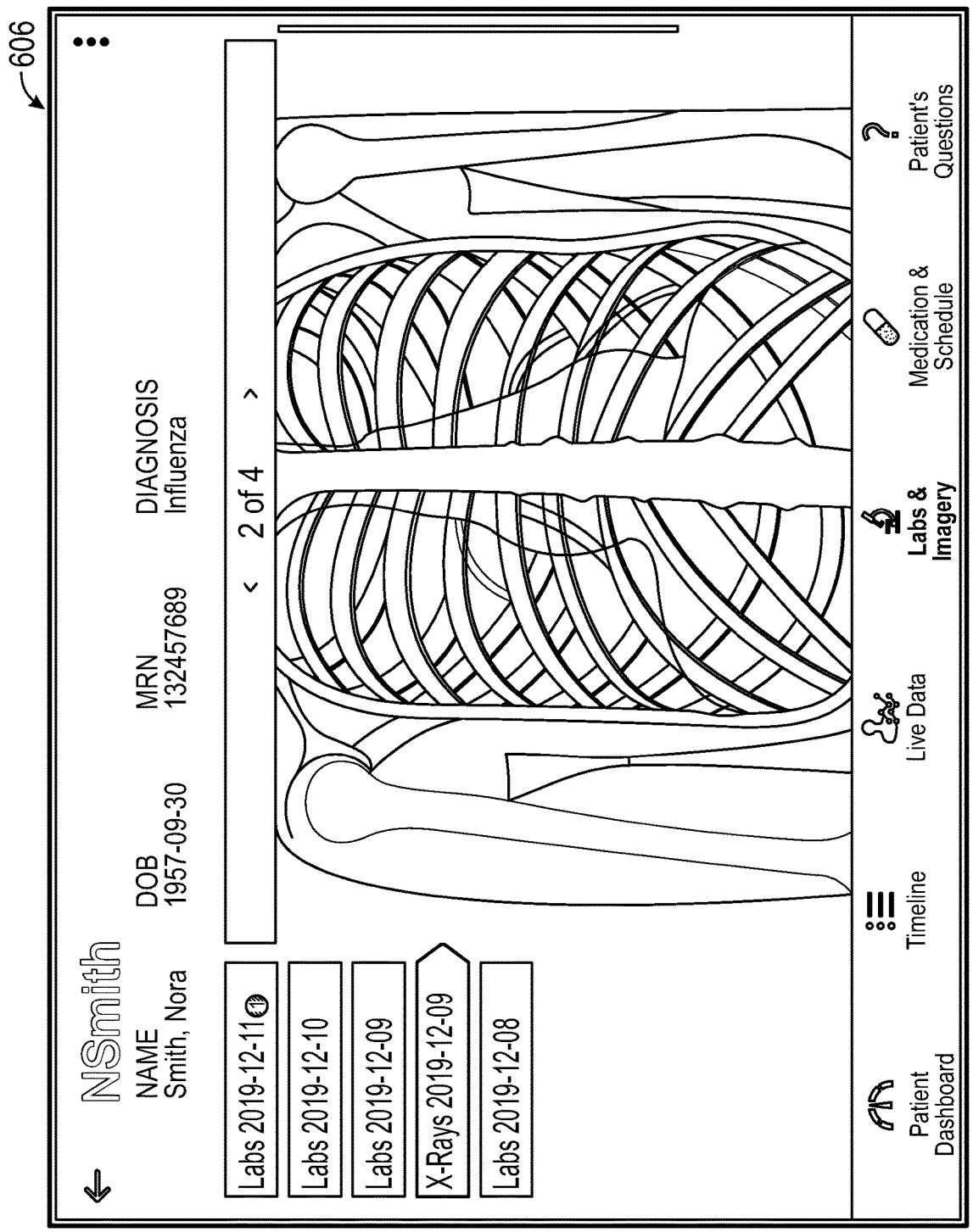
Figure 6F:
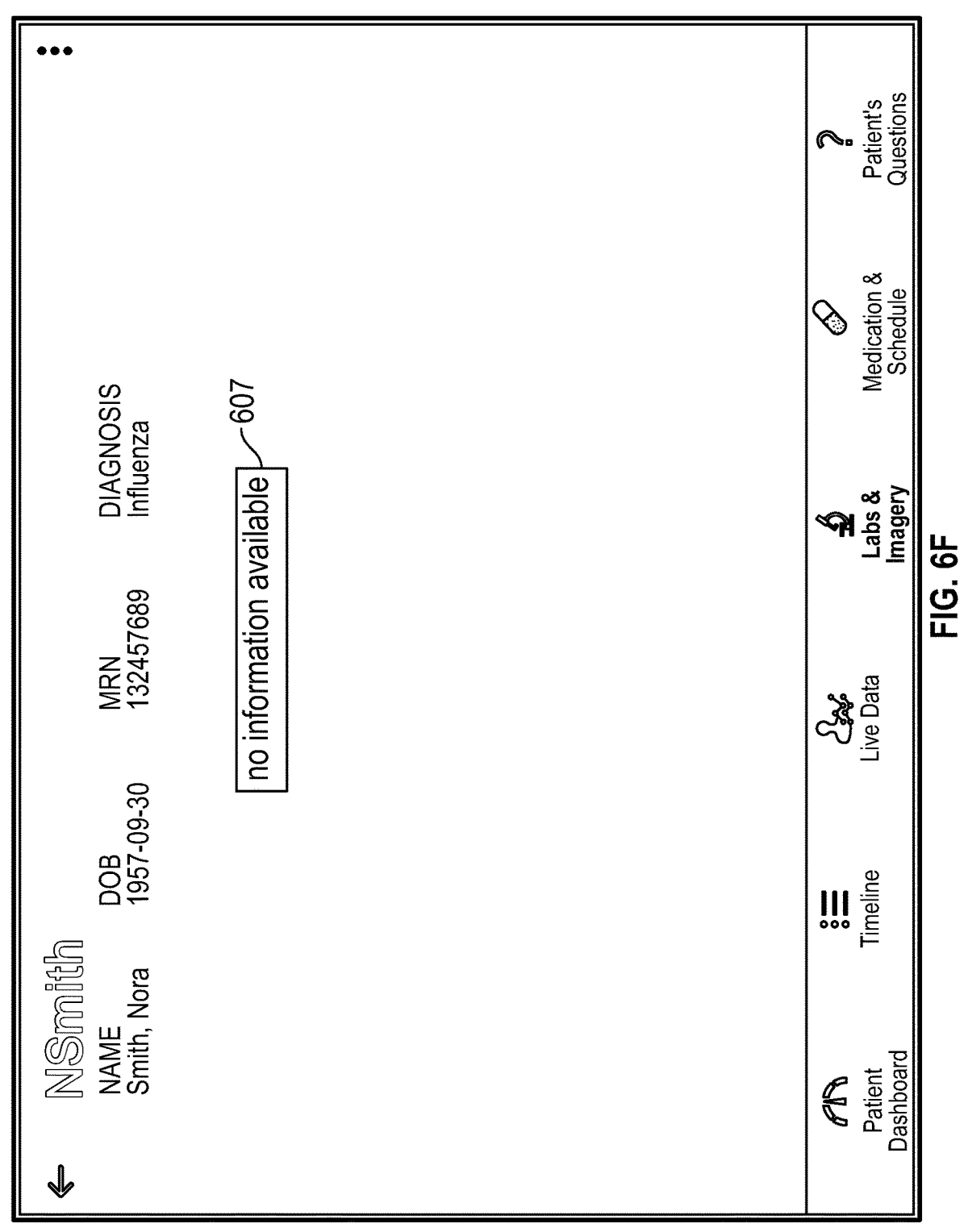

FIG. 6A shows an example Labs & Imagery screen 600, which may display the patient's lab results 601. The Labs & Imagery screen 600 may be accessed via the control panel 305. The navigation tabs 602 can allow the physician to select lab results by test and even to view patient x-rays. FIGS. 6B-6D show alternate layouts that may support one-fishbone chart display 603, two-fishbone chart display 604, or three-fishbone chart display 605. In some configurations, the layouts which display fishbone charts also display the patient's full lab results 601. In other configurations, the layouts with fishbone charts may only display fishbone charts to summarize the lab results. Typically, not all parts of a lab report are important in a diagnosis, and the alternate layouts may consolidate the most important information in a digestible format for physicians, which can allow them to work more efficiently. FIG. 6E is an example x-ray viewing screen 606 where physicians can review the patient's x-rays. FIG. 6F illustrates an example Labs & Imagery screen 600 when the patient file is empty, the device loses connection to the hospital network, or any other reason the device may not receive data updates. In such cases, the Labs & Imagery screen 600 may display a no connection warning 607.

Figure 7C:
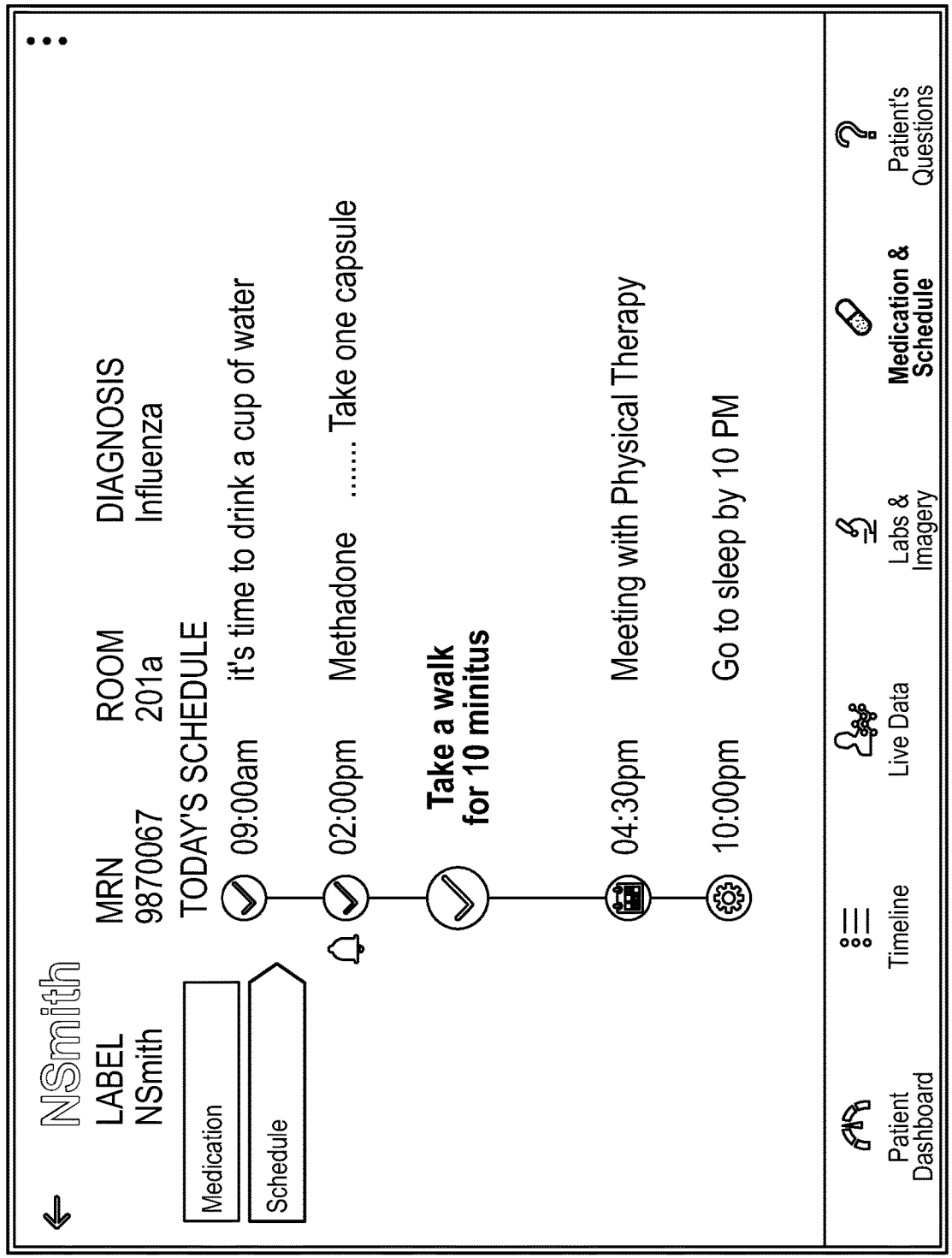
Figure 7D:
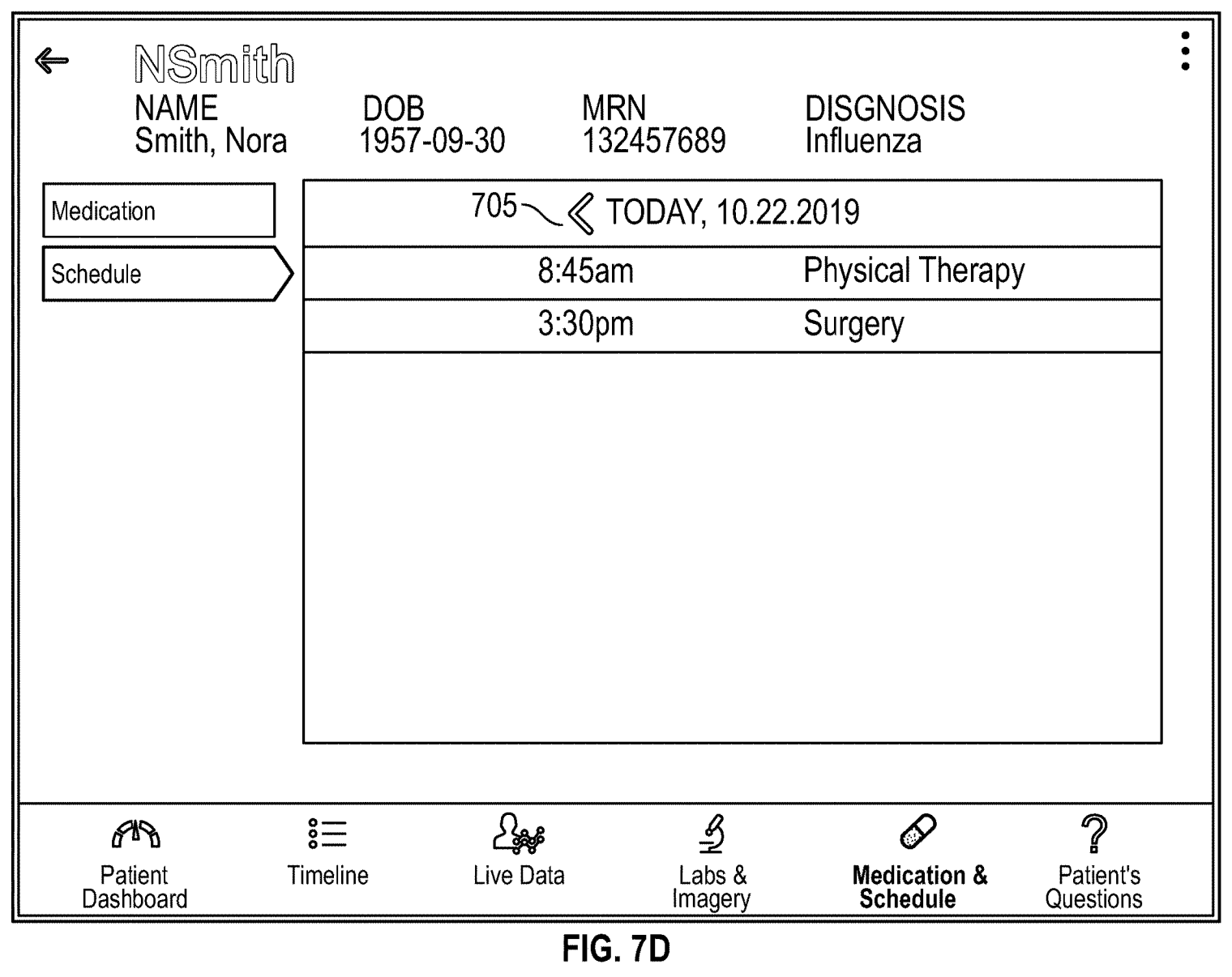

FIGS. 7A-7D show an example Medication & Schedule screen 700. The Medication & Schedule screen 700 may be accessed via the control panel 305. As shown in FIG. 7A, the navigation menu 701 can allow the medical staff to view the patient's prescribed medication details 702 and daily schedule 704 (as shown in FIG. 7C). The medication details 702 may include, but is not limited to, the name of the medication, information regarding administration of the medication, the physical form of the medication, etc. FIG. 7B illustrates an example Medication & Schedule screen 700 when the patient does not have prescribed medications, the device loses connection to the hospital network, or any other reason the device may not receive data updates. In such cases, the interface may display a no information warning 703. FIG. 7C is an exemplary illustration of the schedule sub-screen 704, which may display the patient's daily schedule. The daily schedule may include details of each planned activity or event and may include a time for each event. The schedule sub-screen 704 may also indicate whether an activity has been completed. The activity may be automatically marked as completed once the scheduled time has passed, or the activity may only be marked as completed based on healthcare provider input. FIG. 7D is an alternative configuration of the schedule sub-screen 704, in which the user may scroll through different days' schedules via a date selector 705.

Figure 8:
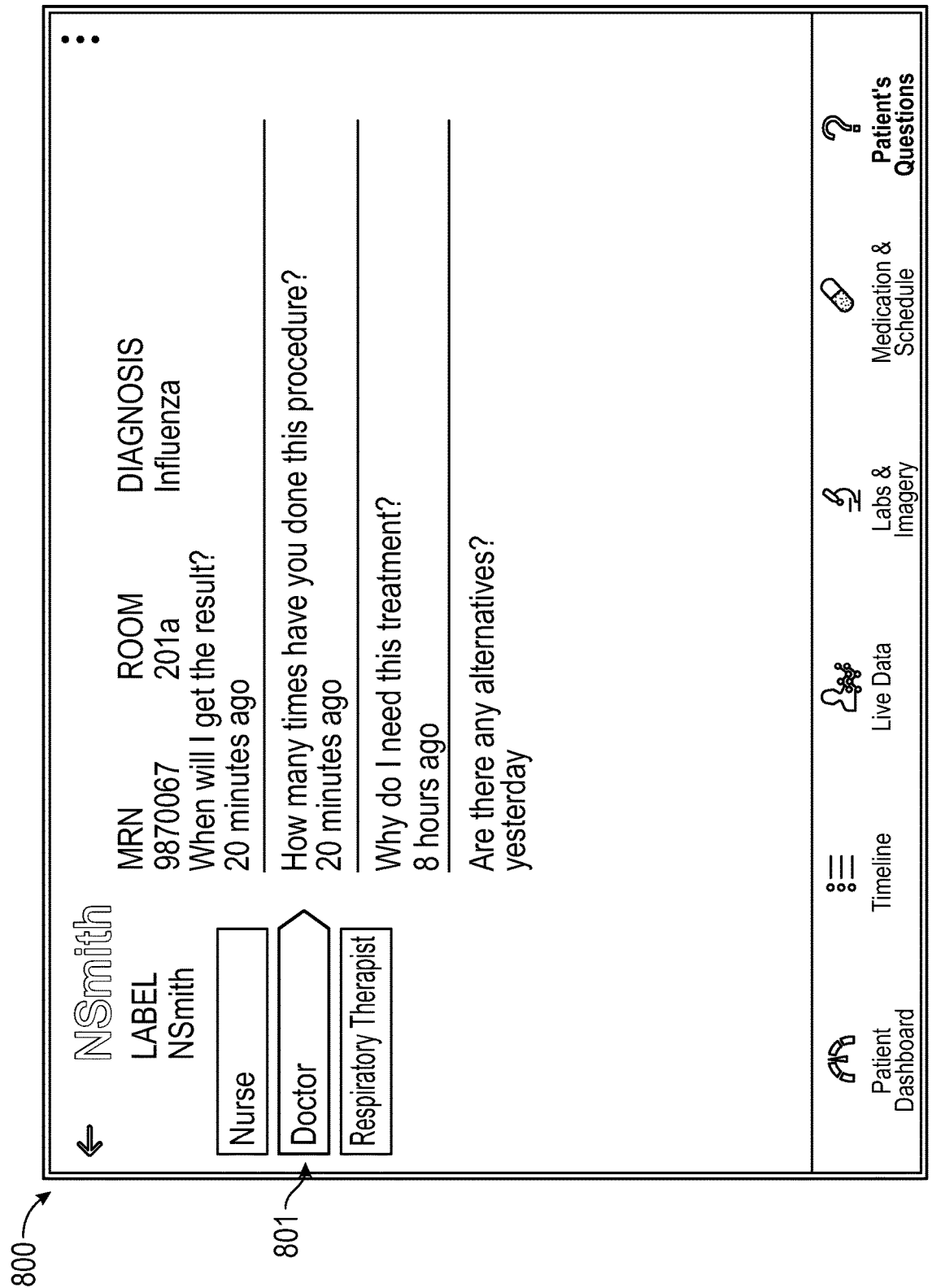
FIG. 8 is an illustrative interface showing patient questions for various specialists.

FIG. 8 shows an example Patient's Questions screen 800. The Patient's Questions screen 800 may be accessed via the control panel 305. The Patient's Questions screen 800 may display questions that patients input to a corresponding patient-facing interface of the physiological patient monitoring system. The patient-facing interface may be accessed through an application on a patient-accessible portable device. The staff selection panel 801 can allow medical staff to view only the questions that pertain to them. The staff selection panel 801 may list specific specialists, such as radiologist, oncologist, or respiratory therapist, rather than just generic titles such as doctor or nurse.

Figure 9B:
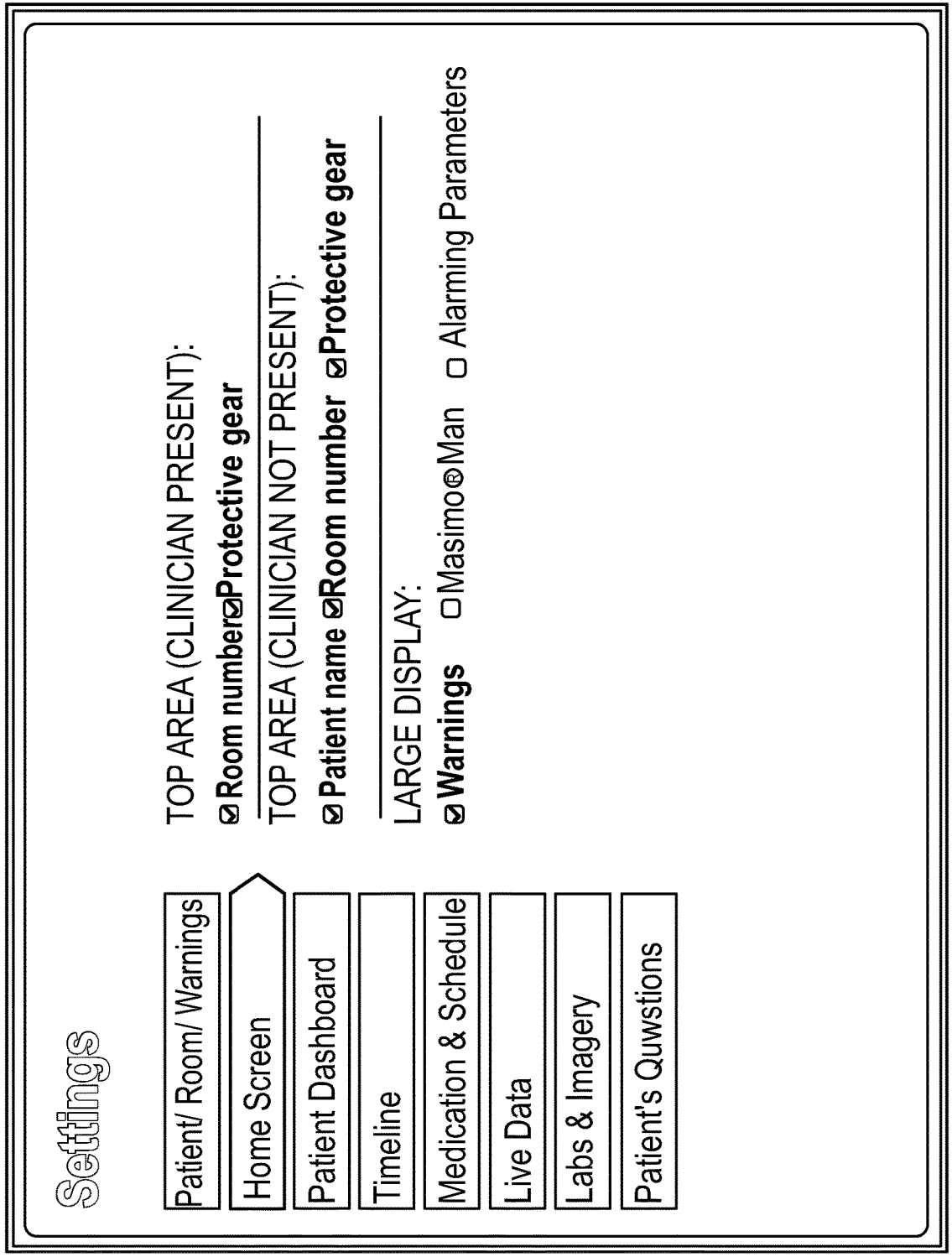
FIGS. 9A-9O are illustrative interfaces of the settings page of a physiological patient monitoring system where hospital staff can update display preferences, according to some embodiments.
Figure 9C:
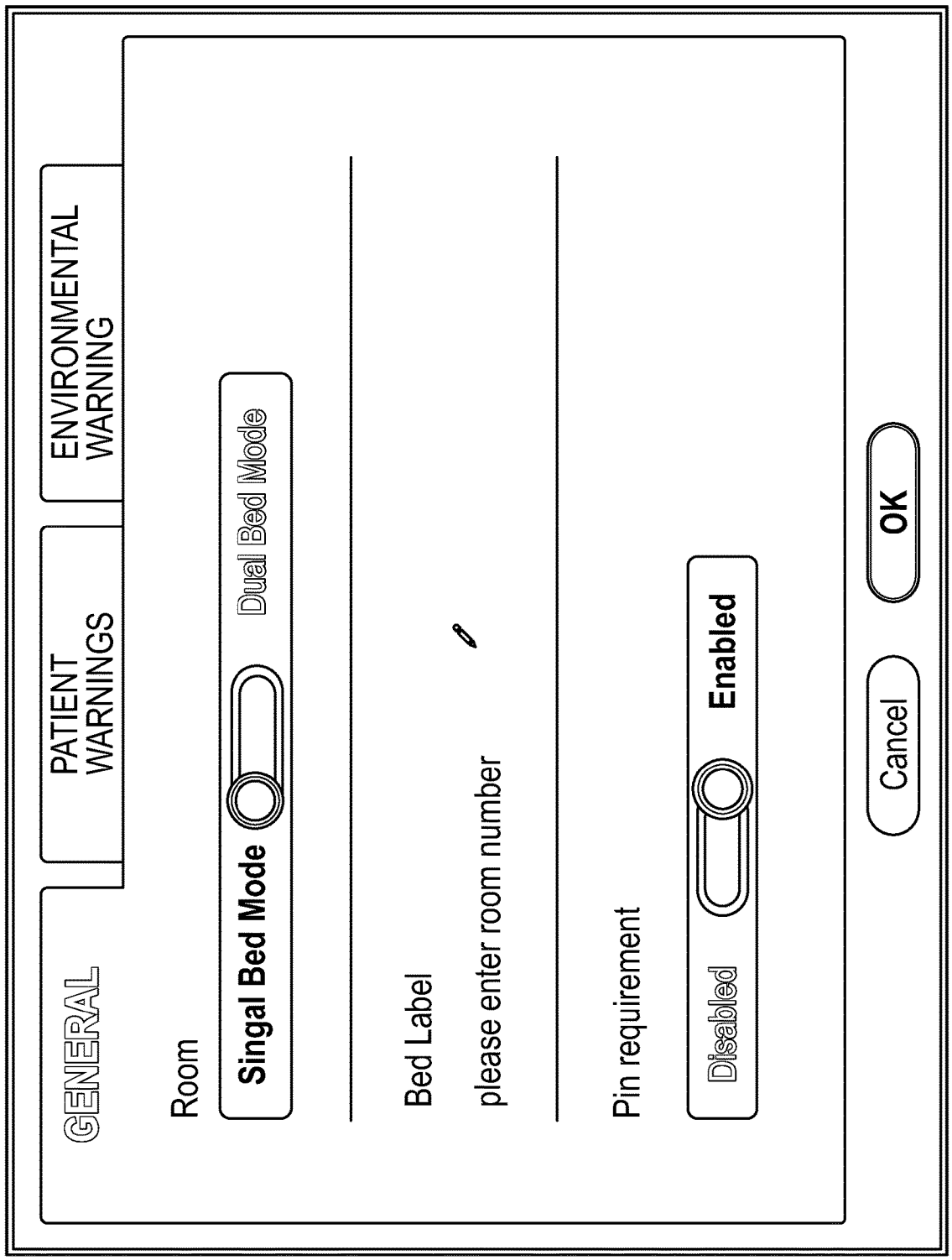
Figure 9D:
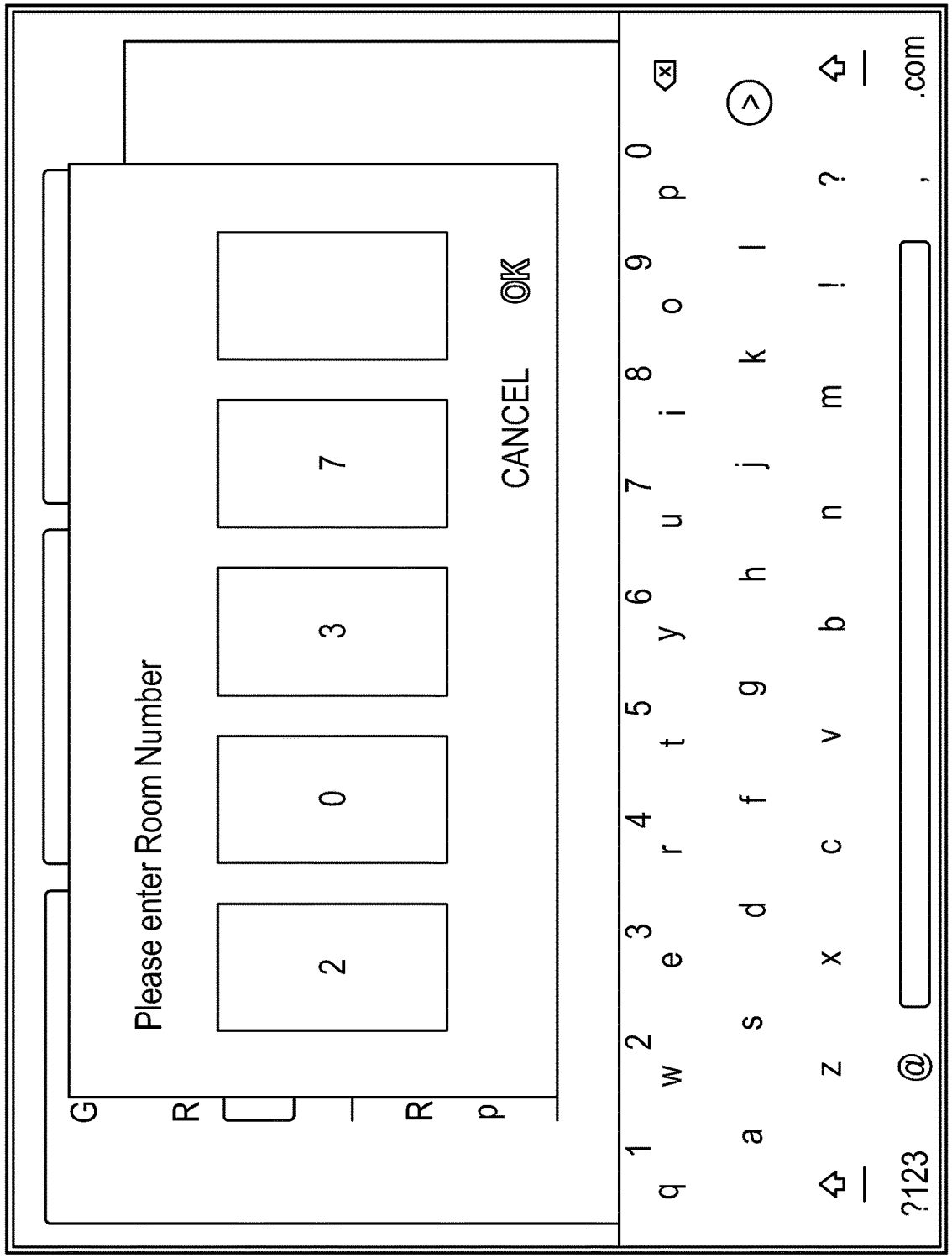
Figure 9E:
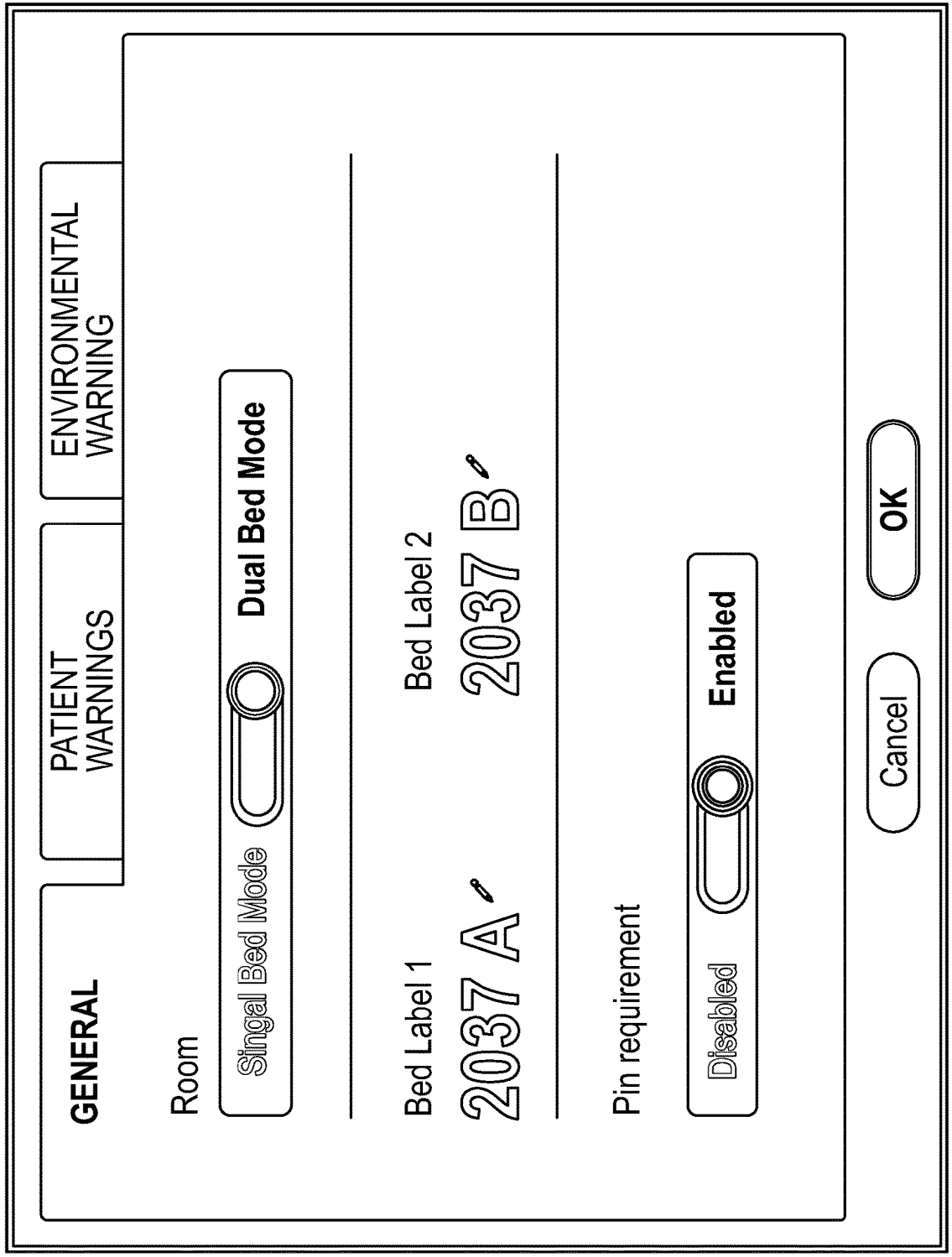
Figure 9F:
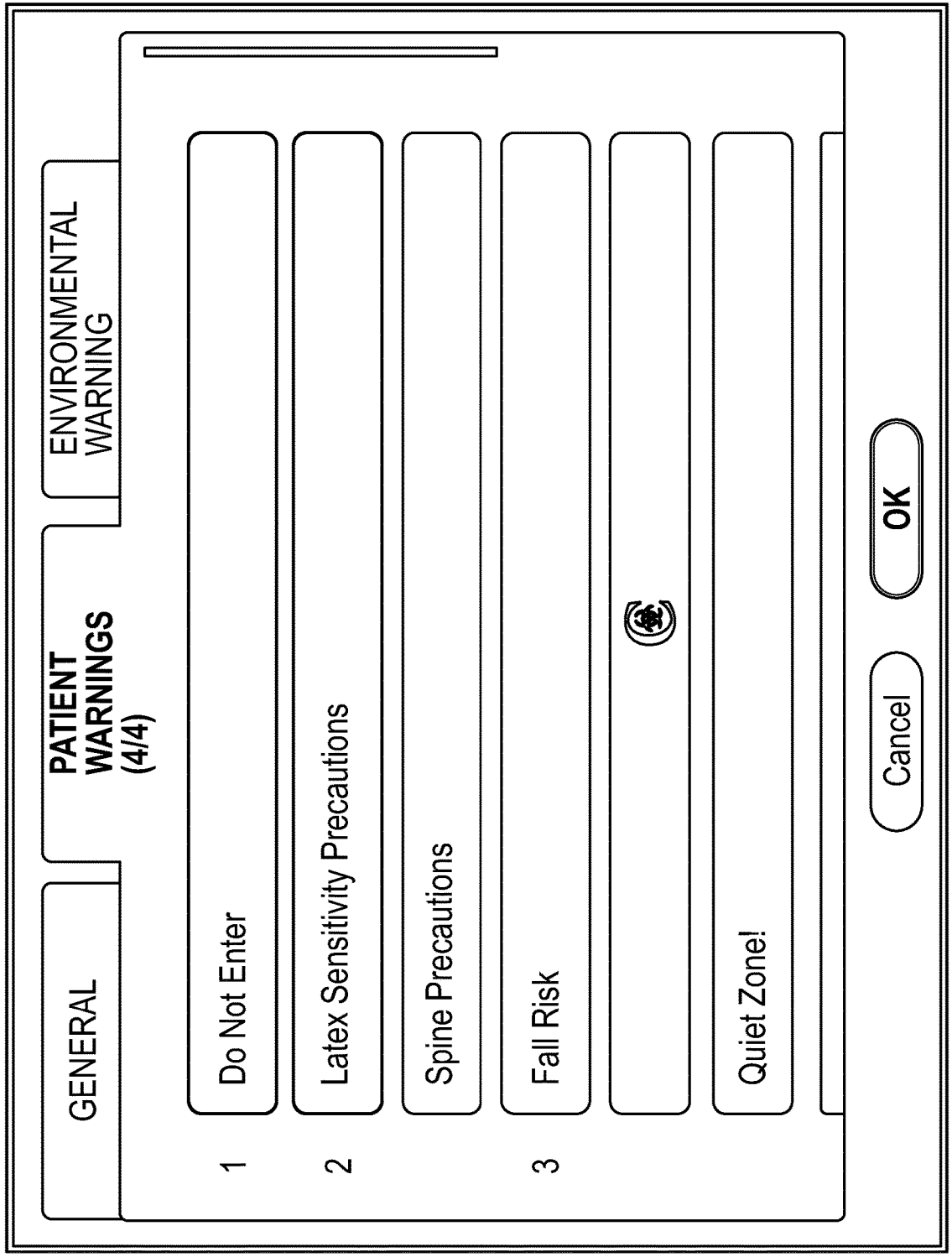
Figure 9G:
Figure 9H:
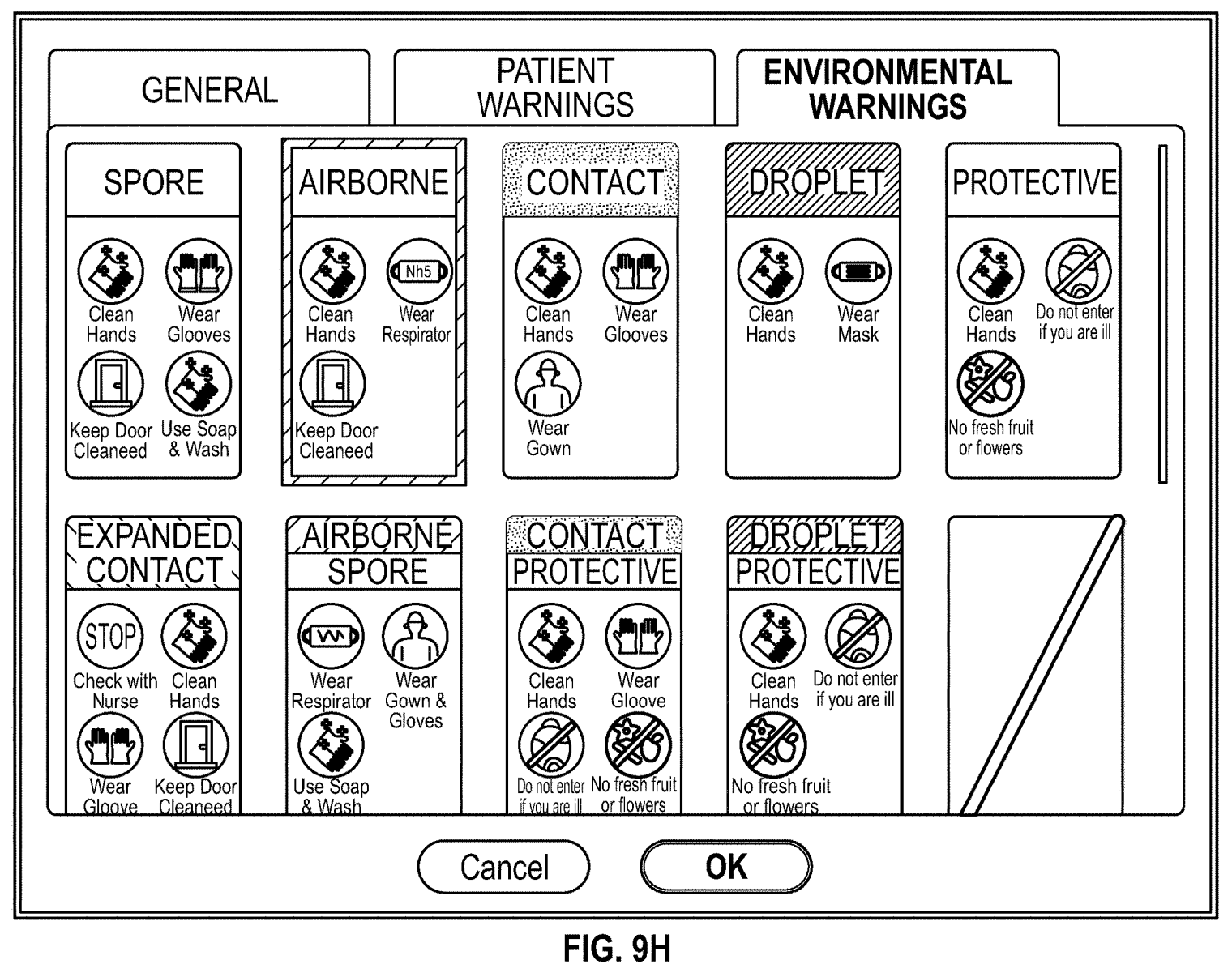
Figure 9I:
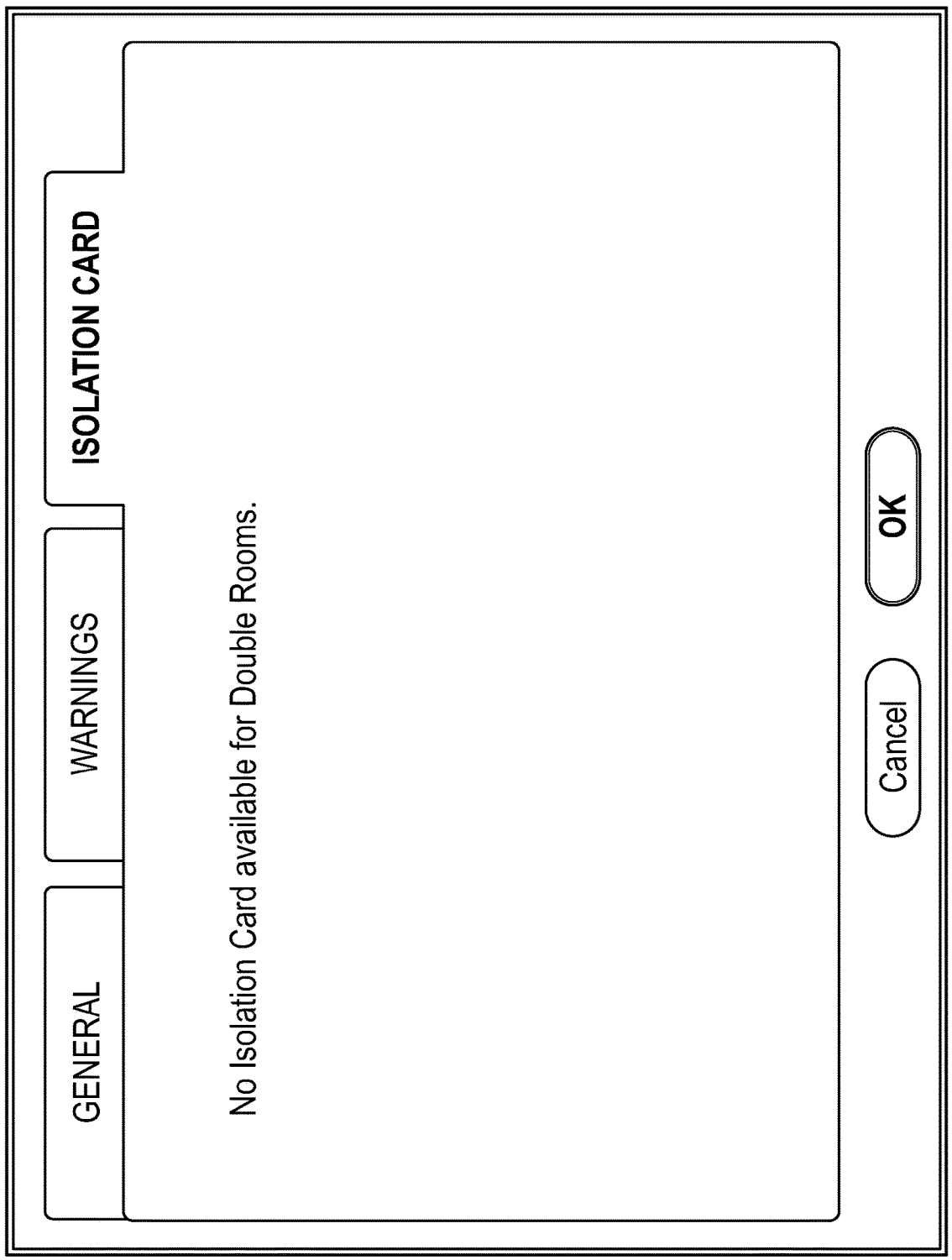
Figure 9J:
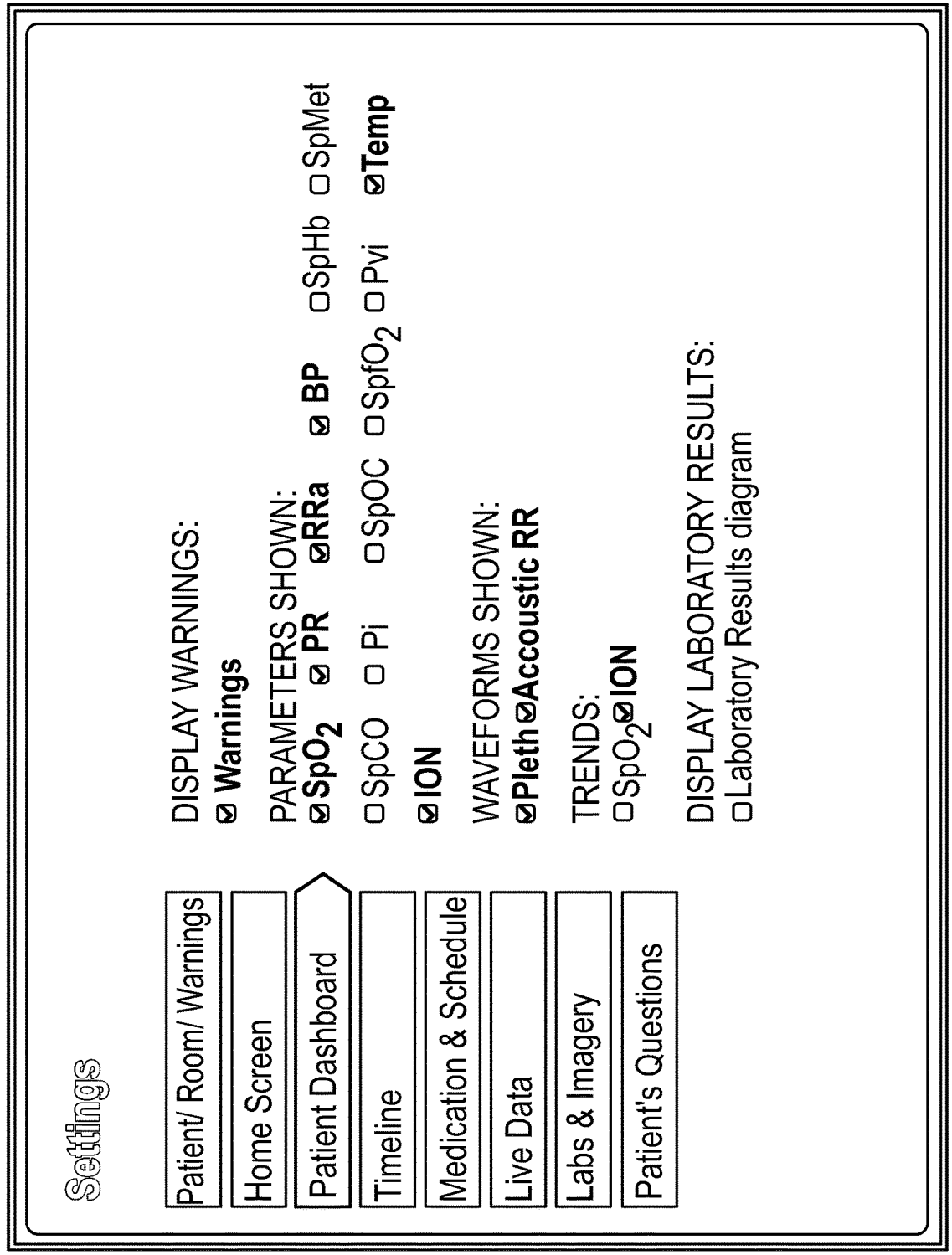
Figure 9K:
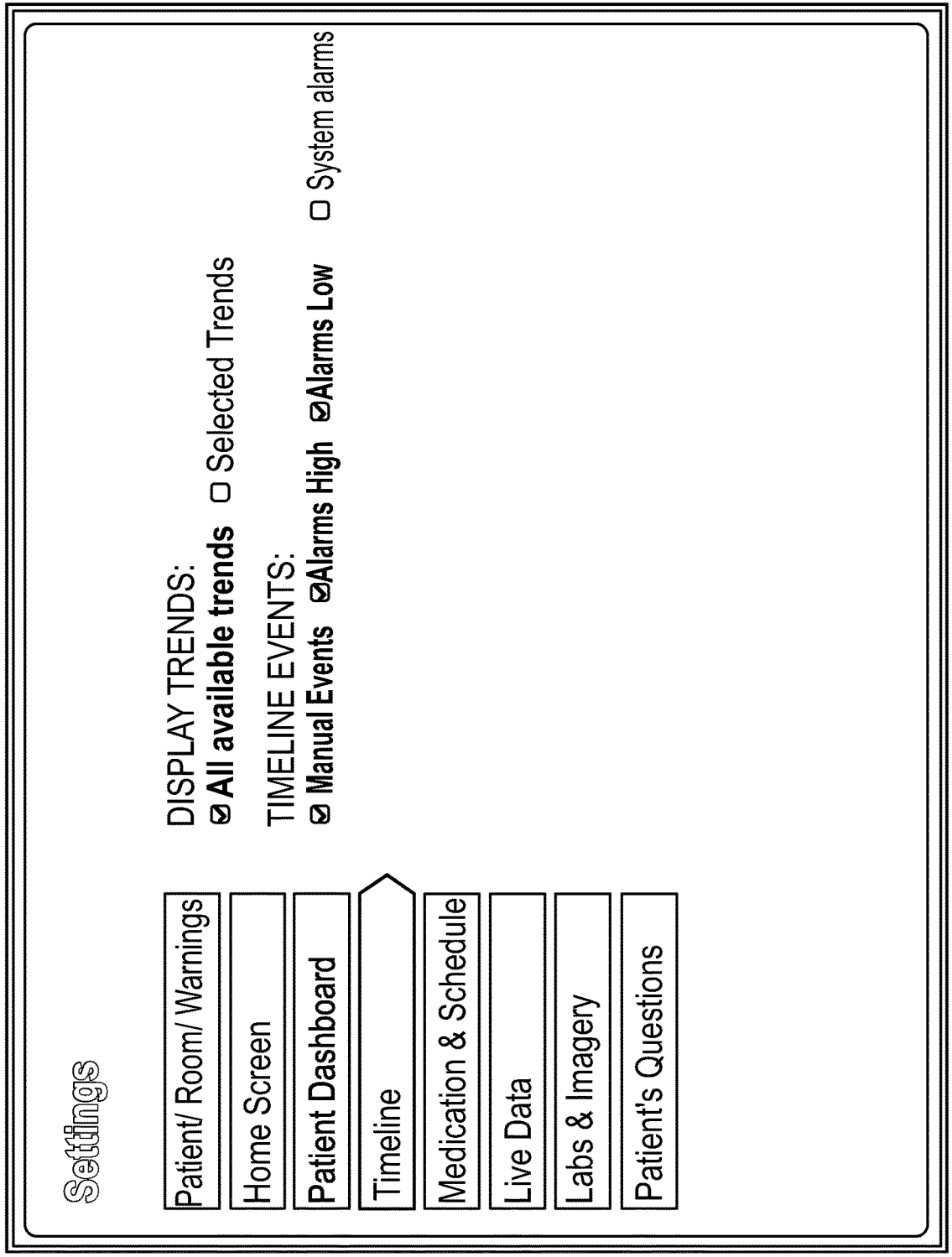
Figure 9M:
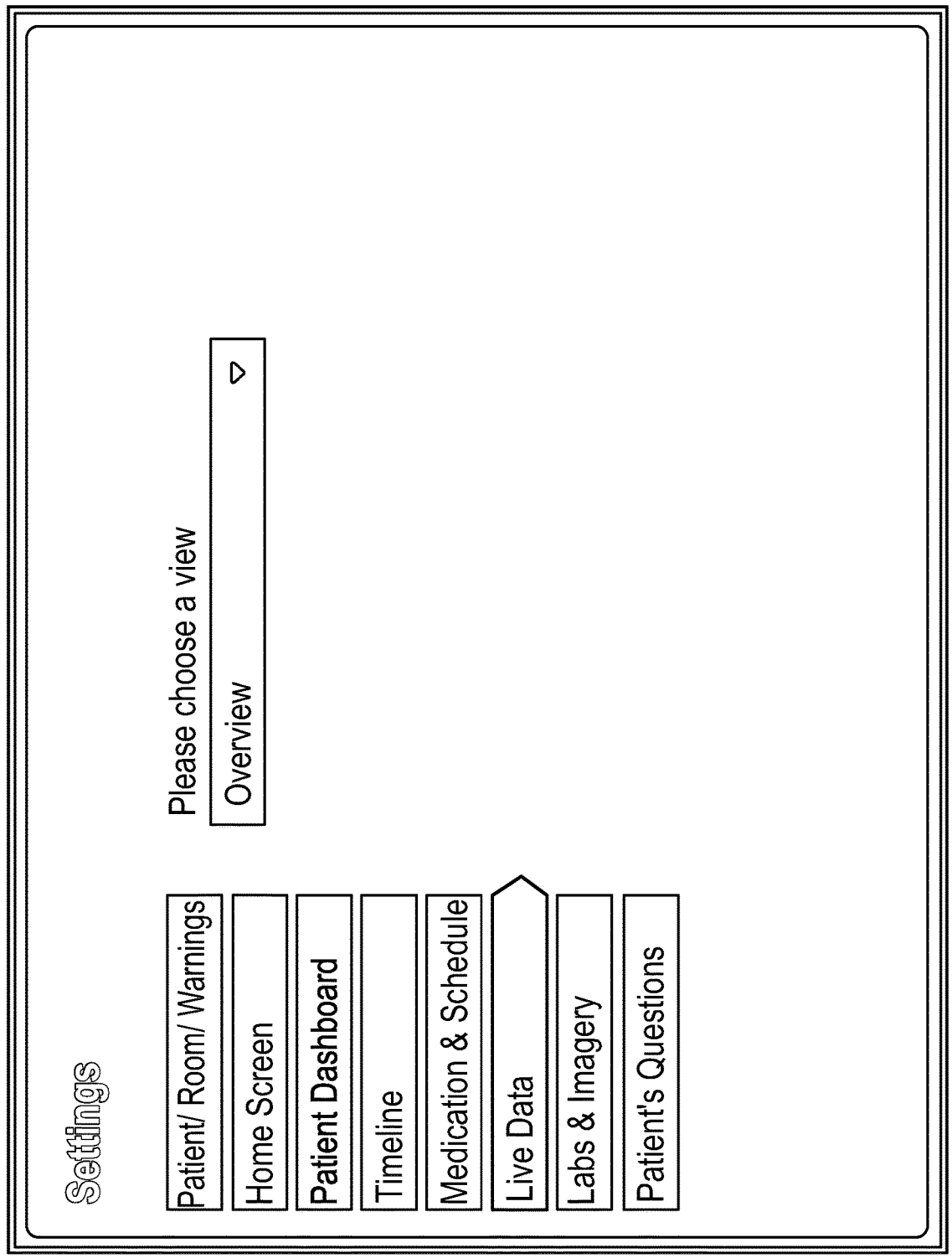
Figure 9N:
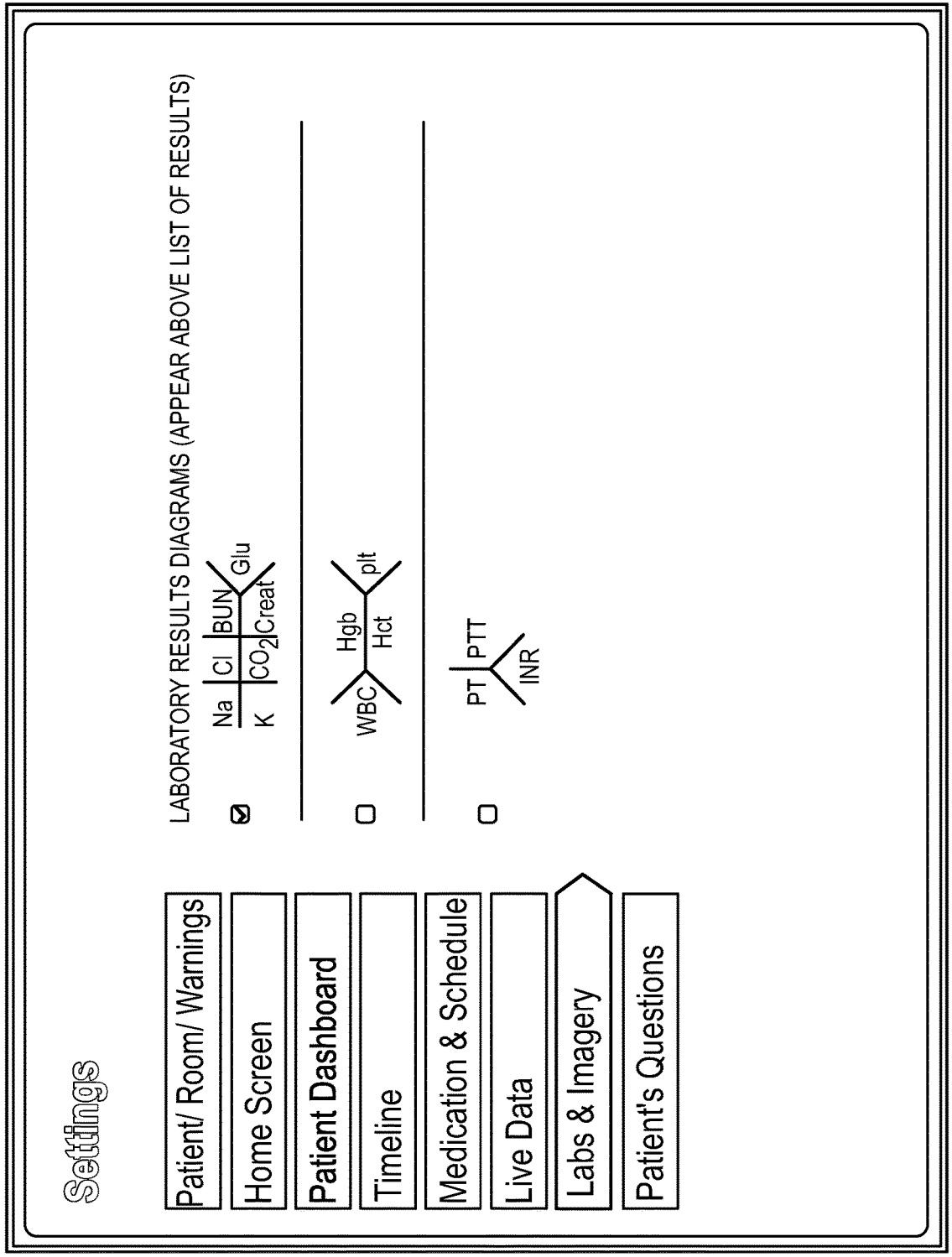
Figure 9O:
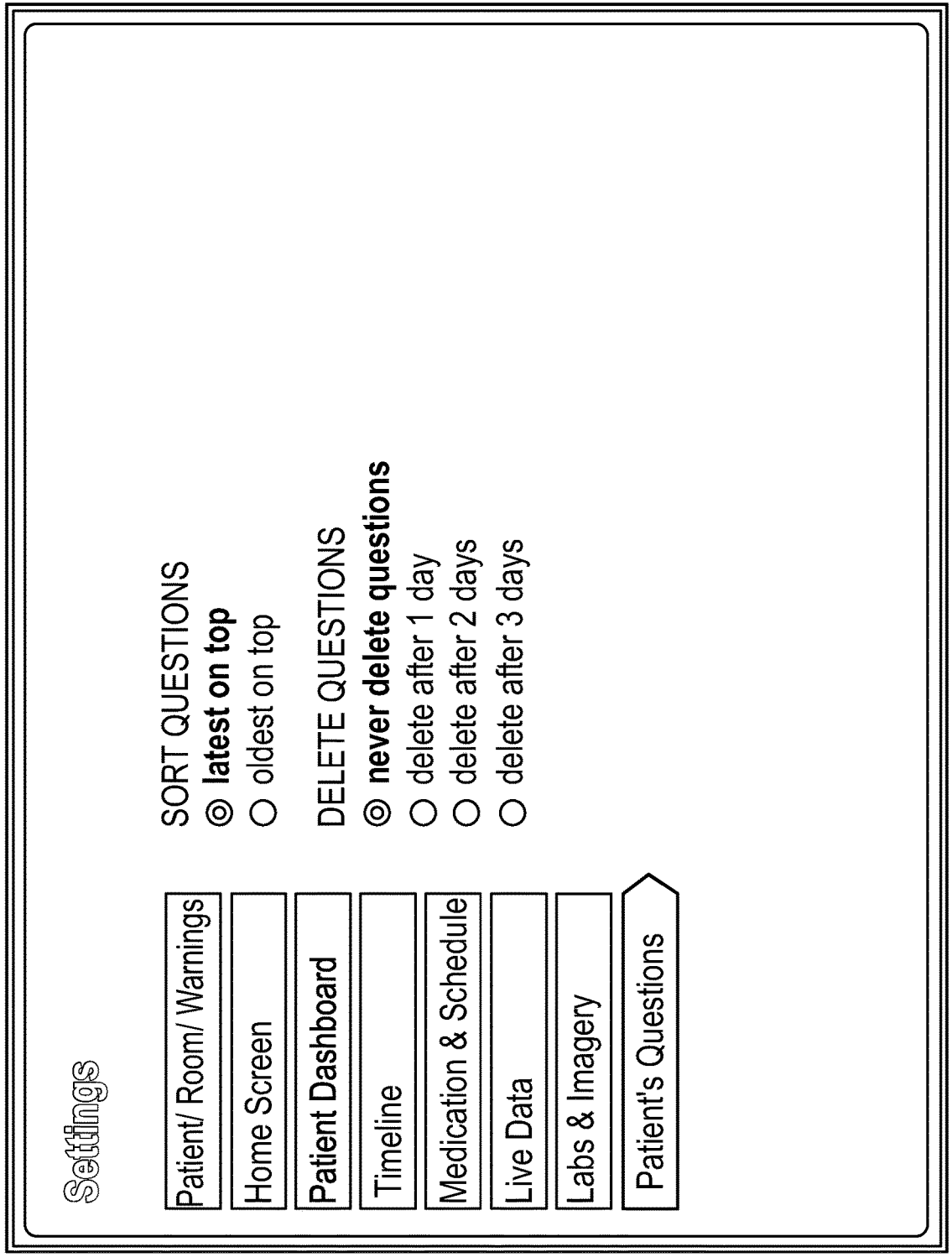

FIGS. 9A-9O illustrate various example pages of the application's settings where hospital staff can update patient information and display preferences. The settings may be accessed via the settings menu icon 205, 762. A navigation panel 900 may allow healthcare providers to edit the features displayed on the default screen 200 and each screen listed on the control panel 305. The settings screen may be used to change the application display to show the number of beds in a room, set default displays in cases where the device cannot connect to patient data, update patient information, update patient scheduling, update medication information, or customize and/or update any feature described herein.

Figure 10A:
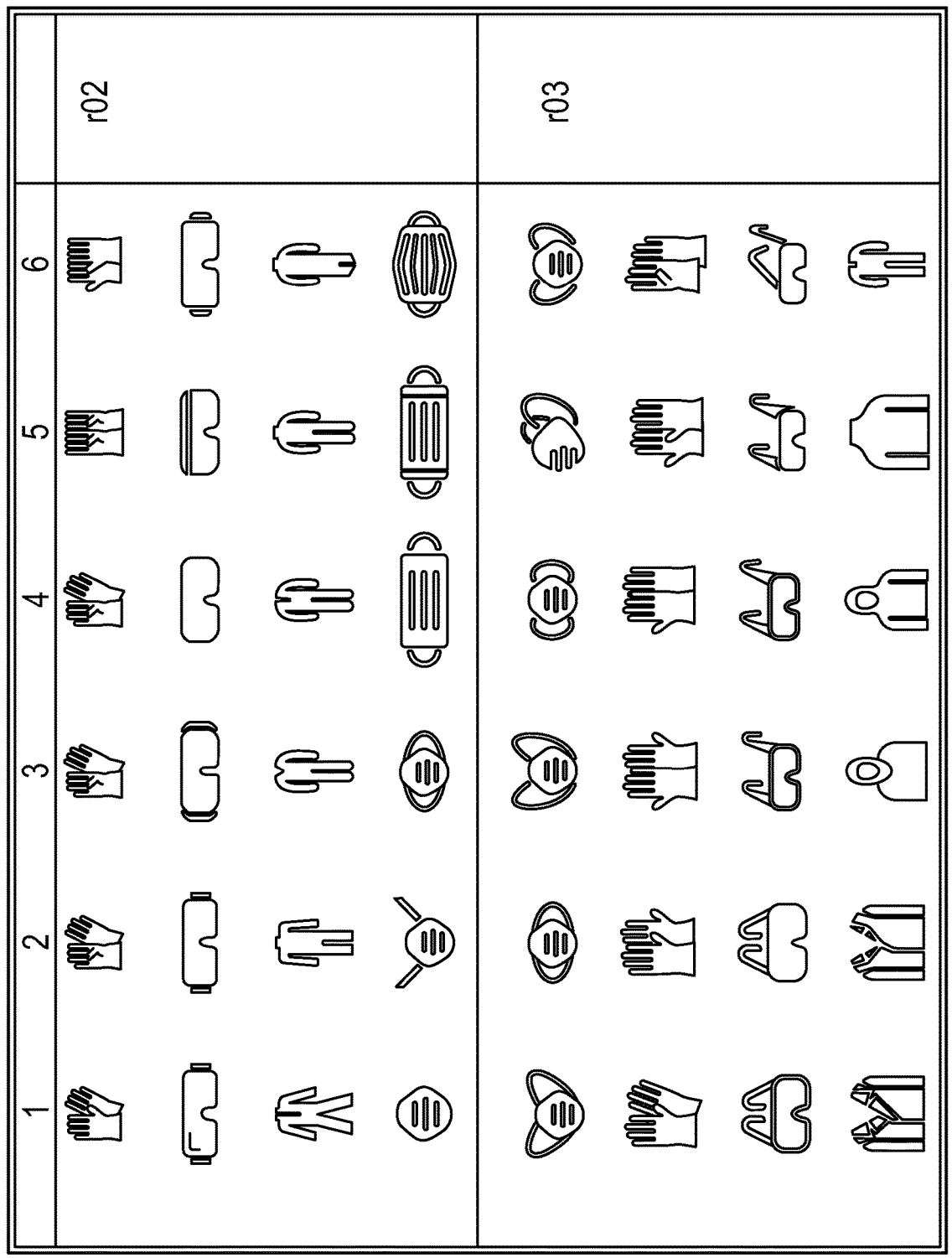
FIGS. 10A-10C depict potential variations of the symbols and warnings used in a physiological patient monitoring system.
Figure 10B:
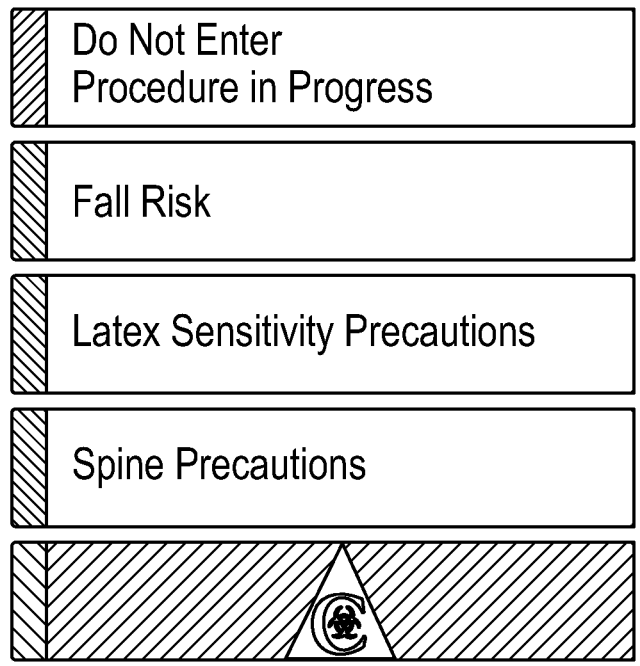
Figure 10C:
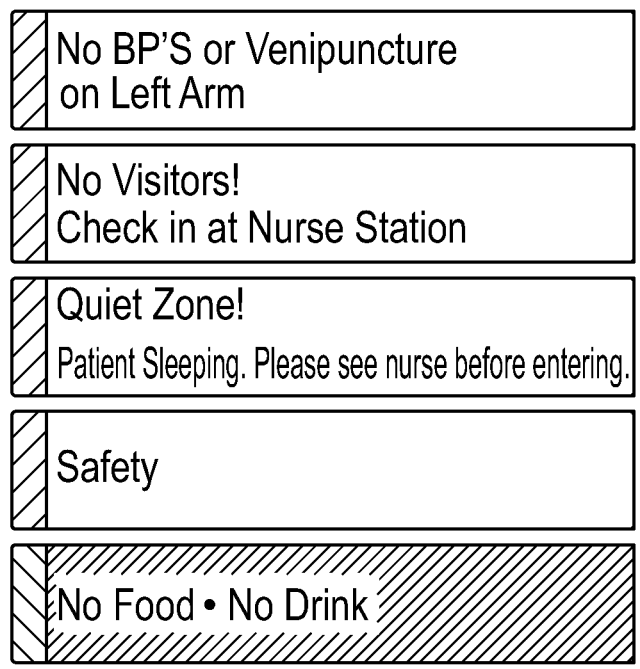

FIG. 10A illustrates potential variations of the safety precaution symbols used in the application. FIGS. 10B and 10C show lists of possible patient warnings that clinicians may choose for display on the interface default screen. FIGS. 10A-C should be understood to be non-limiting and do not preclude the use of other symbols and warnings not explicitly disclosed in the present figures.

Figure 11A:
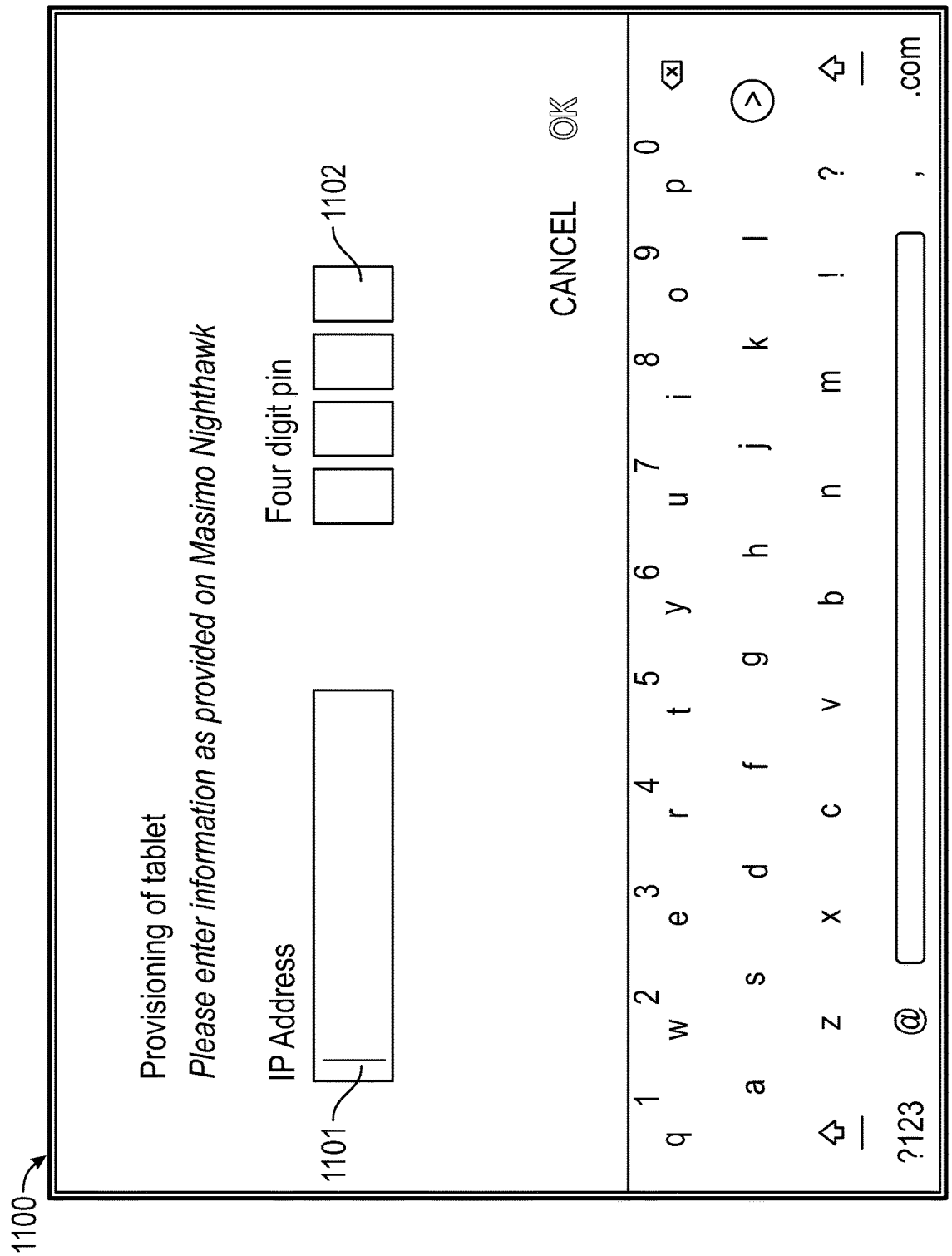
FIGS. 11A-11E are illustrative interfaces of clinician login pages to set up a physiological monitoring system for initial use, according to some embodiments.
Figure 11B:
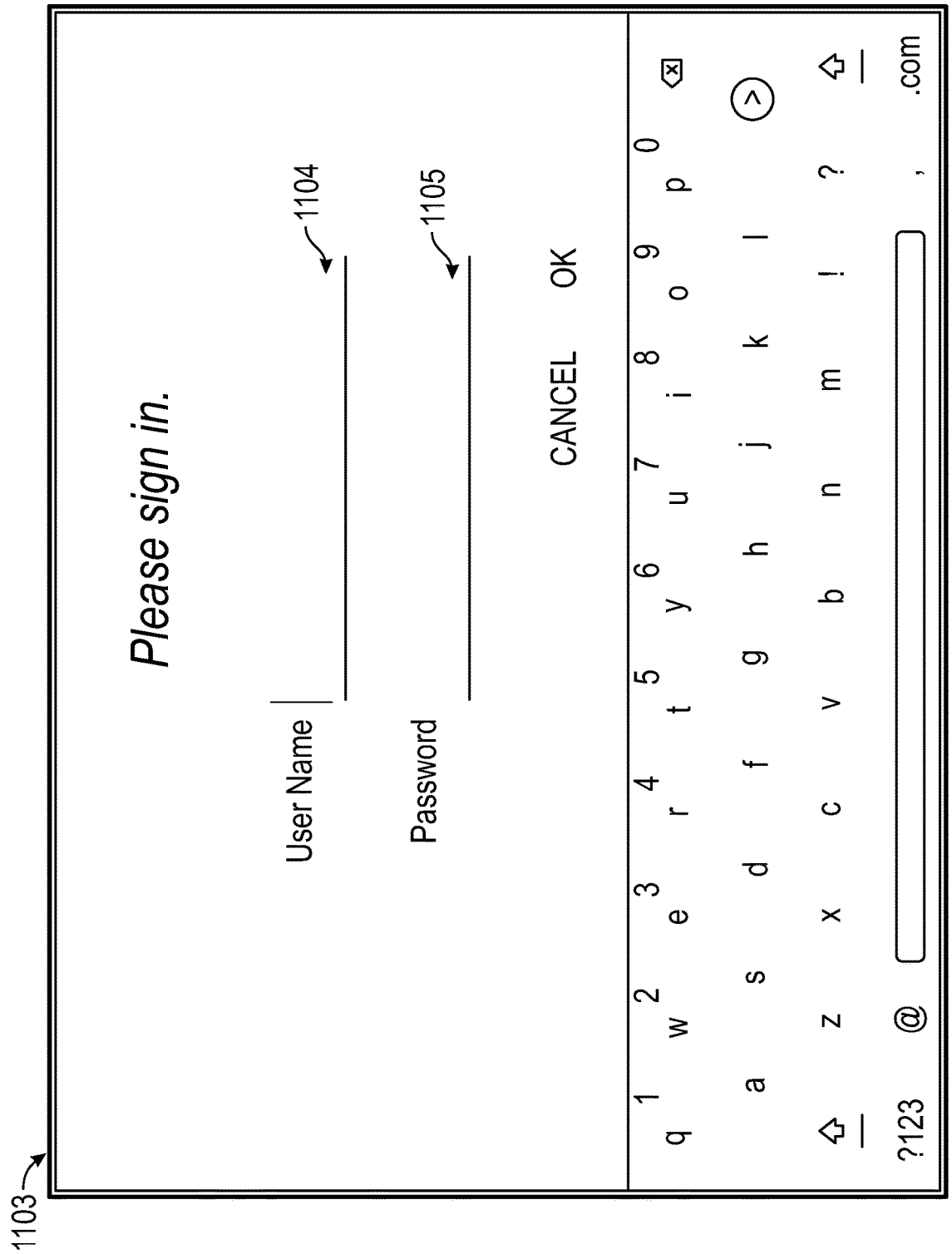
Figure 11C:
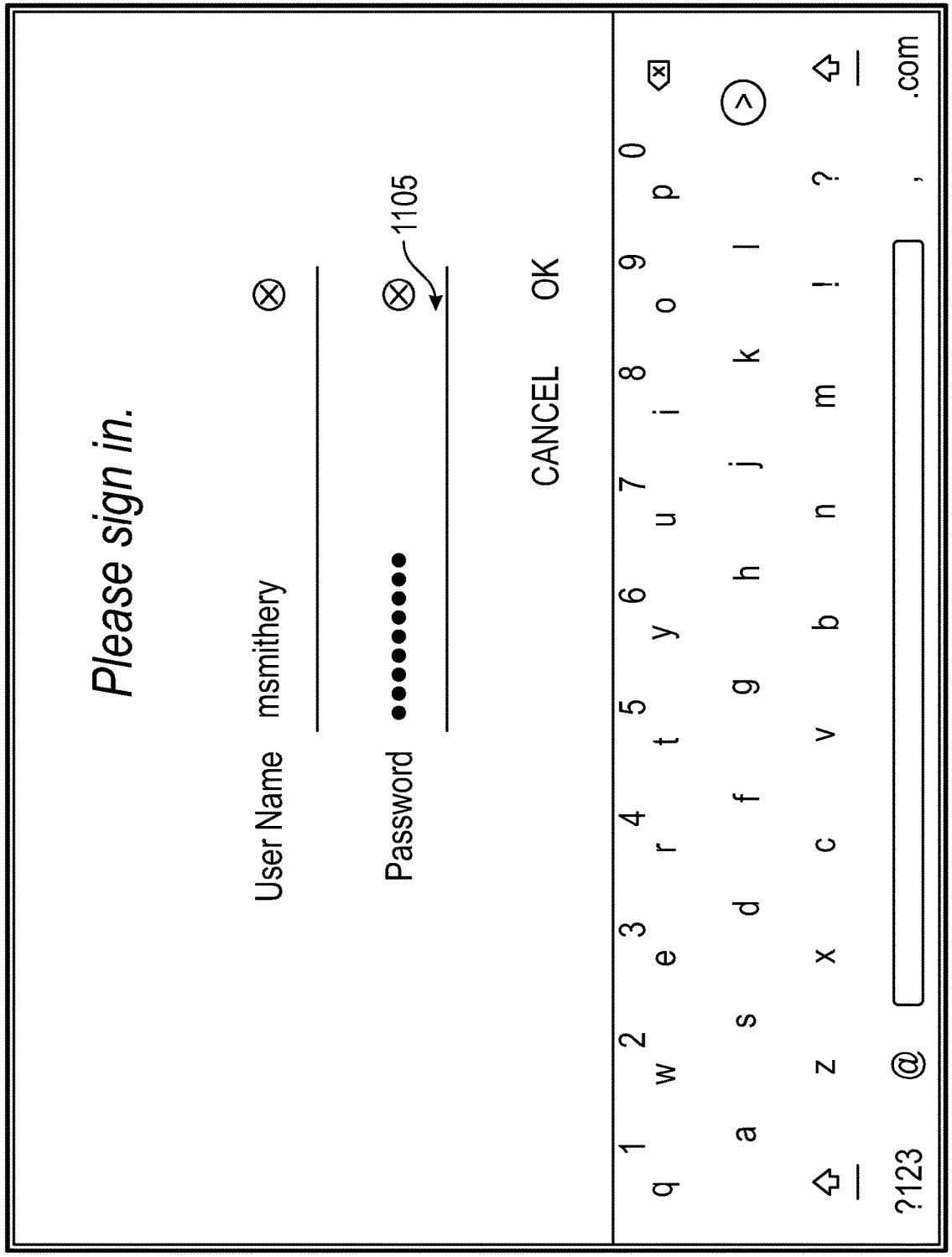
Figure 11D:
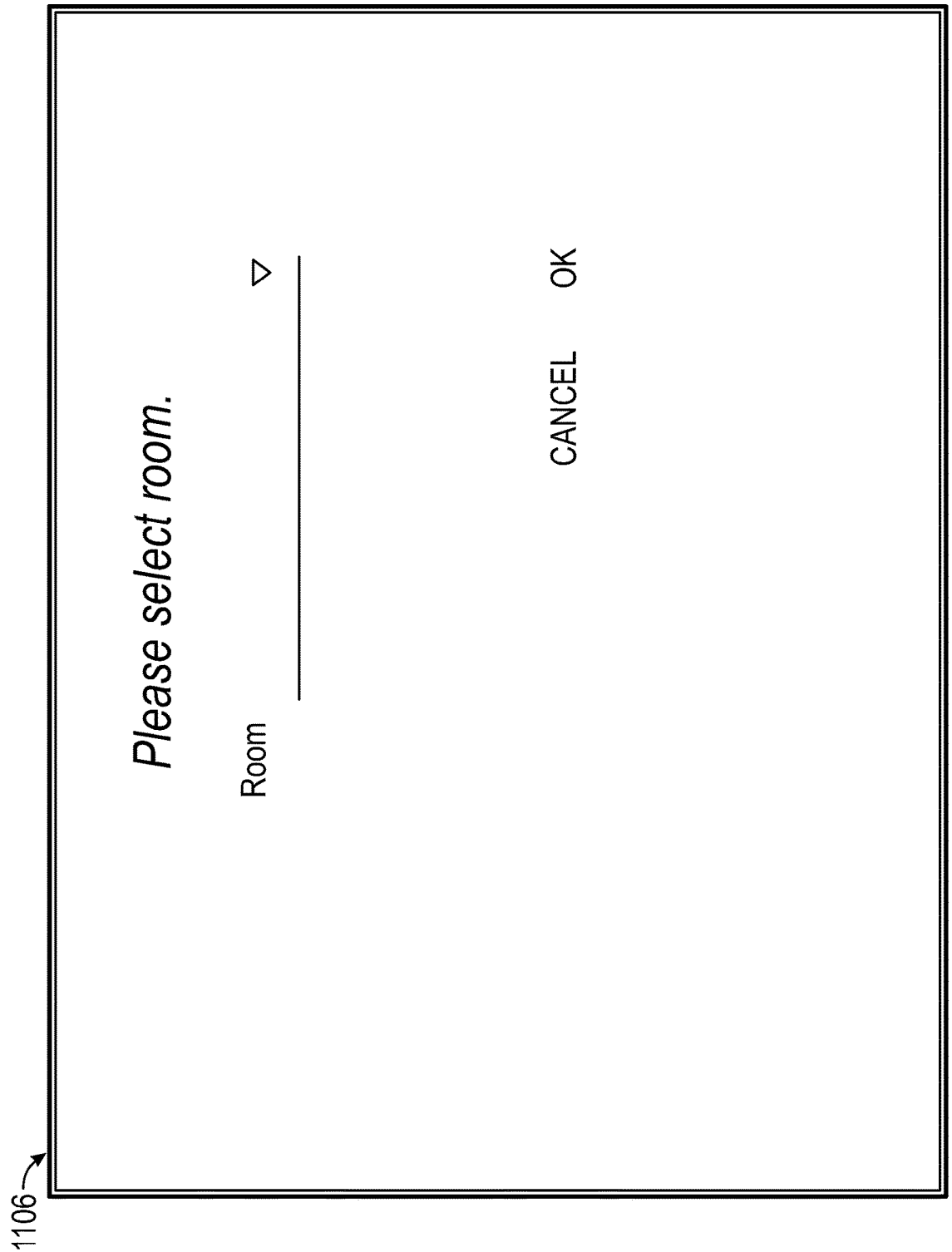
Figure 11E:
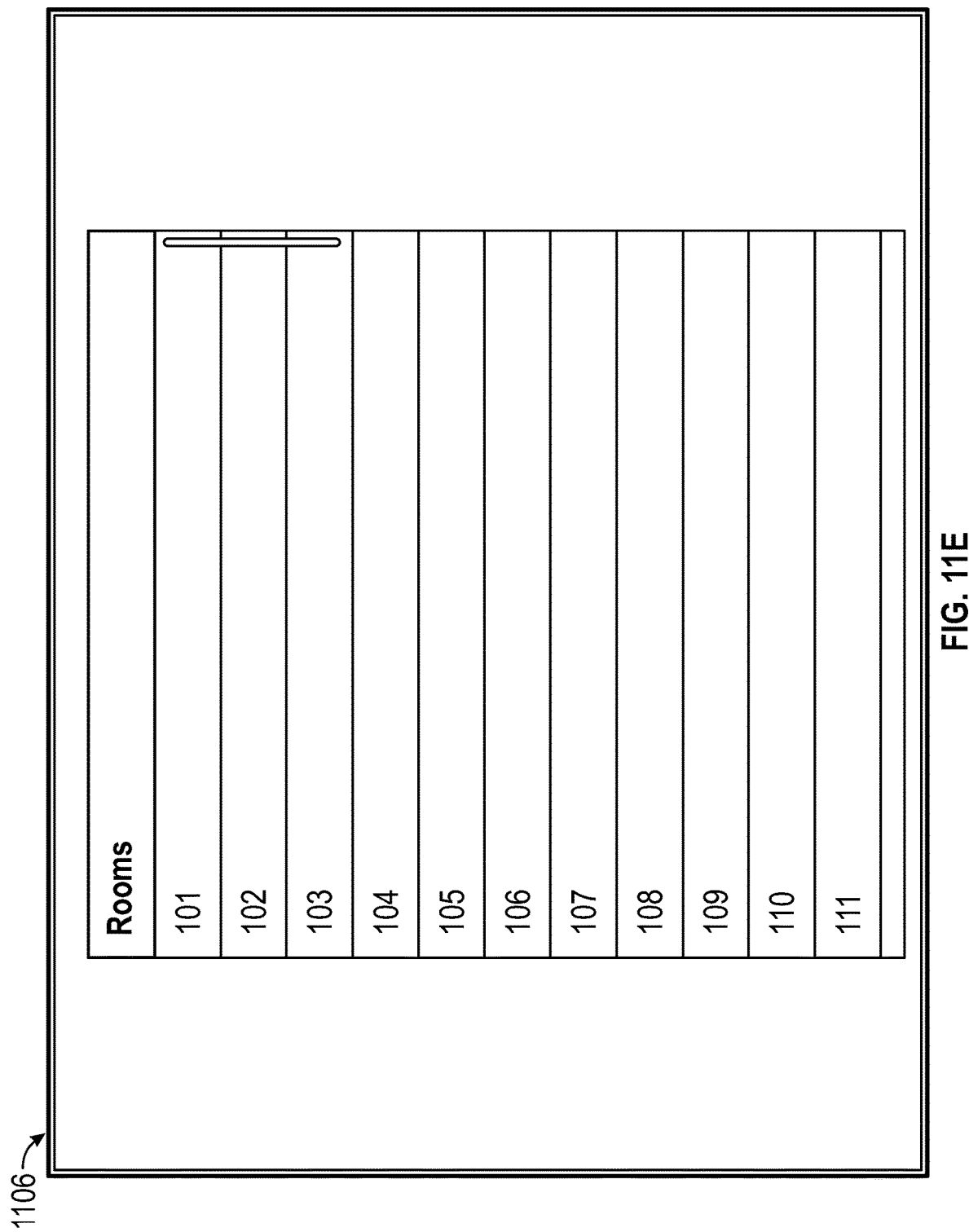

FIGS. 11A-E are exemplary configurations of set-up screens for the healthcare professional interface of the physiological patient monitoring. The set-up screens may appear prior to the first use of the application. FIG. 11A illustrates an example provisioning screen 1100 with an Internet Protocol ("IP") address input 1101 and PIN input 1102. In some configurations, the passcode may not be a four-digit PIN, but rather, may be any length and comprised of any combination of symbols, characters, or digits. Provisioning is particularly important for devices used in healthcare due to the sensitive and protected nature of patient information. Using the device IP address ensures that only verified devices may communicate with the network and access private patient data. FIGS. 11B-C show an illustrative login screen 1103 with user name input 1104 and password input 1105. As shown in FIG. 11C, the password input 1105 may censor the characters so that the passcode cannot be accidentally seen by un-intended audiences. In such configurations, there may be an additional option to reveal the password. FIGS. 11D & 11E are example room selection screens 1106. The room selection screen 1106 can allow system administrators to pair the device with a specific hospital room. FIG. 11E illustrates an example room selection screen 1106 where a room may be selected from a drop-down menu. In other configurations, the room number may be typed in via virtual keyboard.

The various features and processes described above may be used independently of one another or may be combined in various ways. All possible combinations and sub-combinations are intended to fall within the scope of this disclosure. In addition, certain interfaces and features may be omitted in some implementations. The interfaces described herein are also not limited to any particular sequence and may be arranged in other sequences that are appropriate. Features may be added to or removed from the disclosed example configurations. The example systems and components described herein may be configured differently than described. For example, elements may be added to, removed from, or rearranged compared to the disclosed example configurations Conditional language, such as, among others, "can," "could," "might," or "may," unless specifically stated otherwise, or otherwise understood within the context as used, is generally intended to convey that certain configurations include, while other configurations do not include, certain features, elements and/or steps. Thus, such conditional language is not generally intended to imply that features, elements and/or steps are in any way required for one or more configurations or that one or more configurations necessarily include logic for deciding, with or without user input or prompting, whether these features, elements and/or steps are included or are to be performed in any particular configuration.

It should be emphasized that many variations and modifications may be made to the above-described configurations, the elements of which are to be understood as being among other acceptable examples. All such modifications and variations are intended to be included herein within the scope of this disclosure. The foregoing description details certain configurations of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A system configured to be secured in proximity to a door outside a room in a hospital, the system comprising:
   a receptacle non-removably positioned in proximity to the door outside the room; and
   a portable electronic device configured to be removably attached to the receptacle;
   said portable electronic device comprising a display and one or more hardware processors configured to:
      receive patient data from a healthcare data network, wherein the patient data corresponds to a patient in the room;
      automatically generate safety information based at least in part on the patient data, wherein the safety information provides a warning for a visitor to use personal protective equipment;
      generate a first user interface for presentation on the display, said first user interface configured to display de-identified information corresponding to the patient in the room, including the safety information, wherein the first user interface is locked and comprises an unlock screen;
      receive, via the unlock screen, authentication data indicating that a care provider is authenticated to access the display; and
      generate a second user interface for presentation on the display based on the received authentication data, said second user interface configured to display the patient data including the patient's personal information and medical data, wherein the medical data includes the de-identified information and other information, wherein at least some of the other information is displayed in a fishbone diagram.

2. The system of claim 1, wherein the receptacle comprises a mechanical locking mechanism configured to unlock the receptable upon receipt of authentication.

3. The system of claim 2, wherein the locking mechanism includes at least one of: a hardware latch, a magnetic latch, an electromagnetic latch, or an electronically-controlled hardware latch.

4. The system of claim 1, wherein the receptable comprises a bin.

5. The system of claim 1, wherein the safety information further includes at least one of: patient allergies, patient dietary regimen, procedure alert, or patient fall risk warning.

6. The system of claim 1, wherein to automatically generate the safety information, the one or more hardware processors are configured to:
parse the patient data;
identify a risk in the patient data; and
generate the safety information that addresses the risk.

7. The system of claim 1, wherein the one or more hardware processors are further configured to:
generate a third user interface for presentation on the display, said third user interface configured to display options relating to at least one other user interface; and
receive, via the third user interface, user input selecting display options to display on the at least one other user interface.

8. The system of claim 1, wherein the one or more hardware processors are further configured to:
receive updated patient data from the healthcare data network in real time;
process the updated patient data from the healthcare data network to generate graphical data displays; and
display, via a fourth graphical user interface, the graphical data displays.

9. The system of claim 8, wherein the graphical data displays further include at least one of: timelines, or ECG waveforms.

10. The system of claim 1, wherein the authentication data includes at least one of: a passcode, a Personal Identification Number ("PIN"), a Radio Frequency Identification ("RFID") chip scanner, biometric information, or hardware provisioning.

11. The system of claim 1, wherein the one or more hardware processors are further configured to display patient x-rays.

12. The system of claim 1, wherein the portable electronic device is programmable to receive and display patient data for multiple patients in the room.

13. A system comprising:
a dock non-removably positioned in proximity to a door of a room in a hospital; and
a portable electronic device configured to be secured to the dock;
said portable electronic device comprising a display and one or more hardware processors configured to:
automatically generate safety information based at least in part on patient data for a patient in the room, wherein the safety information provides a warning for a visitor to use personal protective equipment;
generate a first user interface for presentation on the display, said first user interface configured to display de-identified information corresponding to the patient in the room, including the safety information, wherein the first user interface is locked and comprises an unlock screen;
receive, via the unlock screen, authentication data indicating that a care provider is authenticated to access the display; and
generate a second user interface for presentation on the display based on the received authentication data, said second user interface configured to display additional patient data corresponding to the patient including the patient's personal information and medical data, wherein the medical data includes the de-identified information and other information, wherein at least some of the other information is displayed in a fishbone diagram.

14. The system of claim 13, wherein the dock comprises a physical locking mechanism configured to unlock the portable electronic device from the dock responsive to receipt of the authentication data.

15. The system of claim 14, wherein the locking mechanism includes at least one of:
a hardware latch, a magnetic latch, an electromagnetic latch, or an electronically-controlled hardware latch.

16. The system of claim 13, wherein the dock is placed on a ceiling.

17. The system of claim 13, wherein the dock is placed inside the room.

18. The system of claim 13, wherein the dock is placed outside the room.

19. The system of claim 13, wherein the dock is separable from the portable electronic device.

20. The system of claim 13, wherein the dock and the portable electronic device are integrated and cannot be removably separated.

* * * * *

UNITED STATES PATENT AND TRADEMARK OFFICE
CERTIFICATE OF CORRECTION

| | | |
|---|---|---|
| PATENT NO. | : 12,235,941 B2 | Page 1 of 1 |
| APPLICATION NO. | : 17/073133 | |
| DATED | : February 25, 2025 | |
| INVENTOR(S) | : Massi Joe E. Kiani | |

It is certified that error appears in the above-identified patent and that said Letters Patent is hereby corrected as shown below:

On the Title Page

Page 6, In Column 2, Line 6, item (56) under U.S. Patent Documents, delete "2/2023 Ai-Ali" and insert --2/2023 Al-Ali--.

Page 6, In Column 2, Line 6, item (56) under Other Publications, delete "12f2UdiMXao, pp." and insert --l2f2UdiMXao, pp.--.

In the Specification

In Column 2, Line 22, delete "FIG. 6A-6F" and insert --FIGS. 6A-6F--.

In Column 6, Line 7, delete "may by a" and insert --may be a--.

In Column 6, Line 39, delete "other emodiments, the" and insert --other embodiments, the--.

In Column 9, Line 64, delete "example configurations" and insert --example configurations.--.

In the Claims

In Column 10, Claim 2, Line 65, delete "the receptable comprises" and insert --the receptacle comprises--.

In Column 10, Claim 2, Line 67, delete "the receptable upon" and insert --the receptacle upon--.

In Column 11, Claim 4, Line 5, delete "the receptable comprises" and insert --the receptacle comprises--.

Signed and Sealed this
Tenth Day of June, 2025

Coke Morgan Stewart
*Acting Director of the United States Patent and Trademark Office*